US006303377B1

(12) United States Patent
Bower et al.

(10) Patent No.: US 6,303,377 B1
(45) Date of Patent: Oct. 16, 2001

(54) BIOTIN BIOSYNTHESIS IN *BACILLUS SUBTILIS*

(75) Inventors: Stanley Grant Bower, Arlington; John B. Perkins, Reading; R. Rogers Yocum; Janice G. Pero, both of Lexington, all of MA (US)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/407,549

(22) Filed: Sep. 28, 1999

Related U.S. Application Data

(62) Division of application No. 08/676,817, filed on Jul. 8, 1996, now Pat. No. 6,057,136, which is a continuation of application No. 08/239,430, filed on May 6, 1994, now abandoned, which is a continuation-in-part of application No. 08/084,709, filed on Jun. 25, 1993, now abandoned.

(51) Int. Cl.$^7$ ............... G12N 15/01; C12P 17/16

(52) U.S. Cl. ............... 435/441; 435/252.31

(58) Field of Search ............... 435/118, 252.31, 435/252.5, 440, 441

(56) References Cited

U.S. PATENT DOCUMENTS

| 4,563,426 | 1/1986 | Yamada et al. ............... 435/119 |
| 5,096,823 | 3/1992 | Gloeckler et al. ............... 435/252.31 |
| 5,110,731 | 5/1992 | Fisher ............... 435/119 |

FOREIGN PATENT DOCUMENTS

| 240105 A1 | * 10/1987 | (EP) . |
| 0 240 105 A1 | 10/1987 | (EP) . |
| 0 375 525 A1 | 6/1990 | (EP) . |
| 0 379 428 A1 | 7/1990 | (EP) . |
| 0 449 724 A2 | 10/1991 | (EP) . |
| 0 531 708 A2 | 3/1993 | (EP) . |
| 0 532 426 A2 | 3/1993 | (EP) . |
| 240105 B1 | * 7/1993 | (EP) . |
| 2 216 530-B2 | 10/1989 | (GB) . |
| 58-60996 | 4/1983 | (JP) . |
| 58-152495 | 9/1983 | (JP) . |
| 61-149091 | 7/1986 | (JP) . |
| 61-202686 | 9/1986 | (JP) . |
| 62-155081 | 7/1987 | (JP) . |
| 62-275684 | 11/1987 | (JP) . |
| 90-27980 | 1/1990 | (JP) . |
| 4-11894 | 1/1992 | (JP) . |
| 4-278088 | 10/1992 | (JP) . |
| 4-278093 | 10/1992 | (JP) . |
| 87/01391 | 3/1987 | (WO) . |

OTHER PUBLICATIONS

Brown, S. and Kamogawa, K., "The production of biotin by genetically modified micro–organisms," Biotechnology and Genetic Engineering Reviews, vol. 9, pp. 295–326 (1991).

Izumi et al., "The Pimelyl–CoA synthetase responsible for the first step in biotin biosynthesis in microorganisms," Agric Biol. Chem., vol. 38, pp. 2257–2262 (1974).

Ohsawa et al., "Cloning of the biotin synthetase gene from *Bacillus sphaericus* and expression in *E. coli* and Bacilli," Gene, vol. 80, pp. 39–48 (1989).

Speck et al., "Isolation of *Bacillus sphaericus* biotin synthesis control mutants: evidence for transcription regulational of bio genes," Gene, vol. vol. 108, pp. 39–45 (1991).

Pai, "Genetics of Biotin Biosynthesis in *Bacillus subtilis*," J. of Bacteriology, vol. 121, pp. 1–8 (1975).

Sabatié "Biotin formation by recombinant strains of *Escherichia coli*: influence of the host physiology," Journal of Biotechnology, vol. 20, pp. 29–50 (1991).

Stackerbrandt et al., "Comparative 16S rRNA Oligonucleotide Analyses and Murein Types of Round–spore–forming Bacilli and Non–spore–forming Relatives," J. of General Microbiology, vol. 133, pp. 2323–2529 (1987).

JAPIO Abstract, Accession No. 87–275684 (Abstract of Japanese Application No. JP–62–275684).

JAPIO Abstract, Accession No. 83–060996 (Abstract of Japanese Application No. JP–58–60996).

JAPIO Abstract, Accession No. 86–202686 (Abstract of Japanese Application No. JP–61–202686).

JAPIO Abstract, Accession No. 86–149091 (Abstract of Japanese Application No. JP–61–149091).

WPAT Abstract, Accession No. 87–231579/33 (Abstract of Japanese Application No. JP–62–155081).

JAPIO Abstract, Accession No. 83–152495 (Abstract of Japanese Application No. JP–58–152495).

Priest, In Sonensheim et al. (eds.), "*Bacillus subtilis* and other Gram–Positive Bacteria," Ameri. Soc. Microbio., pp. 3–16 (1993).

Ohsawa et al., J. Fermentation Bioeng., vol. 73, pp. 121–124 (1992).

Fujisawa et al., Biosci. Biotech. Biochem., vol. 57, pp. 740–744 (1993).

Gloeckler et al., Gene, vol. 87, pp. 63–70 (1990).

Perkins et al., in Sonensheim et al. (eds.), "*Bacillus subtilis* and other Gram–Positive Bacteria," Ameri. Soc. Microbiol., pp. 319–334 (1993).

* cited by examiner

*Primary Examiner*—Nashaat T. Nashed
*Assistant Examiner*—Christian L. Fronda
(74) *Attorney, Agent, or Firm*—Mark E. Waddell; Stephen M. Haracz; Bryan Cave LLP

(57) ABSTRACT

The invention generally provides the genes of the biotin biosynthetic operon of *Bacillus subtilis*, and closely related species thereof, and well as constructions useful for high level production of biotin.

1 Claim, 28 Drawing Sheets

NUCLEOTIDE SEQUENCE OF THE B. SUBTILIS BIO PROMOTER REGION.

```
                                                              PUTATIVE RHO-INDEPENDENT
                                                           TRANSCRIPTIONAL TERMINATION SITE
                                                           ----------------------------------
AAGCTGTGTCCGGTTTTGCAAAAGTGGCTGTGACTGTAAAAAGAAATCGAAAAAGACCCGTTTTGTGTGAAAACGTCTTTTGTTTCCTTTTAACCAACTG    300
 A  V  R  F  L  Q  K  W  L
            END ORF4-5

ClaI*                         -35            σ^A                 -10        HpaI
                                                                    --------
CCATAAATCGATCCTTTCTTCTATTGACAGAAACAGGAGAGAATAATATATTCTAATTGTTAACCTTTGAATATAATTGGTTAACAATTTAGGTGAGAAG    400
                                                                                        HpaI
                                                                  _____
                                                                  POSSIBLE TRANSCRIPTIONAL REGULATORY SITE

Eco47III            RBS                                                                   BspIH
CGCTACACGTTCTTCAGTTATCAGTGAAAGGGCGAGAAATGATGCAAGAAGAAACTTTTTATAGTGTCAGAATGAGGGCTTCAATGAATGGATCTCATGA    500
                                   M  M  Q  E  E  T  F  F  Y  S  V  R  M  R  A  S  M  N  G  S  H  E
                                  START bioW
```

FIG. 4

1 COMPLEMENTATION VERSUS E. COLI BIO MUTANTS. MUTANTS TESTED ARE INDICATED WITH A + (COMPLEMENTATION) OR - (NO COMPLEMENTATION). MUTANTS NOT LISTED WERE NOT TESTED.

FIG. 7

¹ COMPLEMENTATION VERSUS E. COLI BIO MUTANTS. MUTANTS TESTED ARE INDICATED WITH A + (COMPLEMENTATION), ? (PARTIAL COMPLEMENTATION), OR − (NO COMPLEMENTATION). MUTANTS NOT LISTED WERE NOT TESTED.

```
   1  CGCATCGGAG ATCCAAAGCC TGATCGCGCC GCGCCCGCAC CTTAGTCTTG
  51  TTGGTGTACA CGATCGGTTA ACGCCGGCTG AGGGCGTGGA CAAAATCGAA
 101  AAAGAATTGA CAGCTGTCTA TGCTGGACAG GGAGCTGCTG ATTGCTACCG
 151  AGTGGTCCGT TCTGCTTCGG GACATTTCGA AACAGCAGTT ATAAGGCATG
 201  AAGCTGTCCG GTTTTTGCAA AAGTGGCTGT GACTGTAAAA AGAAATCGAA
 251  AAAGACCGTT TTGTGTGAAA ACGGTCTTTT TGTTTCCTTT TAACCAACTG
 301  CCATAAATCG ATCCTTTCTT CTATTGACAG AAACAGGAGA GAATAATATA
 351  TTCTAATTGT TAACCTTTGA ATATAATTGG TTAACAATTT AGGTGAGAAG
 401  CGCTACACGT TCTTCAGTTA TCAGTGAAAG GGCGAGAAAT GATGCAAGAA
 451  GAAACTTTTT ATAGTGTCAG AATGAGGGCT TCAATGAATG GATCTCATGA
 501  AGACGGCGGA AAGCATATAT CCGGCGGAGA ACGGCTTATT CCTTTCCATG
 551  AGATGAAGCA TACAGTCAAT GCTTTATTAG AAAAAGGGTT ATCCCATTCA
 601  AGAGGAAAAC CTGATTTTAT GCAAATTCAA TTTGAAGAGG TACATGAATC
 651  GATAAAAACC ATTCAGCCAT TGCCTGTGCA TACGAATGAA GTGAGCTGCC
 701  CGGAAGAAGG ACAAAAGCTT GCCCGATTGT TATTGGAAAA AGAAGGCGTT
 751  TCACGAGACG TGATTGAAAA AGCATATGAA CAAATCCCTG AATGGTCAGA
 801  TGTCAGGGGT GCGGTGTTGT TTGATATTCA TACAGGCAAG CGAATGGATC
 851  AAACAAAAGA AAAAGGGGTG CGGGTCTCCA GAATGGATTG GCCGGACGCT
 901  AATTTTGAAA ATGGGCGCT TCACAGTCAC GTGCCAGCTC ATTCAAGAAT
 951  AAAAGAGGCC CTTGCGCTCG CTTCAAAGGT AAGCCGGCAC CCGGCAGTCG
1001  TTGCAGAATT ATGCTGGTCG GACGATCCGG ATTACATAAC AGGCTATGTT
1051  GCGGGTAAGA AAATGGGCTA TCAGCGTATT ACAGCAATGA AGAATACGG
1101  GACTGAAGAG GGCTGCCGAG TCTTTTTTAT TGATGGATCC AATGATGTAA
1151  ACACGTACAT ACATGACCTG GAGAAGCAGC CTATTTTAAT AGAGTGGGAG
```

FIG. 14A

```
1201  GAAGATCATG ACTCATGATT TGATAGAAAA AAGTAAAAAG CACCTCTGGC
1251  TGCCATTTAC CCAAATGAAA GATTATGATG AAAACCCCTT AATCATCGAA
1301  AGCGGGACTG GAATCAAAGT CAAAGACATA AACGGCAAGG AATACTATGA
1351  CGGTTTTTCA TCGGTTTGGC TTAATGTCCA CGGACACCGC AAAAAAGAAC
1401  TAGATGACGC CATAAAAAAA CAGCTCGGAA AAATTGCGCA CTCCACGTTA
1451  TTGGGCATGA CCAATGTTCC AGCAACCCAG CTTGCCGAAA CATTAATCGA
1501  CATCAGCCCA AAAAGCTCA CGCGGGTCTT TTATTCAGAC AGCGGCGCAG
1551  AGGCGATGGA ATAGCCCTA AAAATGGCGT TCAGTATTG GAAGAACATC
1601  GGGAAGCCCG AGAAACAAAA ATTCATCGCA ATGAAAAACG GGTATCACGG
1651  TGATACGATT GGCGCCGTCA GTGTCGGTTC AATTGAGCTT TTTCACCACG
1701  TATACGGCCC GTTGATGTTC GAGAGTTACA AGGCCCCGAT TCCTTATGTG
1751  TATCGTTCTG AAAGCGGTGA TCCTGATGAG TGCCGTGATC AGTGCCTCCG
1801  AGAGCTTGCA CAGCTGCTTG AGGAACATCA TGAGGAAATT GCCGCGCTTT
1851  CCATTGAATC AATGGTACAA GGCGCGTCCG GTATGATCGT GATGCCGGAA
1901  GGATATTTGG CAGGCGTGCG CGAGCTATGT ACAACATACG ATGTCTTAAT
1951  GATCGTTGAT GAAGTCGCTA CAGGCTTTGG CCGTACAGGA AAAATGTTTG
2001  CGTGCGAGCA CGAGAATGTC CAGCCTGATC TGATGGCTGC CGGTAAAGGC
2051  ATTACAGGAG CTATTTGCC AATGCCGTT ACGTTTGCCA CTGAAGACAT
2101  CTATAAGGCA TTCTATGATG ATTATGAAAA CCTAAAAACC TTTTTCCATG
2151  GCCATTCCTA TACAGGCAAT CAGCTTGGCT GTGCGGTTGC GCTTGAAAAT
2201  CTGGCATTAT TTGAATCTGA AAACATTGT GAACAAGTAG CGGAAAAAAG
2251  TAAAAAGCTC CATTTTCTTC TTCAAGATCT GCACGCTCTT CCTCATGTTG
2301  GGGATATTCG GCAGCTTGGC TTTATGTGCG GTGCAGAGCT TGTACGATCA
2351  AAGGAAACTA AAGAACCTTA CCCGGCTGAT CGGCGGATTG GATACAAAGT
2401  TTCCTTAAAA ATGAGAGAGT TAGGAATGCT GACAAGACCG CTTGGGGACG
2451  TGATTGCATT TCTTCCTCCT CTTGCCAGCA CAGCTGAAGA GCTCTCGGAA
2501  ATGGTTGCCA TTATGAAACA AGCGATCCAC GAGGTTACGA GCCTTGAAGA
```

FIG. 14B

2551  TTGATTCCTG GTTAAACGAG CGGTTAGACA GAATGAAAGA AGCCGGCGTA
2601  CATCGTAACC TGCGGTCAAT GGATGGAGCG CCGGTTCCAG AGAGGAATAT
2651  TGATGGCGAA AATCAAACGG TCTGGTCCTC AAACAATTAT TTAGGGCTCG
2701  CAAGCGATAG ACGTTTGATC GATGCAGCCC AAACAGCATT GCAGCAATTT
2751  GGGACAGGAA GCAGCGGTTC ACGTTTAACG ACAGGCAATT CGGTCTGGCA
2801  TGAAAAGCTA GAAAAGAAGA TTGCCAGCTT TAAACTGACA GAAGCGGCCC
2851  TGCTGTTTTC GAGCGGTTAC TTGGCCAATG TCGGTGTCCT TTCATCCTTG
2901  CCAGAAAAGG AAGATGTCAT TTTAAGTGAC CAGCTCAATC ATGCAAGTAT
2951  GATCGACGGC TGCCGACTTT CTAAGGCTGA TACAGTTGTT TATCGGCATA
3001  TTGATATGAA TGATCTTGAA AACAAGCTGA ATGAAACACA GCGTTATCAG
3051  CGCCGTTTTA TCGTAACAGA CGGAGTATTC AGCATGGATG GCACAATCGC
3101  CCCTCTTGAT CAGATCATCT CACTTGCGAA ACGCTATCAT GCCTTCGTGG
3151  TCGTTGATGA TGCCCACGCA ACAGGAGTTT TGGGCGATTC GGGACAAGGA
3201  ACGAGTGAAT ACTTTGGTGT TTGTCCCGAC ATTGTTATCG GCACCTTAAG
3251  CAAAGCTGTT GGCGCGGAAG GAGGTTTTGC GGCAGGATCA GCGGTCTTCA
3301  TCGACTTTTT GCTGAACCAT GCCAGAACAT TTATCTTTCA AACCGCTATT
3351  CCGCCAGCCA GCTGTGCGGC TGCTCACGAG GCTTTCAACA TCATTGAAGC
3401  CAGCAGGGAA AAACGACAGC TTTTATTTTC TTATATCAGC ATGATCAGAA
3451  CCAGTCTGAA GAATATGGGT TATGTGGTGA AAGGAGATCA CACACCGATT
3501  ATTCCTGTAG TCATTGGCGA TGCCCATAAA ACGGTCCTAT TTGCTGAAAA
3351  ACTGCAGGGC AAGGGAATTT ATGCTCCTGC CATTCGGCCG CCAACCGTTG
3601  CGCCGGGTGA AAGCCGGATT CGAATTACAA TCACGTCTGA CCACAGTATG
3651  GGTGATATTG ATCATTTGCT GCAAACATTT CATTCAATCG GAAAGGAGCT
3701  GCACATCATT TGAGGGGTTT TTTTGTGACG GGAACTGATA CAGAAGTAGG
3751  GAAAACGGTT ATATCCAGCG GTCTTGCTGC CTTATTGAAA GACAATAATA
3801  GACATGTCGG GGTGTATAAA CCATTTTTAA GCGGGATATC GCGCCATCAT
3851  CCAGATAGTG ATACAAGTTT GCTGAAAGAT ATGTCGCAGA CCAGTCTTTC

FIG. 14C

```
3901  TCATGAAGAC ATTACGCCTT TTGCCTTCAA GGCGCCGCTT GCACCATACG
3951  TTGCAGGGAA ACTTGAGGGA AAGACTGTCA CCATGGAAGA GGTTTTAAGC
4001  CATTGGGGGC GGATTAGAGA AAAACATGAA TGCTTCATCG TAGAAGGTGC
4051  AGGCGGTATT TCTGTGCCAT TGGGAGAGGA CTATTTGGTC AGTCATGTCA
4101  TAAAAGCGTT GCAGCTTCCC ATGATTATTG TGGCGCGTCC TCGCCTTGGA
4151  ACCATTAATC ATACCTTTTT AACTGTCAAA TATGCAGAAA GCATGGGGCT
4201  TCCAATCGCC GGAATTATCA TCAATGGAAT CAGTGACTCT CCTGATGAAG
4251  ATGAAAAAAC CAATCCTGAG ATGATTGAGC GCTTATGCGG TGTGCCGATT
4301  TTAGGGGTTA CGCCAAAGCT TGCCAACGTG ACGAAAGAAA CGGTTCTACA
4351  TATGGTAAAA GACCATATCA ATCTATCATT ACTGATGAAT CAAGTGGGGG
4401  TATGAGAATG AATCAATGGA TGGAACTCGC AGACCGGGTG CTGGCTGGAG
4451  CAGAAGTGAC TGACGAAGAG GCGCTTTCAA TATTACATTG TCCTGATGAA
4501  GATATTTTGC TATTAATGCA CGGGGCTTTT CACATCAGAA AACACTTTTA
4551  CGGAAAAAAA GTAAAGCTCA ATATGATTAT GAATGCGAAA TCCGGGCTCT
4601  GCCCGGAAAA CTGCGGCTAT TGTTCACAGT CTGCGATTTC GAAAGCGCCG
4651  ATTGAGTCTT ACCGGATGGT GAATAAGGAA ACGCTGCTTG AAGGCGCGAA
4701  GCGGGCGCAC GATCTGAATA TCGGCACATA TTGTATCGTG GCAAGCGGCA
4751  GAGGTCCGTC TAACAGAGAA GTGGATCAGG TCGTAGATGC GGTTCAGGAA
4801  ATTAAAGAGA CGTATGGACT GAAGATTTGT GCATGTCTTG GACTGTTGAA
4851  GCCAGAGCAG GCGAAGCGGC TCAAAGATGC AGGAGTAGAC CGCTATAATC
4901  ATAATTTGAA TACGTCACAG AGAAACCATT CAAACATCAC AACCTCACAT
4951  ACATACGATG ACAGAGTCAA TACGGTTGAA ATCGCAAAAG AATCGGGGCT
5001  GTCTCCGTGT TCAGGCGCCA TTATCGGGAT GAAGGAGACG AAACAGGATG
5051  TCATTGACAT CGCCAAAAGC TTGAAGGCTC TTGACGCGGA TTCCATTCCT
5101  GTGAATTTTT TGCATGCAAT TGATGGCACG CCGTTAGAAG GCGTCAACGA
5151  ATTAAACCCG CTGTATTGTT TAAAAGTGCT GGCGCTGTTC CGTTTTATCA
5201  ATCCATCAAA AGAAATTCGC ATTCCGGAG GAAGAGAGGT CAATCTCCGC
```

FIG. 14D

```
5251  ACATTGCAGC CATTAGGGCT TTACGCCGCA AACTCCATTT TTGTCGGAGA
5301  CTACTTAACA ACTGCCGGGC AAGAGGAGAC GGAGGATCAT AAAATGCTGA
5351  GTGATTTAGG CTTTGAAGTT GAATCAGTCG AAGAAATGAA GGCTAGTTTA
5401  AGTGCGAAAA GCTGAAAGAA TCAATAAAAG CAATCGGTAT GATGTCGATT
5451  GTTTTTATTT TTGAACAGAA AGGAGAAAAT CACGTGACAA TTGCATCGTC
5501  AACTGCATCT TCTGAGTTTT TGAAAAACCC ATATTCTTTT TACGACACAT
5551  TGCGAGCTGT TCATCCTATC TATAAAGGGA GTTTCTTAAA ATACCCGGGC
5601  TGGTATGTCA CAGGATATGA AGAAACGGCT GCTATTTTGA AAGATGCGAG
5651  ATTCAAAGTC CGCACCCCGC TGCCTGAGAG CTCAACCAAA TATCAGGACC
5701  TTTCACATGT GCAAAATCAA ATGATGCTGT TCAGAACCA GCCTGATCAT
5751  AGACGATTGC GGACGCTTGC CAGCGGAGCG TTTACGCCGA GAACGACAGA
5801  GAGTTATCAG CCGTATATCA TTGAAACTGT CCATCATTTG CTTGATCAAG
5851  TGCAAGGTAA AAAAAAGATG GAGGTCATTT CGGACTTTGC TTTTCCTTTA
5901  GCAAGTTTTG TCATAGCTAA CATTATAGGT GTACCGGAGG AAGATAGGGA
5951  GCAATTAAAG GAGTGGGCTG CGAGTCTCAT TCAAACGATT GATTTTACCC
6001  GCTCAAGAAA GGCATTAACA GAGGGCAATA TTATGGCTGT GCAGGCTATG
6051  GCATATTTCA AAGAGCTGAT TCAAAAGAGA AAACGCCACC CTCAACAGGA
6101  TATGATCAGC ATGCTCTTGA AGGGGAGAGA AAAGGATAAG CTGACGGAAG
6151  AGGAGGCGGC ATCTACGTGC ATATTGCTGG CGATCGCCGG ACATGAGACA
6201  ACGGTCAATC TCATCAGCAA TTCAGTCCTT TGTCTGCTGC AGCATCCAGA
6251  ACAGCTTTTG AAACTGAGAG AAAATCCAGA TCTTATTGGT ACCGCAGTCG
6301  AGGAATGTTT ACGCTATGAA AGCCCCACGC AAATGACAGC CAGAGTTGCG
6351  TCAGAGGATA TTGACATCTG CGGGGTGACG ATCCGTCAAG GAGAACAAGT
6401  CTATCTTTTG TTAGGAGCGG CTAATCGAGA CCCTAGCATA TTCACGAACC
6451  CCGATGTCTT CGATATTACG AGAAGTCCTA ATCCGCATCT TTCATTCGGG
6501  CATGGCCATC ATGTTTGCTT AGGGTCCTCG CTGGCACGAT TAGAAGCGCA
6551  AATTGCGATT AACACTCTTC TGCAGCGAAT GCCCAGCCTT AATCTTGCGG
```

FIG. 14E

```
6601  ATTTTGAATG GCGGTATCGG CCGCTTTTTG GATTTCGGGC GCTTGAGGAG
6651  CTGCCGGTGA CTTTTGAATA AGCCTAAGAA TGTGAGTGCC AAAAAAGTGT
6701  CAGCCCCGCC GAAAATGGGC AATCTATAAA AAAGGGGAGT GAACATCGTG
6751  AAAAAAGTGC TGATCGCCGG CGGAAATGGT GTGATTGGGA GACTGCTTGC
6801  TGAAGGGCTT ATTTCAGACT ATGAAGTGAC TGTGCTTGAT AAAGATCATT
6851  TCGATGGCAA AGCCTCTTCC ATTCAGGCTG ACGCGGCAAA TTATGAGGAG
6901  CTGTTGAAGA AGATTCCAAA AGATACCGAT GCCATCTTGA ATTTACTCGC
6951  TGTGAAAATC AAATACGATA TTATGGACAT CGCTGAGTTT GAAAAAATGA
7001  CGGATGTTTT CTATAGGGCA AGCTATTATC TGTGCCGTGC GGCAGCGGAG
7051  CTCGGCATTC AAAAGCTCGT GTTCGCCAGC AGCAATCATG TCACAGATGT
7101  ATATGAAAAA GACGGGCGCT CGCTCTTAGG ACGGGAAATC ACAACAAGCG
7151  ATTATCCGCT GTCAAAAAAC TTGTACGGTG TATTAAAGCT GACCTCTGAA
7201  CAGATCGGCC ATTTGTTTTA TTTGGAAAAT AAGCTATCAG TAATCAACCT
7251  TCGAATCGGA ACAGTCGTGA CAGATGAAAT GGATACGCTG CATGAAAAAG
7301  AACGGACGAA AAAGACACTG CTTTCTCACC CCGATCTGCT GTCGATTTTC
7351  AAAGCCGCCA TTGAGACCAA CATCCGGTAT GGCACTTATT ACGCCGTCTC
7401  TGATAATCCG GGCCGGCCAT GGTCCATTGA ATCTGCCGTG AATGAACTTG
7451  GGTTTTCGCC ACAAATCAAT ACGGCTGAAC TTCTGAACGA GGAGGAGAAC
7501  GGAGCATAAT CATTTTCTAA GATTATGCTC TTTTTCTTTT GTTATCGGTC
7551  TCAATTCGCG GCAGCCCCCG CCCGGCCGGG GACACTGTTC AAATGATTAT
7601  AGACATGGCA ATCACAGATT TGCTACATTT TAGACACGAT ATCGTCACAT
7651  GCTGAGCTCG GTTTCCAAAA ATATGATAAC GCTTACAAAG GGAGGTGGGA
7701  GCTATCGCAC ATTCACTGAA AAACCGTCTG TTTGATATGT TGATTTATGG
7751  TTTCTTGCTG ATGTTCGCTT TAATATGCGT ACTTCCGTTC ATTCATGTTA
7801  TCGCAGCATC CTTTGCCACA GTAGAAGAAG TCGTGTCGAA AAAATTTATT
7851  TTAATACCGA CCACTTTTTC GCTAGATGCT TATCGCTACA TTTTTTCAAC
7901  AGATATTATT TATAAGAGTT TGCTTGTTTC TGTGTTTGTG ACAGTGATAG
```

FIG. 14F

```
7951  GCACTGCGGT CAGCATGTTT CTTTCGTCAC TGATGGCTTA CGGGTTATCC
8001  CGCCGTGATT TAATCGGCCG GCAGCCGCTC ATGTTTCTCG TCGTATTTAC
8051  GATGCTGTTT AGCGGCGGCA TGATTCCGAC TTTCCTTGTG GTCAAATCGC
8101  TTGGATTGCT CGATTCTTAC TGGGCGCTTA TTTTGCCGAC AGCCATTAAT
8151  GCCTTTAACC TGATCATTCT GAAAAACTTC TTTCAAAATA TCCCGTCAAG
8201  CCTGGAAGAG TCCGCGAAAA TTGACGGGTG CAATGATCTG GCATATTCT
8251  TTAAAATTGT GCTGCCGCTG TCTCTTCCTG CGATCGCAAC GATTTCACTA
8301  TTTTATGCGG TCACGTATTG AACACGTAT ATGACAGCGA TCTTGTACTT
8351  AAATGATTCA GCAAAATGGC CAATTCAGGT GCTTCTGCGC CAAATCGTCA
8401  TTGTATCAAG CGGTATGCAG GGGGATATGT CTGAAATGGG GTCGGGCAGC
8451  CCGCCGCCTG AGCAAACCAT NNNNNTGG
```

FIG. 14G

ELEMENTS OF THE bioW PUTATIVE CATABOLITE REPRESSION SEQUENCE.

| | ......Asp | Gly | Ser | Asn | Asp | Val | Asn | Thr | Tyr | Ile | His | Asp....... | |
|---|---|---|---|---|---|---|---|---|---|---|---|---|---|
| TT | GAT | GGA | TCC | AAT | GAT | GTA | AAC | ACG | TAC | ATA | CAT | GAC | |
| | | BamHI | | | | T | T | A | T | | | | ← INTRODUCED MUTATIONS |
| | | | | | T | GWA | ANC | GNT | NWC | A | | | CONSENSUS CATABOLITE REPRESSOR SEQUENCE |
| | | | | | T | GNR | WNN | A | | | | | CONSENSUS abrB SEQUENCE |

UNDERLINED NUCLEOTIDES ARE THOSE BELIEVED TO BE MOST ESSENTIAL FOR CATABOLITE REPRESSOR FUNCTION.

NUCLEOTIDES: N - ANY NUCLEOTIDE, R - PURINE, W - WEAK, I.E. A OR T.

BIOTIN BIOSYNTHESIS IN *BACILLUS SUBTILIS*

This is a divisional of U.S. application Ser. No. 08/676,818, filed Jul. 8, 1996 (U.S. Pat. No. 6,057,136); which is a Rule 62 Continuation of U.S. application Ser. No. 08/239,430, filed May 6, 1994 abandoned; which is a Continuation-In-Part of U.S. application Ser. No. 08/084,709, filed Jun. 25, 1993 abandoned.

This application is a continuation-in-part of U.S. Ser. No. 08/084,709 filed Jun. 25, 1993. This invention relates to the production of biotin using a genetically engineered organism.

BACKGROUND OF THE INVENTION

Biotin (vitamin $B_8$ or vitamin H), a coenzyme for carboxylation and decarboxylation reactions, is an essential metabolite for living cells. Exogenous biotin is required for most higher organisms; however many bacteria synthesize their own biotin.

The enzymatic steps involved in the biotin synthetic pathway from pimelyl-CoA (PmCoA) to biotin have been elucidated in *Escherichia coli* and *Bacillus sphaericus* (FIG. 1; reviewed in Perkins and Pero, *Bacillus subtilis and other Gram-Positive Bacteria*, ed. Sonenshein, Hoch, and Losick, Amer. Soc. of Microbiology, pp. 325–329, 1993). The steps include the conversions of 1) pimelyl-CoA to 7-keto-8-amino pelargonic acid; (7-KAP or KAPA) by 7-KAP synthetase (bioF); 2) 7-KAP to 7,8-diamino-pelargonic acid (DAPA) by DAPA aminotransferase (bioA); 3) DAPA to dethiobiotin (DTB) by DTB synthetase (bioD); and 4) DTB to biotin by biotin synthetase (bioB). Synthesis of PmCoA reportedly involves different enzymatic steps in different microorganisms. The *E. coli* genes involved in steps preceding pimelyl-CoA synthesis include bioC (Otsuka et al., *J. Biol. Chem.* 263:19577–19585 (1988)) and bioH (O'Regan et al., *Nucleic Acids Res.* 17:8004 (1989)). In *B. sphaericus*, two different genes, bioX and bioW, are thought to be involved in PmCoA synthesis. BioX is thought to be involved in pimelate biosynthesis (Gloeckler et al., *Gene* 87:63–70, 1990), and bioW has been shown to encode pimelyl-CoA synthetase which converts pimelic acid (PmA) to PmCoA (Ploux et al., *Biochem. J.* 287:685–690, 1992). Neither *B. sphaericus* gene, bioW or bioX, has significant sequence similarity with the *E. coli* bioC and bioH genes either at the nucleotide or protein level (Gloeckler et al., 1990, supra).

In *E. coli*, the biotin biosynthetic genes are located in three or more operons in the chromosome. The bioA gene is located in one operon and the bioBFCD genes are located in a second closely linked operon. The bioH gene is unlinked to the other bio genes (FIG. 2; Eisenberg, M. A. 1987 in *Escherichia coli and Salmonella typhimurium: Cellular and Molecular Biology*, vol. 1, Amer. Soc. Micro. Wash. D.C.).

In *B. sphaericus*, the organization of the bio genes is clearly different from that in *E. coli*. Gloeckler et al. (1990, supra) have isolated and characterized two unlinked DNA fragments from *B. sphaericus* that encode bio genes. One fragment contains an operon encoding the bioD, bioA, bioy, and bioB genes, and the other fragment contains an operon encoding the bioX, bioW and bioF genes (FIG. 2). The order and clustering of bio genes is different in *E. coli* and *B. sphaericus* (FIG. 2).

Fisher U.S. Pat. No. 5,110,731 provides a system for producing biotin wherein the genes of the biotin operon of *E. coli* are transformed into, and expressed in, a retention-deficient strain of *E. coli*.

Gloeckler et al. U.S. Pat. No. 5,096,823 describes genes involved in the biosynthesis of biotin in *B. sphaericus*: bioA, bioD, bioF, bioC, and bioH. *B. sphaericus* genes for bioA and bioD were cloned into both *E. coli* and *B. subtilis*. The bioA and bioD genes were stably integrated into *B. subtilis* Bio⁻ auxotrophs, and prototrophic strains were selected.

GB 2,216,530-B2 (Jul. 8, 1992; Minister of Agr & Fisheries) provides plasmids containing gene(s) for *E. coli* bioA, bioB, bioC, bioD, and bioF isolated from other *E. coli* genetic material, e.g., control sequences. The plasmids are capable of replicating and being expressed in non-*E. coli* strains, preferably in yeast.

Three biotin synthesis deficient mutants of *B. subtilis* (bioA, bioB, and a gene termed bio112 which may be analogous to *E. coli* bioF) have been reported (Pai, *Jour. Bact.* 121:1–8, 1975; and Gloeckler et al., 1990, supra).

Nippon Zeon Co. Ltd. U.S. Pat. No. 4,563,426 discloses biotin fermentation that includes adding pimelic acid after culturing for about 24 hours. Transgene SA and Nippon Zeon Co. Ltd. E.P. 0 379 428 discloses adding pimelic acid to a biotin fermentation medium.

SUMMARY OF THE INVENTION

The invention generally provides the genes of the biotin synthetic operon of *B. subtilis* and closely related species to be used for high level production of biotin. Specific aspects of the invention are described in greater detail below. We have specifically identified, cloned, and engineered a previously unknown gene (bioI), which encodes a cytochrome P-450-like enzyme. We have also developed a strategy to overexpress the entire *B. subtilis* bio operon (which, when engineered with a strong promoter, is unexpectedly toxic to *E. coli*) by cloning two bio operon fragments separately, combining them in vitro, and transforming the host organism with the resulting ligated construction. Cloning the two fragments was further complicated by difficulty obtaining the 5' end of the operon, due to toxicity in *E. coli*. The invention particularly features the full-length operon obtained by the above strategy. These and other features of the invention are described in greater detail below.

In one aspect, therefore, the invention features vector-derived DNA comprising: (a) a gene that encodes a biotin biosynthetic enzyme of *Bacillus subtilis*, or of a species closely related to *Bacillus subtilis*; (b) a biologically active fragment of (a); or (c) a DNA sequence that is substantially homologous to (a) or (b). We use the term "vector-derived" to include DNA that can be used to transform a cell and the DNA included in such a cell after transformation. Such vector-derived DNA differs from naturally occurring DNA, either by mutation or by its inclusion in a molecule that is different from the DNA molecule in which it naturally occurs. Also, as used herein, a species which is "closely related" to *B. subtilis* includes a member of a cluster of Bacillus spp. represented by *B. subtilis*. The cluster includes, e.g., *B. subtilis, B. pumilus, B. licheniformis, B. amyloliquefaciens, B. megaterium, B. cereus* and *B. thuringiensis*. The members of the *B. subtilis* cluster are genetically and metabolically divergent from the more distantly related Bacillus spp. of clusters represented by *B. sphaericus* and *B. stearothermophilus* (FIG. 3; Priest, in *Bacillus subtilis and other Gram-Positive Bacteria*, supra pp. 3–16, hereby incorporated by reference; Stackebrandt, et al. *J. Gen. Micro.* 133:2523–2529, 1987, hereby incorporated by reference).

As noted above, we have discovered a novel gene (bioi) present in *B. subtilis* and closely related species thereof, which is particularly important to deregulated production of biotin, and that gene is included in the DNA of preferred embodiments of the first aspect of the invention. Also preferably, at least bioA and bioB are included in the DNA of the first aspect. BioD, bioF, bioW, and ORF2 (encoding a β-keto reductase-like enzyme) may also be advantageously included in the DNA of the invention. At least two of the above-defined genes may be included in the DNA. The gene(s) may be operably linked to a transcriptional promoter, e.g., a constitutive promoter such as a promoter derived from the SP01 bacteriophage. The entire biotin operon of *Bacillus subtilis*, or a closely related species thereof, may be linked to a single transcriptional promoter. Moreover, we have learned that it is particularly useful to include a second promoter—i.e., one or more of the genes is operably linked to a first transcriptional promoter, and at least a second one of the genes is operably linked to a second transcriptional promoter. The first promoter may be operably linked to one or more of bioA, bioB, bioD, bioF, and bioW of *B. subtilis*, or a closely related species thereof. The other promoter may be operably linked to one or more of bioI, bioA, bioB, or a combination thereof. In a particularly preferred embodiment, the first promoter controls transcription of the entire operon, and transcription of bioI, optionally with bioA and or bioB, is also controlled by the second promoter. The DNA may include a mutated regulatory site of a biotin operon of *B. subtilis* or a closely related species, such as an operator, a promoter, a site of transcription termination, a site of MRNA processing, a ribosome binding site, or a site of catabolite repression. By mutation, we mean an insertion, a substitution, or a deletion with respect to the wild type regulatory site.

A second aspect of the invention relates to our discovery of *Bacillus subtilis* bioI. This aspect features that gene or a gene specifically hybridizable to *Bacillus subtilis* bioI. It also features a biotin biosynthetic enzyme encoded by such a gene.

The invention also features cells comprising the DNA of either of the above two aspects of the invention. Preferably, the DNA is amplified to multiple copies in such cells. Also preferably, the DNA is stably integrated into the chromosome of the cell. The DNA may be integrated at multiple sites in the chromosome, at least one of which is the bio locus, and in multiple copies at each such site. Also preferably, the cell is characterized by a mutation that deregulates production of biotin or a biotin precursor, in addition to the presence of the DNA. Such mutated cells produce an increase in biotin in comparison to wild-type cells lacking the DNA. Such a mutation may be one that confers resistance to azelaic acid and/or it may be a mutation in birA.

The above described cells are used in methods of producing biotin or a precursor thereof in which the cells are cultured for a time and under conditions which allow synthesis of biotin or the precursor, and biotin or precursor is then isolated, preferably from the extracellular media of the cell.

Yet another aspect of the invention features a recombinant biotin biosynthetic enzyme comprising an amino acid sequence that is substantially homologous to the amino acid sequence of a biotin biosynthetic enzyme of *Bacillus subtilis*, or a closely related species thereof.

A final aspect of the invention features a method of selecting a mutant *Bacillus subtilis* cell characterized in being deregulated for biotin production, by: (a) providing a population of *Bacillus subtilis* cell; (b) allowing the population to reproduce in the presence of azelaic acid; (c) selecting a cell that is resistant to azelaic acid; and (d) screening the cell, or a daughter cell further mutated to deregulate biotin production, for the ability to overproduce biotin.

The above description of the invention may be further understood by reference to the following definitions and explanations. The vector DNA may include a sequence which is substantially homologous to a gene (or to a biologically active fragment of the gene) that encodes a biotin biosynthetic enzyme of *Bacillus subtilis*, or a closely related species thereof. The DNA sequence diverges from the wild type sequence by including a mutation, e.g., a deletion, an insertion, or a point mutation, that enhances the synthesis of biotin when the DNA sequence is expressed in a cell. At least two, three, four, five, or six, or preferably all, of the biotin operon genes, may be operably linked to a transcriptional promoter to yield a messenger RNA. As used herein, "operon" refers to one or more genes co-transcribed from the same promoter. "Biotin operon" refers to a group of genes whose gene products are involved in an aspect of biotin biosynthesis. By "promoter" is meant a nucleic acid sequence recognized by an RNA polymerase enzyme that initiates transcription of a gene located in the 3' direction of the promoter to yield a messenger RNA. By "operably linked to a transcriptional promoter" is meant that the gene is sufficiently proximal to the promoter for an RNA transcript initiated at the promoter to include messenger RNA that is complementary to that gene. The transcriptional promoter is either a constitutive promoter, e.g., a promoter derived from the SP01 bacteriophage, or an inducible promoter.

Any of the genes of the operon can include a mutation that enhances the synthesis of biotin when the DNA sequence is expressed in a cell. In a related embodiment, a regulatory site in the biotin operon, or in a gene of the biotin operon, can be altered, e.g., by mutation, so as to increase the level of biotin produced in a cell. Examples of regulatory sites that can be altered include a site of transcription termination, an operator site, a site of mRNA processing, a ribosome binding site, or a site of catabolite repression.

Any of the vectors of the invention can be included in a host cell. The preferred host cell is a *B. subtilis* cell for the reasons discussed below. However, the vectors of the invention can also be inserted into another type of host cell, e.g., an *E. coli* cell, or any host cell containing the apparati necessary to maintain the vector and/or to express a gene of the biotin operon located on the vector. Where the host cell is used for expression, it is also desirable for the host cell to have the ability to secrete biotin into the extracellular medium, as does *B. subtilis*, simplifying collection of the biotin product. Some of the host cells that can be used include, but are not limited to, Gram-positive bacteria, e.g., *B. subtilis* cells such as *B. subtilis* 168, W23, or natto strains, other Bacillus strains such as *B. licheniformis, B. amyloliquefaciens, B. pumilus, B. megaterium*, or *B. cereus* (for Bacillus strains see *Bacillus Genetic Stock Center Cataloaue of Strains*, Ohio State Univ. Depart. Biochem., Columbus, Ohio ed. by D. H. Dean, 1986, 3rd ed., hereby incorporated by reference), or other Gram-positive cells such as Lactococcus, Lactobacillus, Corynebacterium, Brevibacterium, Staphylococcus, Streptomyces, or Clostridium; Gram-negative bacteria, e.g., strains of *E. coli*, Salmonella, Serratia, or Klebsiella; or fungal cells, e.g., yeast. For strains and vectors useful with these Gram-positive cells see the book "*Bacillus subtilis* and other Gram-Positive Bacteria", ed. Sonenshein, Hoch, and Losick, Amer. Soc. of Microbiology, 1993, hereby incorporated by reference. Biotin genes from Gram-positive organisms can be expressed in Gram-negative bacteria (Gloeckler et al., supra) and even fungal genes from *Saccharomyces cerevisiae* have been expressed in *E. coli* (Zhang et al., Archives of Biochemistry and Biophysics 309:29–35 (1994)).

Where the vector is an extrachromosomal element it can be amplified, i.e., to multiple copies, in the cell. Alternatively, if the vector is not an extrachromosomal element, the vector can be stably integrated into the chromosome of the cell. Integrated vectors also can be amplified to multiple copies in the cell, i.e., integration can occur at multiple sites, or in multiple copies at each site. Integration may occur at a random site on the chromosome, or preferably integration is directed to a preferred chromosomal locus, e.g., the bio locus. The whole vector can integrate into the chromosome, or only the biotin biosynthetic sequences themselves can be integrated into the chromosome absent at least a portion of the non-biotin biosynthetic sequences, e.g., the replicon sequences. The cell containing the vector or biotin operon sequences can further be deregulated for biotin production.

By "deregulated for biotin production" is meant that a negative limitation that controls the level of biotin biosynthesis has been at least partially removed from the cell. A negative limitation includes, but is not limited to a regulatory protein (e.g., a repressor), a site of action of a regulatory protein (e.g., an operator), inhibitory factor, or a low level of a rate limiting enzyme. The cell can include a mutation in a genetic locus that complements the birA locus of *E. coli*. Examples of *B. subtilis* strains that include a mutation that causes an increase in biotin secretion include, but are not limited to, the strains HB3, HB9, HB15, HB43, αDB9, α-DB12, α-DB16, and α-DB17, or any of the mutant or engineered strains listed in Table 8, Table 9, Table 10. Biotin is preferably secreted into the extracellular media to a concentration of at least 0.1 mg/l, 1 mg/l, 10 mg/l, 100 mg/l, 300 mg/l, 500 mg/l, 750 mg/l, or 1.0 g/l. Preferably, the host cell is *B. subtilis*, but it can also be any of the above-listed host strains. By "vitamer" or "biotin vitamer" is meant any of the compounds preceding biotin in the biosynthetic pathway that can be used to feed yeast, e.g., the following compounds shown in FIG. 1: 7-KAP, DAPA, or desthiobiotin. The term "biotin precursor" includes each of the biotin vitamers listed above, as well as PmA and PmCoA. By substantially homologous we mean having sufficient homology to yield specific hybridization under conditions that allow hybridization to DNA of Bacillus species within the cluster that includes *B. subtilis*, but are too stringent to allow hybridization to DNA of organisms outside the cluster of species closely related to *B. subtilis*. Suitable probes for this purpose are provided below. Suitable hybridizations use relatively stringent conditions. For example: nitrocellulose filters containing denatured DNA are incubated with a radioactively labeled DNA or RNA probe in the presence of 5×SSC (0.75M NaCl and 0.075M Na citrate, pH 7.0), 10–50% formamide, 1×Denhardt's solution (0.02% bovine serum albumin, 0.02% Ficoll, 0.02% pyrollidone), and 100 µg/ml denatured salmon sperm DNA at 37–42° C. Those skilled in the art will understand that stringency can be gradually increased (e.g., by increasing formamide concentration or temperature) until suitable specificity is obtained (i.e., non-specific binding is reduced or eliminated).

By "biotin synthetic enzyme" is meant any one of the enzymes that form the biotin biosynthetic pathway as shown in FIG. 1, or discussed herein, as well as enzymes encoded by genes newly disclosed herein, e.g., bioI, or ORF2. The term "biotin biosynthetic enzyme" also includes a portion or fragment of a native biotin biosynthetic enzyme that performs the biochemical function of a biotin biosynthetic enzyme of *B. subtilis*. The size of such a portion or fragment of a biotin biosynthetic enzyme is determined by the functional requirement that it retain the biochemical activity of the native enzyme. There are many examples in the literature of enzymes that retain one or more activities after shortening of the polypeptide chain by proteolysis or by truncating the associated gene (for example, see Dautry-Varsat and Cohen, *J. Biol. Chem.* 252:7685–7689, 1977 hereby incorporated by reference).

As used herein, the term "fragment" or "portion", as applied to a polypeptide, will ordinarily be at least about 10 contiguous amino acids, typically at least about 20 contiguous amino acids, usually at least about 30 contiguous amino acids, preferably at least 50 contiguous amino acids, and most preferably at least about 60 to 80 contiguous amino acids in length. Similarly, by the term "fragment" in the context of a nucleic acid is meant a DNA sequence that encodes a polypeptide fragment as defined above. The ability of a candidate fragment to perform the biological activity of the corresponding naturally-occurring enzyme can be assessed by methods known to those skilled in the art, including, but not limited to, the following protocols all of which are hereby incorporated by reference: Assays of pimelyl-CoA synthetase (bioW), 7-KAP synthetase (bioF), DAPA aminotransferase (bioA), and DTB synthetase (bioD) are described by Izumi et al. (*Methods in Enzy.* 62:326–338, 1979). A cell-free assay of biotin synthetase (bioB) is described by Ifuku et al. (*Biosci. Biotech. Biochem.* 56:1780–1785, 1992). The product of bioI may be characterized as a cytochrome P-450 by the spectral determinations described by Omura et al. (*J. Biol. Chem.* 239:2310–2378, 1964).

By "recombinant" is meant that the gene encoding the enzyme has been removed from its naturally occurring site in the *B. subtilis* chromosome and inserted, either permanently or transiently, into a vector by techniques of genetic engineering known to one skilled in the art. Preferably, the vector includes sequences allowing for the expression of the inserted gene.

A "vector" as used herein refers to a nucleic acid molecule that can be introduced into a cell, e.g., by transfection, by transformation, or by transduction. Vectors include, but are not limited to, plasmids, bacteriophages, phagemids, cosmids, and transposons. Examples of vectors for use herein include, but are not limited to, pBR322, pCL1920, pCL1921, pUC18, pUC19, or pSC101. These vectors replicate in *E. coli* and other bacteria but do not replicate in *B. subtilis*, and are thus useful as integration vectors in *B. subtilis* after addition of an appropriate selectable marker. Other vectors commonly used in *B. subtilis* included the plasmids pUB110, pE194, pC194, and their derivatives which replicate in *B. subtilis*, or any of the integrational vectors, plasmids, temperate phage vectors or transposons described in Chapters 40–44 of *Bacillus subtilis and Other Gram-Positive Bacteria*, (supra, pp. 585–650). Additional vectors used in numerous microorganisms are described in *Cloning Vectors: A Laboratory Manual* (Pouwels et al. Elsevier, 1985, with supplementary updates in 1986 and 1988; hereby incorporated by reference). Recombinant, engineered *B. subtilis* DNA may also be inserted (by homologous recombination) and amplified in the *B. subtilis* chromosome without using any replicating plasmid vectors. We use the term "vector" to also include these non-replicating DNA insertions in the term "vector". The resulting integrated DNA is also included in the term "vector-derived DNA".

A "substantially pure nucleic acid," as used herein, refers to a nucleic acid sequence, segment, or fragment that has been purified or separated from the sequences which flank it in its naturally occurring state, e.g., a DNA fragment that has been removed from the sequences which are normally adjacent to the fragment, e.g., the sequences adjacent to the fragment in a genome in which it naturally occurs. The term also applies to nucleic acids which have been substantially purified from other components that naturally accompany it in the cell. Preferably, the "sequence encoding a biotin biosynthetic enzyme of *B. subtilis*" is a major component of the total purified nucleic acid sequence, e.g., at least 1% or 10% of the total nucleic acid sequence.

"Homologous," as used herein, refers to the subunit sequence similarity between two polymeric molecules, e.g., between two nucleic acid molecules, e.g., two DNA or RNA molecules, or two polypeptide molecules. When a subunit position in both of the two molecules is occupied by the same monomeric subunit, e.g., if a position in each of two DNA molecules is occupied by adenine, then they are homologous at that position. A "best-fit" homology can be achieved by adjusting the alignment of the sequences. The homology between two sequences is a function of the number of matching or homologous positions, e.g., if half (e.g., 5 positions in a polymer 10 subunits in length), of the positions in two compound sequences are homologous then the two sequences are 50% homologous, if 90% of the positions, e.g., 9 of 10, are matched or homologous, the two sequences share 90% homology. There may be gaps of non-homologous sequence among homologous sequences. "Substantially homologous" sequences are those that differ one from the other only by conservative substitutions. For example, where the substitution is in a nucleic acid sequence, the substitution either does not cause a change in amino acid at that position, or the substitution results in a conservative amino acid substitution. A "conservative amino acid substitution" is, for example, a substitution of one amino acid for another of the same class (e.g., amino acids that share characteristics of hydrophobicity, charge, $pK_a$, or other conformational or chemical properties, e.g., valine for leucine, arginine for lysine) or by one or more non-conservative amino acid substitutions, deletions, or insertions, located at positions of the amino acid sequence that do not destroy the biological activity of the polypeptide (as described above). An amino acid sequence is included within the scope of the invention if it differs by a modification that reduces or alters the biological activity of one domain of a multiple-domain enzyme, while preserving a second biological activity in a second domain of the enzyme. Generally, a polypeptide is considered to be within the scope of this invention if it is at least 75%, preferably at least 80%, or most preferably at least 90%, homologous to the naturally occurring amino acid sequence of a biotin biosynthetic enzyme of *B. subtilis*. A nucleic acid sequence is considered to be within the scope of this invention if it is at least 70%, preferably at least 80%, or most preferably at least 90%, homologous to a naturally occurring nucleic acid sequence encoding a biotin biosynthetic enzyme of *B. subtilis*.

Bacterial strains containing the *B. subtilis* genes provided herein are useful for producing high levels of biotin or of a biotin precursor, these compounds being useful in turn as a dietary additive for humans or animals. For instance, biotin can be supplied to a domesticated animal, e.g., a cow, chicken, or a pig, as an additive to a commercial preparation of animal feed. In addition, biotin can be added to a vitamin dietary supplement for human use. Biotin is also useful as a reagent for research and diagnostic procedures. For example, biotin is used as a non-radioactive label for proteins and nucleic acids. Biotin-labelled proteins are detectable by virtue of biotin's naturally occurring ability to bind to avidin, a protein found in egg-white, or to streptavidin, a biotin-binding protein produced by a streptomycete.

DETAILED DESCRIPTION

DRAWINGS

FIG. 4 is an illustration of the nucleotide sequence of the *B. subtilis* bio promoter region (SEQ ID NO:7), including amino acid translations of the end of the ORF4-5 reading frame (SEQ ID NO:16) and the beginning of the bioW reading frame (SEQ ID NO:17).

FIG. 7 shows the complementation results with deletions and subclones of pBIO201.

Figure 12:
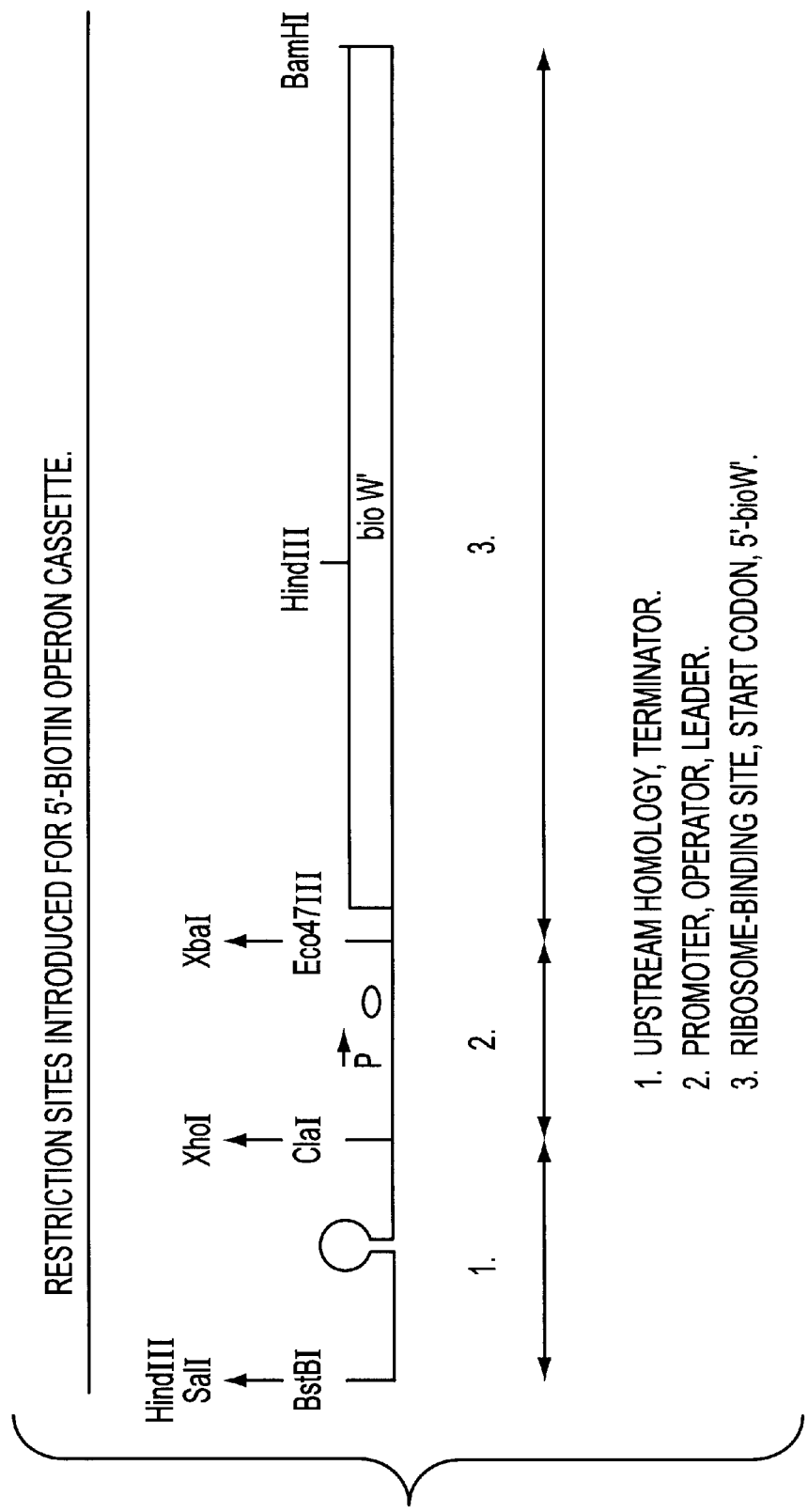

FIG. 12 is an illustration of the restriction sites introduced for the 5'-biotin operon cassette. 1. upstream homology, terminator; 2. Promoter, operator, leader; 3. Ribosome-binding site, start codon, 5'-bioW.

Figure 13A:
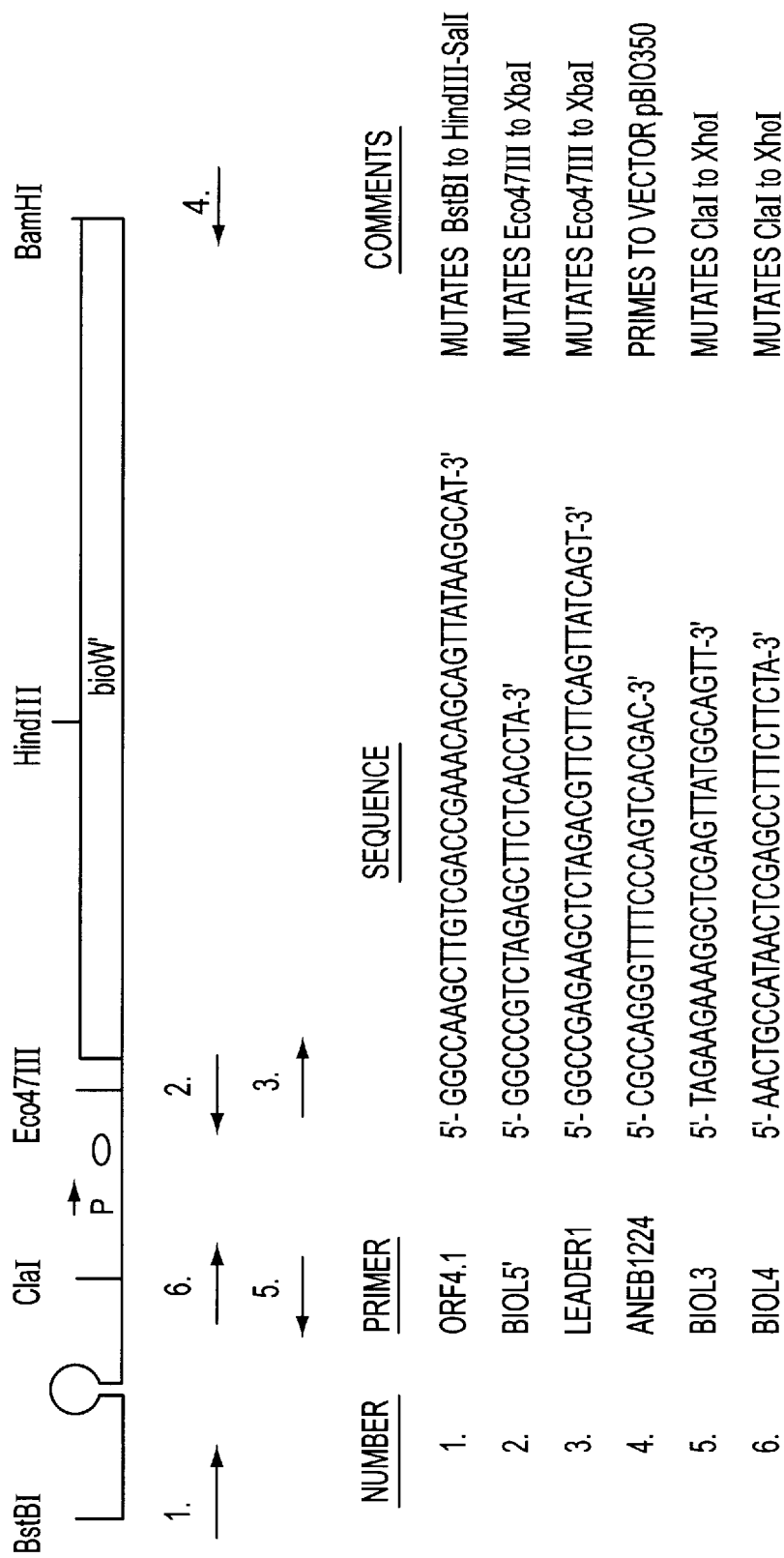

FIG. 13A shows the orientation and sequence of the following PCR primers for the 5'-bio cassette: ORF4.1 (SEQ ID NO:10), BIOL5' (SEQ ID NO:11), Leader1 (SEQ ID NO:12), ANEB1224 (SEQ ID NO:13), BIOL3 (SEQ ID NO:14), and BIOL4 (SEQ ID NO:15).

Figure 13B:
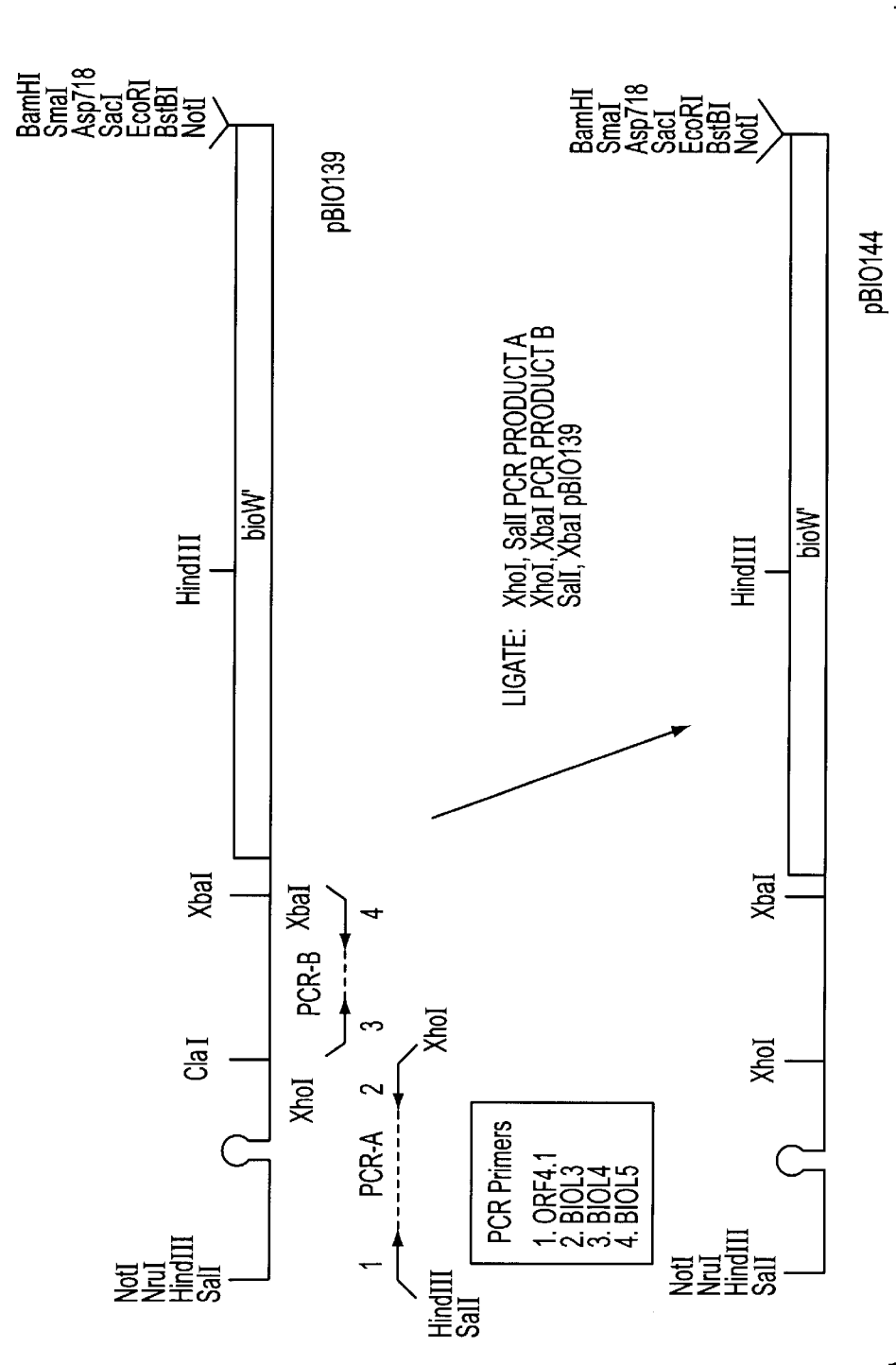

FIG. 13B is diagram of the construction of pBIO144.

FIG. 14 shows the DNA sequence of the *B. subtilis* biotin operon and its flanking sequences (SEQ ID NO:1).

Figure 15:
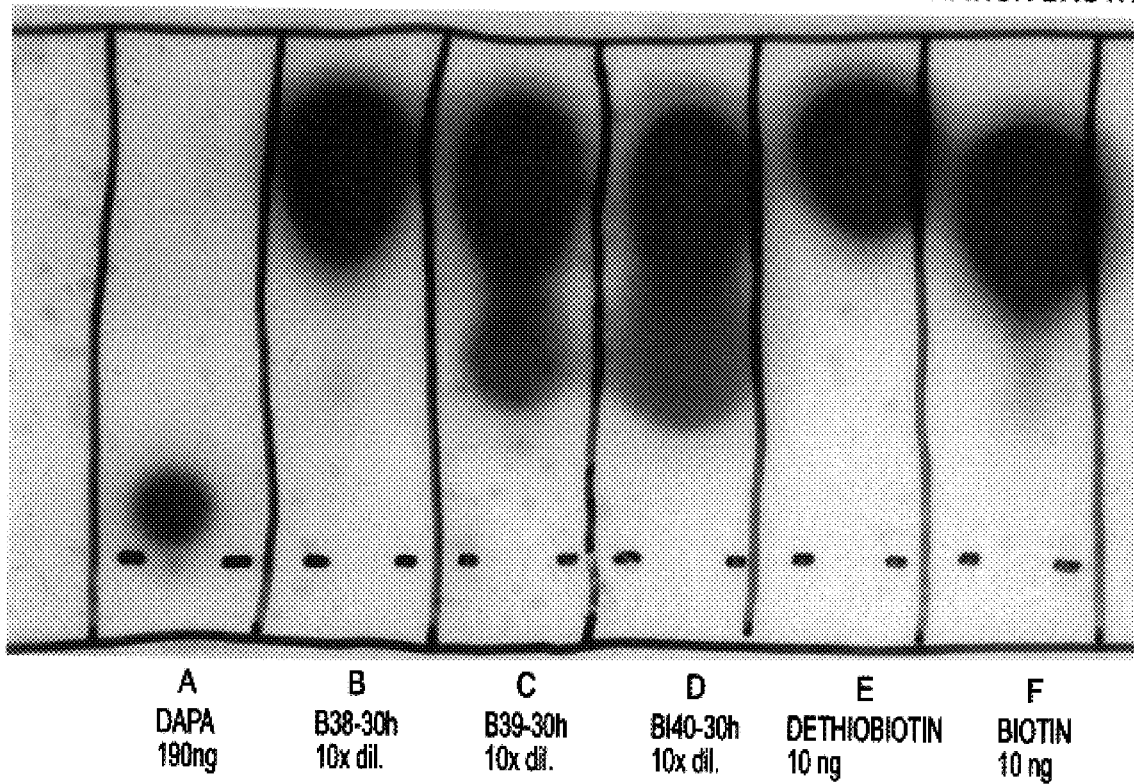

FIG. 15 shows the vitamer spectrum of various fermentation broths.

Figure 16A:
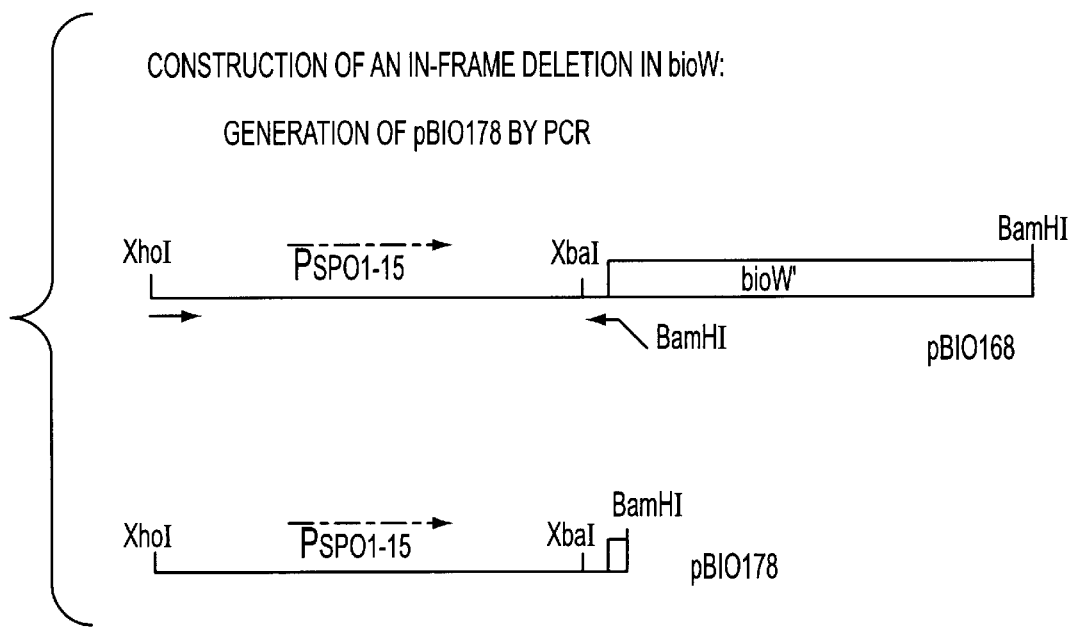
Figure 16B:
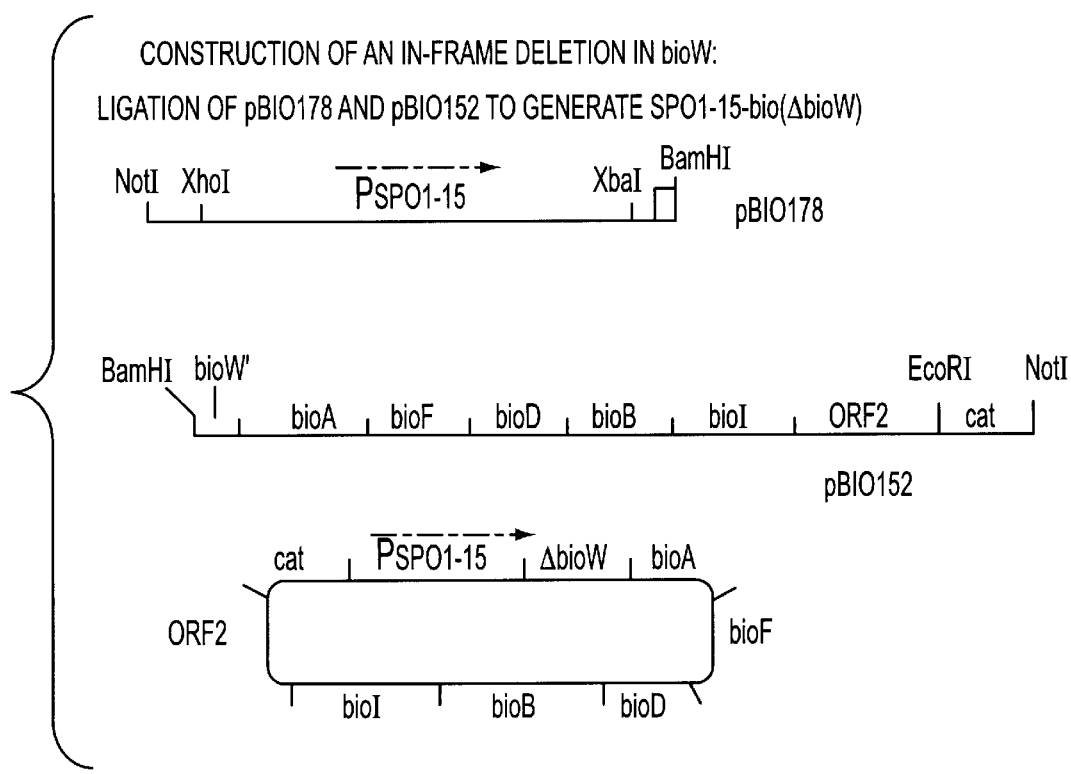

FIG. 16 is an illustration of an in-frame deletion in bioW.

FIG. 17A is an illustration of elements of the bioW catabolite repression sequence.

Figure 17B:
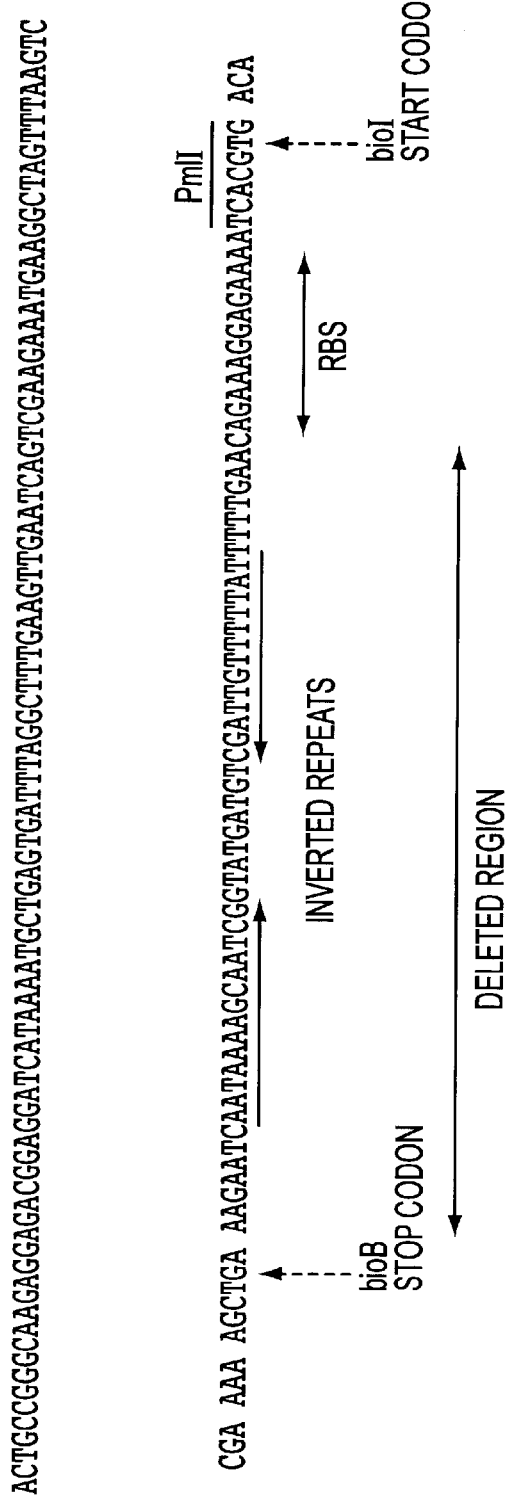

FIG. 17B is an illustration of the terminator region deleted between bioB and bioI.

Figure 18:
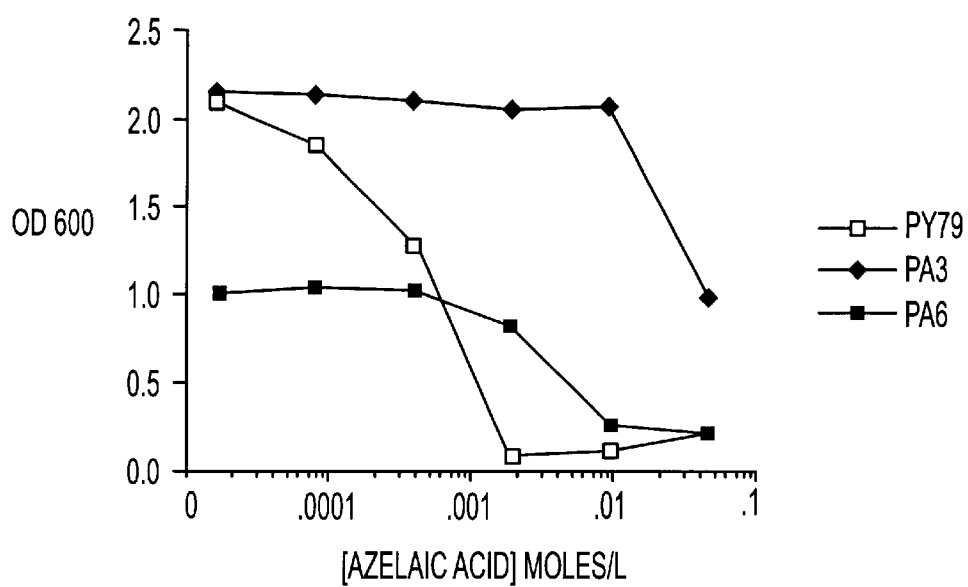

FIG. 18 is a graph showing the azelaic acid resistance of strains PA3 and PA6.

Figure 19:
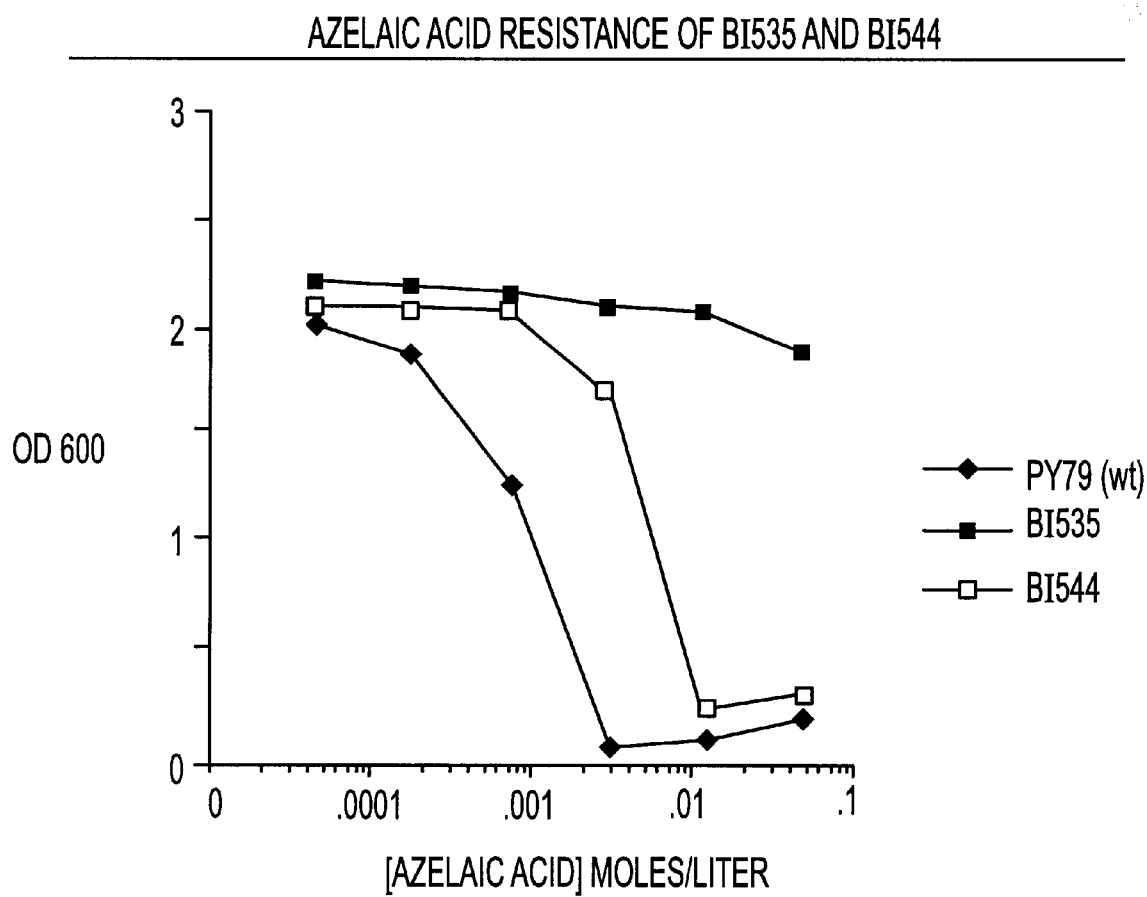

FIG. 19 is a graph showing the azelaic acid resistance of strains BI535 and BI544.

It is highly desirable to develop an efficient system for producing high titres of biotin that can be economically used in a commercial process. The present applicants have recognized that an improved system for biotin production can be developed using B. subtilis.

B. subtilis has several advantages over the use of other species. Unlike B. sphaericus, B. subtilis is highly characterized for the purposes of genetic engineering, increasing the ease by which one can a) develop a mutant strain optimized for biotin production; and b) manipulate and construct genetic vectors carrying genes encoding the biotin biosynthetic enzymes. Most importantly, applicants disclose herein that most or all of the genes encoding the biotin biosynthetic enzymes are found on a single operon. This makes it easier to generally regulate the expression of the operon, and to co-regulate the amount of each enzyme expressed. Furthermore, B. subtilis contains a unique cytochrome-450-like enzyme that is involved in vitamer production and can be manipulated to significantly enhance vitamer production. Neither the gene (bioI) encoding this enzyme nor any homologue of it from other organisms has been reported to play a role in biotin or biotin vitamer synthesis.

Obtaining the genes for the B. subtilis biotin operon was not a straightforward task. Preliminary attempts to identify the genes based on sequence similarity to B. sphadricus failed. The reason for the failure is that, despite their common taxonomic grouping as Bacillus, B. subtilis and B. sphaericus are quite divergent species (Stackebrant et al. supra). Consequently the sequence homology between the relevant B. sphaericus genes and corresponding B. subtilis genes was too low to permit cloning of the B. subtilis genes using the B. sphaericus genes as probes.

Applicants have therefore used an alternative and more successful strategy to clone the genes required for biotin biosynthesis (bio genes). This approach included complementation experiments with E. coli mutants in bioA, bioB, bioC, bioD, bioF, and bioH, and further characterization by marker-rescue and complementation experiments with known B. subtilis biotin mutants in bioA, bioB, and bioF (Pai et al. supra). These experiments showed that in B. subtilis all six of these biotin biosynthetic genes are contained on a single DNA fragment of approximately 8 kb. A detailed restriction map of this fragment has been obtained, and an analysis of overlapping clones, deletion mutants, subclones, and their respective nucleotide sequences allowed the genes to be located on the DNA fragment in the order, from right to left, bioW, bioA, bioF, bioD, bioB, bioI, and ORF2. All seven genes are transcribed in the same direction, compatible with their being part of a single operon.

The isolated biotin operon of B. subtilis was then inserted into a microbial host for the production of biotin. The operon and the microbial host can each be, or can separately be, deregulated for biotin production in order to provide a maximal level of biotin production.

Further embodiments are described in the following examples.

EXAMPLE I
Cloning the B. subtilis Genes for Biotin Biosynthesis

Applicants have cloned and characterized B. subtilis genes required for biotin biosynthesis (bio genes). Since prior to this work all that was known concerning B. subtilis bio genes was that mutations in bioA, bioB and bioF existed and were closely linked on the chromosome (Pai et al., supra), two different approaches were originally taken to clone these genes. The first approach involved testing of short (~45–60 bps) probes designed according to conserved sequences, and larger probes (~1 kb) generated by the polymerase chain reaction (PCR) from B. sphaericus bio genes. However, these probes failed to hybridize specifically to chromosomal digests of B. subtilis DNA. A second approach involved screening libraries of B. subtilis DNA for recombinant clones that complement E. coli bio mutants.

IA
Attempts to Clone the Bio Genes by DNA Hybridization With B. sphaericus Sequences To identify restriction fragments of B. subtilis that contained bio genes, short (~45–61 bps) probes to internal regions of the bioA, bioB, and bioF genes of B. sphaericus were prepared. The sequences of the probes were chosen based on conserved amino acids predicted from the bio DNA nucleotide sequences of E. coli and B. sphaericus.

The characteristics of these probes were as follows: bioA, 60-mer and bioB, 48-mer (nucleotides #1950–2009 and #3333–3380, respectively, from B. sphaericus sequence, GenBank™ accession #M29292); bioF. 45-mer (nucleotides #2877–2921 from B. sphaericus sequence, GenBank™ accession #M29291). Two of the probes did not hybridize (bioB probe) or hybridized poorly (bioF probes) to various chromosomal digests of B. subtilis DNA even when the stringency of the hybridization conditions was low (5×SSC, 10% formamide, 1×Denhardt's solution, 100 μg/ml single-stranded salmon sperm DNA, 37° C.). Only the bioA probe was able to hybridize. However, purified DNA fragments identified by bioA hybridization failed to marker-rescue the B. subtilis bioA mutant indicating that the fragments did not contain the bioA gene. Furthermore, the DNA hybrids were unstable; the probe could be washed off the filters under conditions of moderate stringency (0.25–0.1×SSC @ 37° C.). Similarly, larger DNA probes (~1 kb) of the three bio genes, which were prepared by PCR amplification of B. sphaericus chromosomal DNA, also failed to hybridize specifically with B. subtilis chromosomal DNA. Consequently these probes could not be used to screen gene banks for recombinant clones containing B. subtilis bio genes.

IB
Cloning the Bio Genes by Complementation of E. coli Mutants

Figure 6:
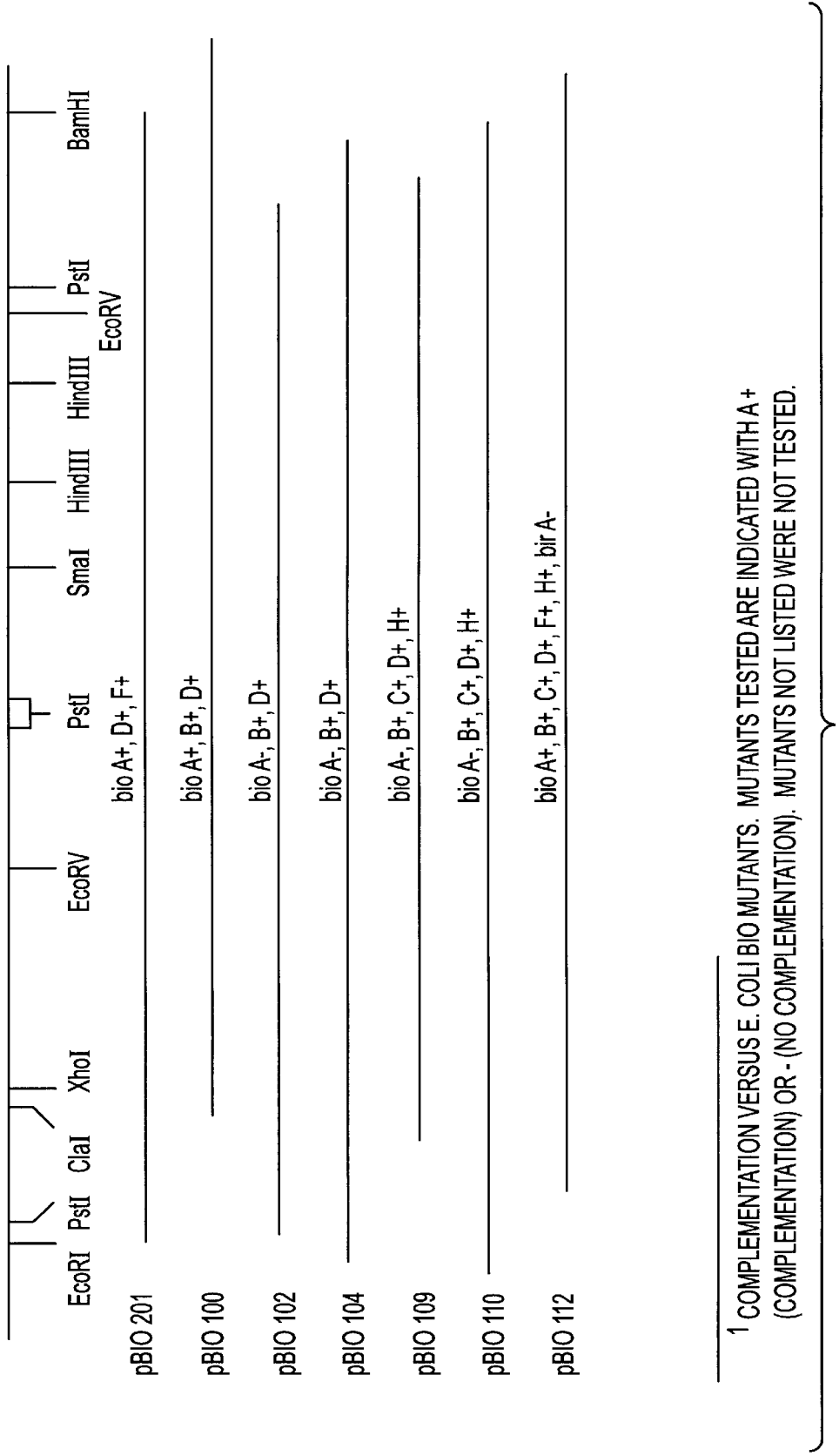
FIG. 6 shows the restriction enzyme sites and complementation results for pBIO plasmids.

A library of random B. subtilis fragments (~10 kb) was constructed in an E. coli vector using the positive selection vector pTR264 (Lauer et al., J. Bact. 173:5047–5053, 1991). pTR264 is a pBR322 derived vector carrying an ampicillin resistance gene and the λ repressor gene as well as the gene for tetracycline resistance under the control of the regulatory sequences subject to regulation by the λ repressor. pTR264 was constructed by reconstituting the ampicillin resistance gene of pTR262 by adding back the 5' end of the gene from the PstI site. An unique BclI site is located within the λ repressor gene. Insertion of DNA fragments into this site disrupts repressor function, thereby relieving repression of the tet gene. Clones with inserts are selected by plating transformants on tetracycline plates.

pTR264, isolated from a dam⁻ E. coli strain and digested with BclI, was ligated with B. subtilis chromosomal DNA which had been partially digested with Sau3A and fractionated on a sucrose gradient (8–12 Kb fragments). The library (labelled BSBI) contained Tet^r plasmids that complemented all the known E. coli bio point mutations. E. coli biotin mutants R879 (bioA24), R875 (bioB17), R878 (bioC23), R877 (bioD19), R872 (bioF3), and BM7086 (Δ-malA-bioH) (Cleary and Campbell, J. Bact. 112:830–839, 1972; Hatfield et al., *J. Bact.* 98:559–567, 1969) were transformed with the BSB1 library. Plasmids were isolated from each Bio⁺ transformant. Plasmids pBIO100 and pBIO101 were isolated by complementation of R879 (bioA); plasmids pBIO102 and pBIO103 by complementation of R877 (bioD); plasmid pBIO104 by complementation of R872 (bioF); plasmids pBIO109 and pBIO110 by complementation of BM7086 (bioH); and plasmids pBIO111 and pBIO112 by complementation of R878 (bioC) (FIG. 6). Finally, DNA from the BSB1 library was transformed into *E. coli* BM4062 [birA (ts)] (Barker and Campbell, *J. Med. Biol.* 146:469–492, 1981). Plasmids pBIO113 and pBIO114 were isolated from colonies that grew at 42° C.

Initial restriction analysis of the isolated plasmids indicated significant overlap of the cloned DNA fragments, suggesting that the five genes bioA, bioC, bioD, bioF and bioH are clustered in *B. subtilis* in a single operon. However, the birA complementing plasmids pBIO113 and pBIO114 did not overlap with the other five fragments.

IC
Restriction Mapping of the Bio Plasmids

A restriction map of the bio locus from unique EcoRI to BamHI sites is shown in FIG. 6. The EcoRI to BamHI fragment cloned into a derivative of pBR322 was called pBIO201. The detailed restriction map of the 9.9 kb fragment in pBIO201 was obtained by standard single and double enzyme digestion analysis.

pBIO100, the first clone of bio genes isolated by complementation in *E. coli*, extended an additional 300 bp beyond the BamHI site at one end. pBIO110, isolated by complementation of bioH mutants of *E. coli*, extended about 1100 base pairs beyond the EcoRI site at the other end. Southern hybridization studies indicated that the insert DNA of pBIO100 was derived from a single continuous segment of the *B. subtilis* chromosome.

ID
Complementation/marker Rescue of *B. subtilis* and *E. coli* Bio Mutants With PBIO Plasmids To confirm that the cloned DNA of pBIO100 contained *B. subtilis* bio genes, pBIO100 was tested for the ability to marker-rescue *B. subtilis* bio mutants. The plasmid restored biotin prototrophy to bioA, bioB, and bioF mutants at high frequency, indicating that the cloned DNA contained all or part of each of these *B. subtilis* bio genes.

The pBIO plasmids were also examined for their ability to complement *E. coli* bio mutants bioA, bioD, bioF, bioC and bioH. Most plasmids complemented more than one *E. coli* biotin mutation. The isolate pBIO112 complemented *E. coli* mutations in bioA, bioB, bioC, bioD, bioF and bioH (FIG. 6). pBIO112 did not complement the *E. coli* birA(ts) or the Δ(gal-uvrB) mutation. These data demonstrated that most of the known biotin genes are in a single cluster in *B. subtilis*.

Several deletions in pBIO201 were constructed by cutting at two mapped restriction sites, filling in overhangs if necessary, and ligating. After the structure of the deleted plasmids was confirmed, each was transformed into various *E. coli* bio mutants and complementation was scored. The results are summarized in FIG. 7. The deletion derivative pBIO203 was found to complement six of the known *E. coli* biotin genes (bioA, bioB, bioC, bioD, bioF, bioH), establishing that all six of the genes were located in the 8 kb fragment of DNA from BamHI to XhoI. The removal of 3.8 kb from the left of this fragment (pBIO204) eliminated the ability to complement bioC and bioH mutants. pBIO206 contained only the right most 2.5 kb of the biotin cluster and complemented only bioA and bioF mutants. The order based on these observations and hybridization data was bioC, bioH, (bioB, bioD), bioF, bioA.

IE
Cloning of a *B. subtilis* Fragment Containing a Complete BioW

DNA sequencing (see below) revealed that the promoter of the bio operon was not present on any of the originally cloned DNA fragments. However, this promoter region was recovered by chromosomal walking. None of the clones originally isolated by complementation of *E. coli* mutants had extended further to the right than had pBIO100. This was surprising since bioA sat at the rightmost end of these clones and fragments in the 8–10 kb range had been selected for cloning. However, DNA sequences of the rightmost end of the cloned insert of pBIO100 revealed about 300 bp of an open reading frame that was somewhat similar to *B. sphaericus* bioW. Fragments containing bioA and the adjacent upstream region were cloned in *E. coli* bioA cells containing a pcnB mutation to reduce plasmid copy number (Lopilato et al., *Mol. Gen. Genet.* 205:285–290, 1986). Under such conditions a PstI fragment containing an additional 2.7 kb of DNA upstream of bioA was cloned, and the location of the beginning of the bio operon was determining by DNA sequencing.

The pcnB mutation in *E. coli* results in low copy number maintenance of ColE1-derived plasmids, including pBR322 and pUC derivatives (Lopilato et al., 1986, supra). An *E. coli* strain, BI259, that contained both the bioA and pcnB mutations, was constructed. Restriction enzyme, deletion, and Southern analyses had shown that a 5.5 kb PstI fragment would contain a complete bioA gene. *B. subtilis* GP275 chromosomal DNA was digested with PstI and size fractionated by agarose gel electrophoresis. A pool of 4.4 to 6.6 kb fragments was ligated into a pBR322-derived plasmid and used to transform BI259. Selection was for ampicillin resistance and biotin prototrophy. A plasmid, pBIO116, was recovered that contained a 5.5 kb insert. This plasmid could transform BI259 to biotin prototrophy at high frequency but could not transform R879 (bioA, pcnB⁺) to either biotin prototrophy or ampicillin resistance. Southern hybridization with a probe (a 600 bp PstI-BamHI fragment of pBIO100) containing the 300 bp that was somewhat similar to *B. sphaericus* bioW was used to confirm that the cloned DNA contained the bioW homolog.

pBIO116 was available in very limited quantities from the pcnB background. The pcnB80 allele which was used in this cloning experiment is reported to reduce the copy-number of pBR322 replicons to about 6% of wild-type level (Lopilato et al., 1986, supra). To improve plasmid yields without impairing plasmid stability, the DNA was cloned in a low copy-number plasmid. The unique BamHI site within the 3' end of bioW was used to subclone a 3.0 kb BamHI-PstI fragment from pBIO116 into pCL1921. pCL1921 is a derivative of the low-copy number plasmid pSC101 that contains the lacZ'/polylinker cloning region of pUC19 and a selectable spectinomycin/streptomycin resistance gene (Lerner and Inouye, *Nuc. Acids. Res.* 18:4631, 1990). pCL1921 has a copy number of about 5–10 copies per cell. Purified 3.0 kb BamHI-PstI DNA from pBIO116 was ligated to BamHI and Pst-cut pCL1921 DNA and the ligated DNA was transformed into a pcnB⁺ *E. coli* strain, MM294, selecting for spectinomycin-resistance (100 μg/ml). A plasmid, pBIO350, was recovered that contained the correct 3.0 kb BamHI-PstI fragment. The quantity of pBIO350 recovered from this strain was significantly higher, without loss of plasmid stability, compared to pBIO116 isolated form the pcnB80 strain.

EXAMPLE II
DNA Sequencing of the B. subtilis Bio Gene Cluster

To further identify the bio biosynthetic genes, to understand the regulatory apparatus controlling their expression, and to locate sites appropriate for genetic engineering, the B. subtilis bio genes contained on clones pBIO100 and pBIO350 were sequenced using the Sanger dideoxy sequencing method using Sequenase™ kits, version 2.0 (United States Biochemicals, Cleveland, Ohio) as instructed by the manufacturer.

IIA
DNA Sequencing Strategy

The strategy used to obtain the DNA sequence of the 8–10 kb region that included the B. subtilis bio genes was to divide the region into four plasmid subclones of approximately equal size, and then make nested sets of deletions progressing through each subclone. To generate the nested deletions the "exonuclease III—endonuclease S1" method was used; the reagents were purchased in a kit (Promega, Madison, Wis.; instructions included). Nested deletions were made from both ends for three of the subclones and from one end for the fourth. Sequencing both sets of nested deletions for three of the subclones gave the sequence of both strands of each subclone, which is necessary to obtain a completely accurate sequence. For pBIO350 one strand was determined similarly and the opposite strand was determined by synthesizing sequencing primers at intervals of approximately 150 bp. The junctions between non-overlapping subclones were confirmed by sequencing from synthetic primers using pBIO201 or pBIO100 (or subclones thereof) as a template. The sequences were aligned and compared with the DNASTAR computer program (DNASTAR, Inc., Madison, Wis.).

Figure 1:
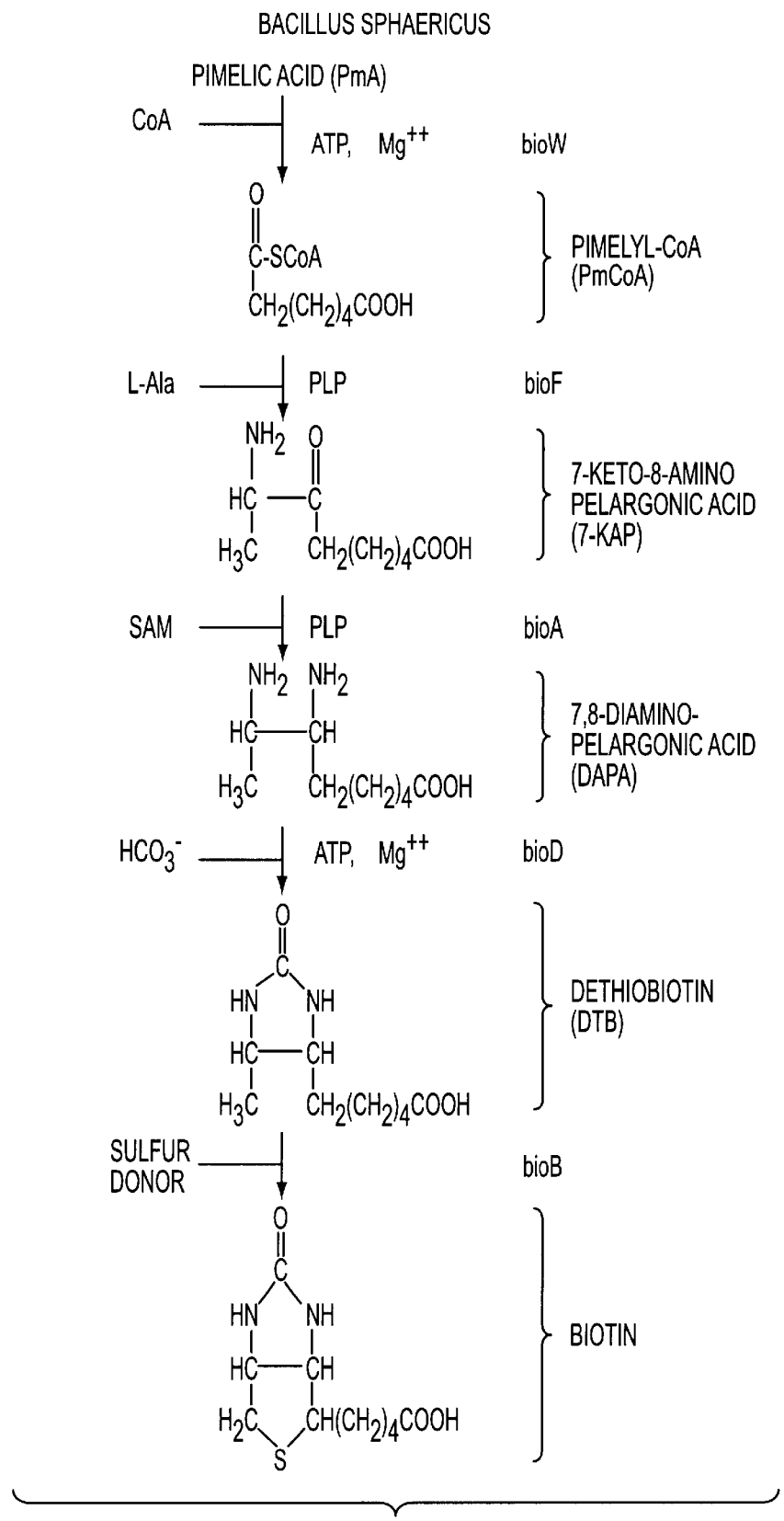
FIG. 1 is a schematic illustration of the biotin synthesis pathway of *B. sphaericus*.
Figure 2:
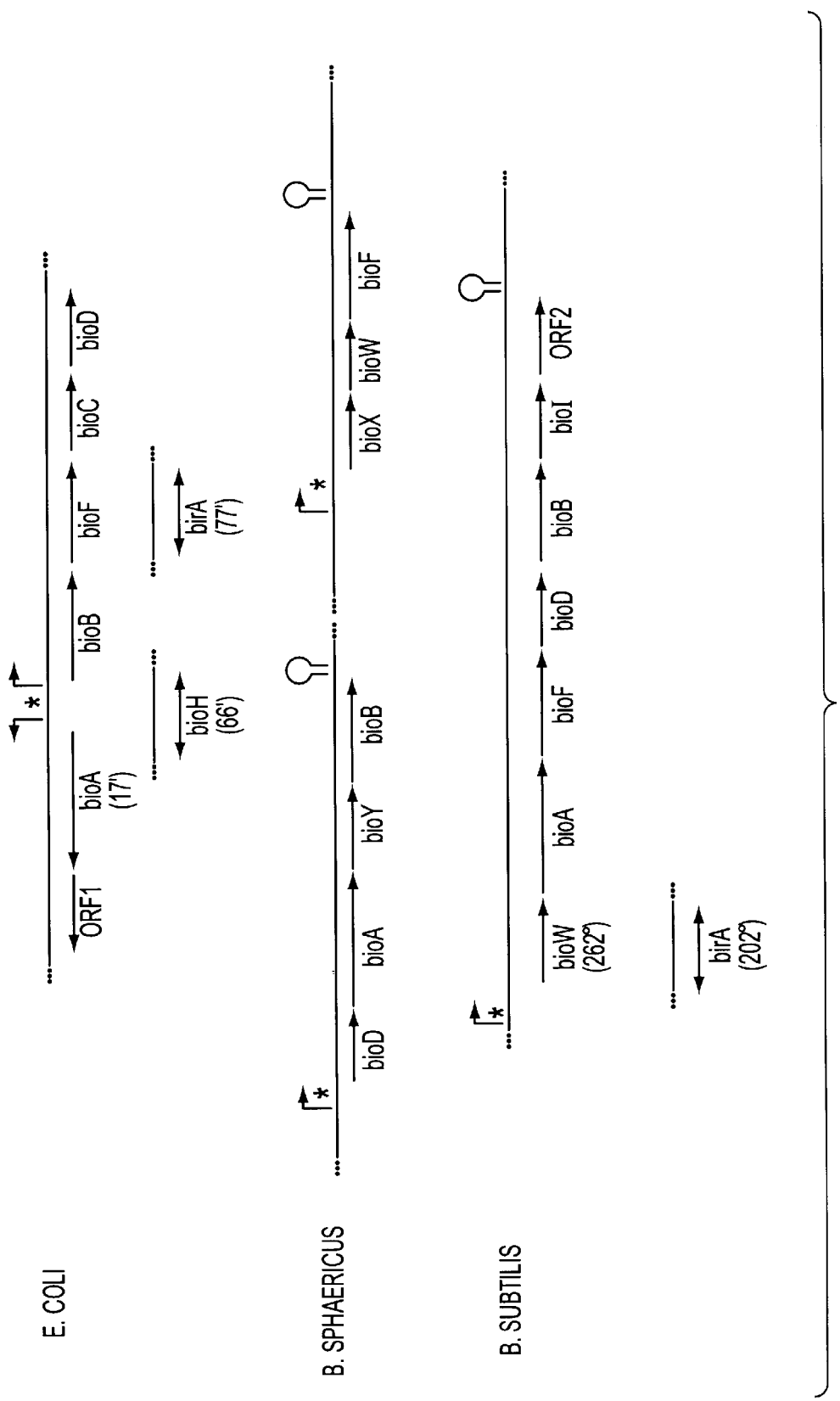
FIG. 2 is a schematic illustration of the organization of the biotin genes in *E. coli*, *B. sphaericus*, and *B. subtilis*.
Figure 3:
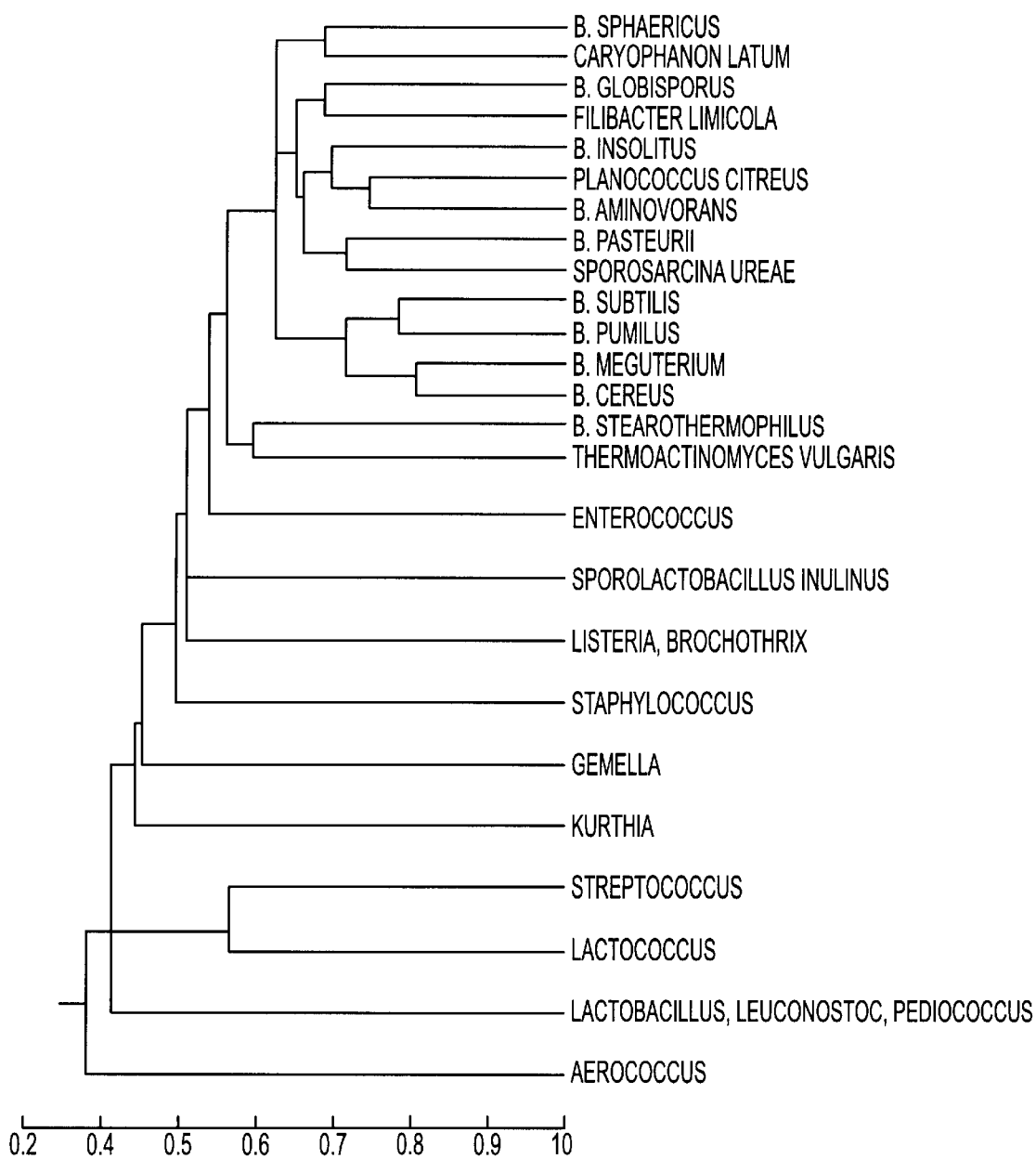
FIG. 3 is a schematic illustration of phylogenetic incoherency including the genus Bacillus.
Figure 5A:
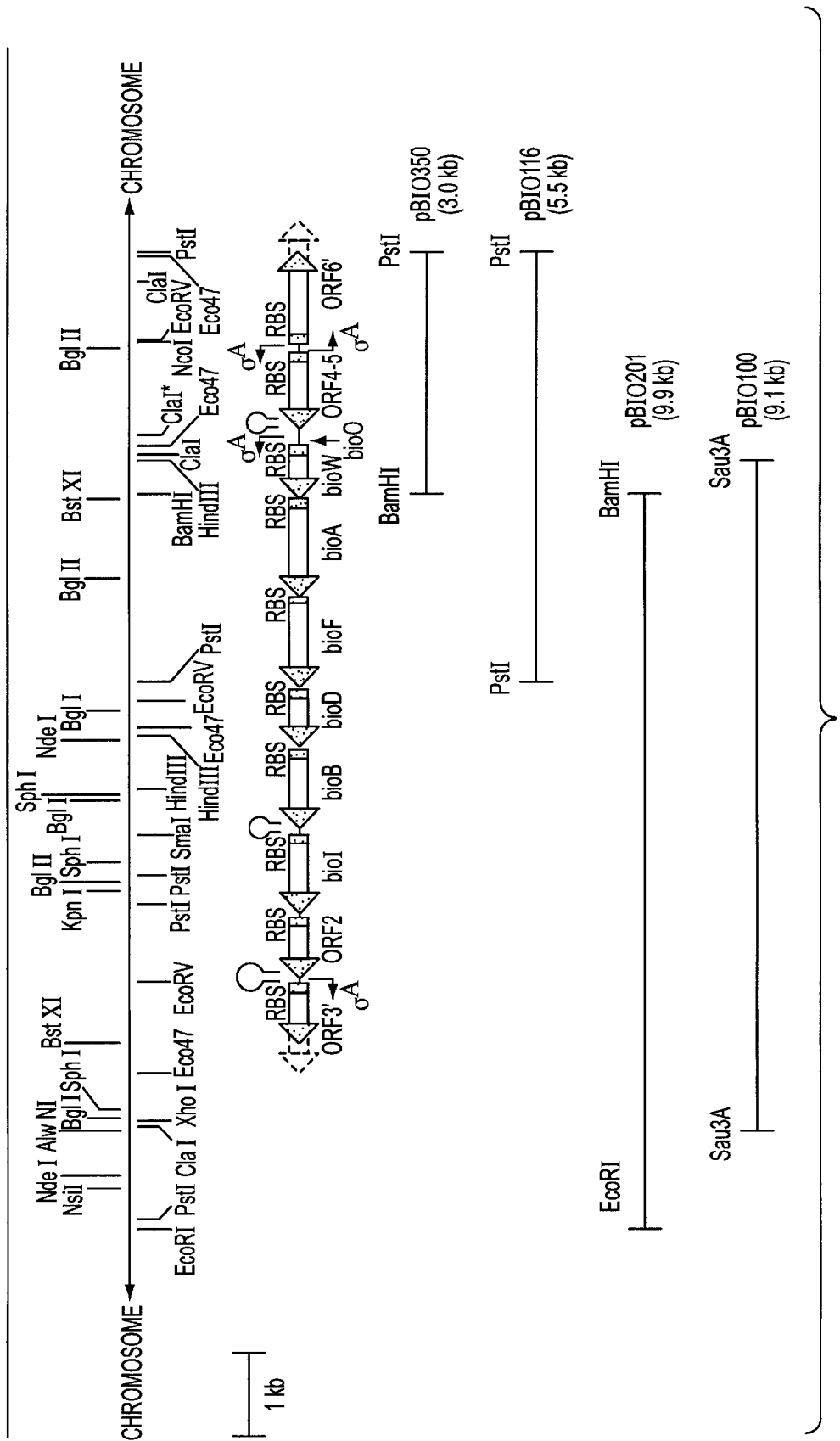
FIG. 5A is a physical map of the *B. subtilis* biotin operon.
Figure 5B:
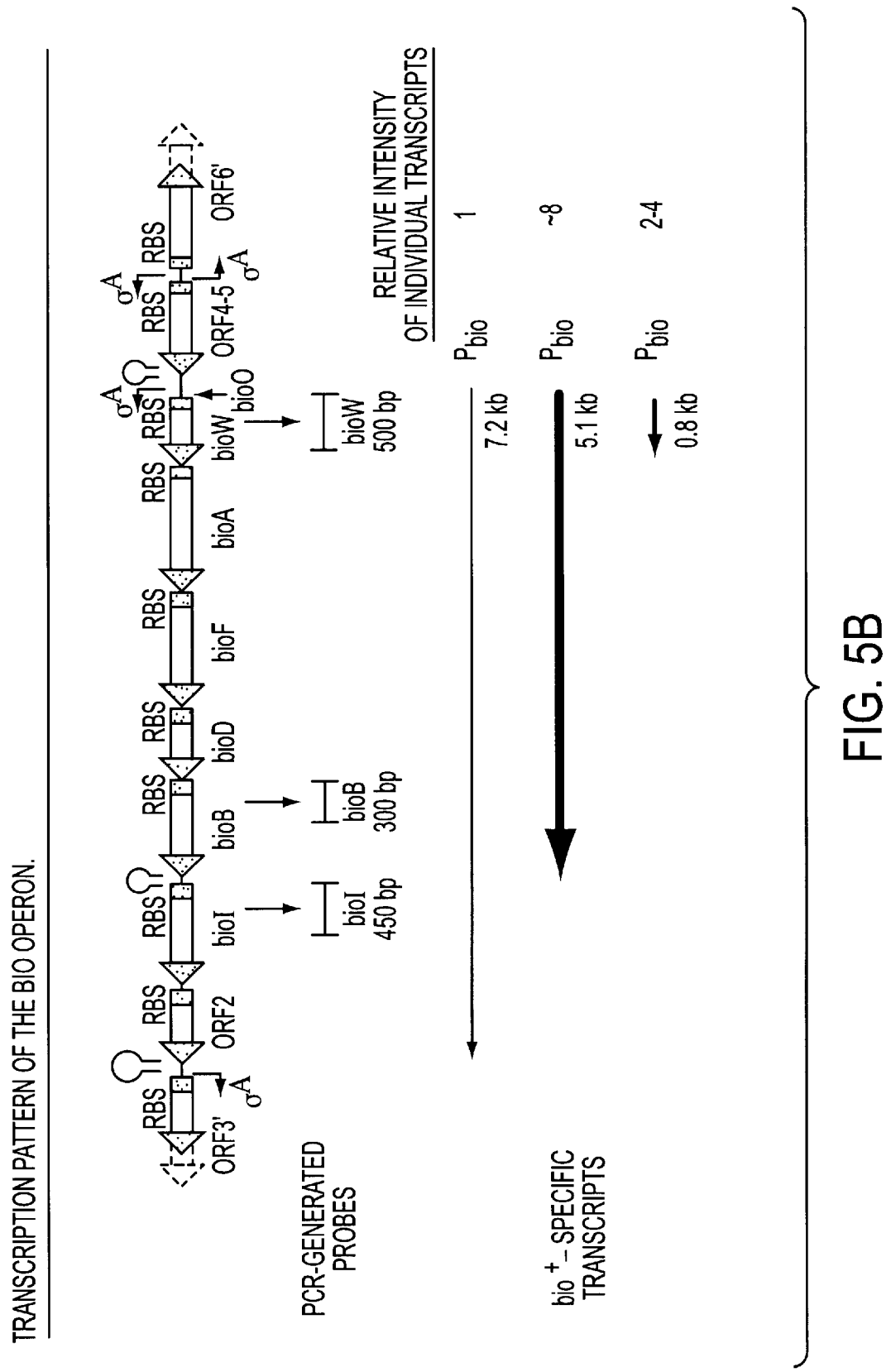
FIG. 5B is a map showing transcription of the *B. subtilis* biotin operon.

IIB
Identification and Organization of Bio-specific Coding Regions and Transcriptional Regulatory Signals Analysis of ~8500 bp of the DNA sequence from pBIO100 and pBIO350 indicated a single bio operon containing seven coding regions (FIG. 5A, FIG. 14, and SEQ ID NO:1). Starting at the 5' end of the bio operon in pBIO350 and continuing through pBIO100, one finds first a ~100 bp region which contains a putative promoter sequence recognized by the vegetative form ($\sigma^A$) of B. subtilis RNA polymerase (referred to as $P_{bio}$) next to a transcription regulator site that is defined by a strong sequence homology to the "operator" sites of the B. sphaericus bio operons.

The nucleotide sequence of this putative promoter region is shown in FIG. 4. [FIG. 4 symbols are as follows. Dashed lines: regions of dyad symmetry; Bold underline: similarity to the B. sphaericus bioDAYB regulatory site; $\sigma^A$: promoter region recognized by the vegetative form of B. subtilis RNA polymerase; RBS: ribosome binding site; *: restriction site blocked by dam methylation. Deduced amino acid sequences are shown below the nucleotide sequence.] The sequence of $P_{bio}$ is TTGACA—17 bp—TATATT (SEQ ID NO:2) and is in good agreement with the B. subtilis $\sigma^A$ consensus sequence, TTGACA—17/18 bp—TATAAT (SEQ ID NO:3). This region is immediately followed by an ORF (open reading frame) with homology to bioW (259 amino acids), followed by ORFs with homology to bioA (448 amino acids), bioF (389 amino acids), bioD (231 amino acids), and bioB (335 amino acids). The next two open-reading frames ORF1 (bioI; 395 amino acids) and ORF2 (253 amino acids) showed no sequence similarity to any known bio gene (FIG. 5A). The positions of the promoter, genes and putative transcription termination sites are summarized in Table 1.

TABLE 1

Summary of Genes, Promoters, and Regulatory Elements in the B. subtilis biotin operon.
(Refer to SEQ ID NO:1 and Fig. 14 for numbering of bases)

| Gene or Element | | Starting Base | Ending Base | Comments |
|---|---|---|---|---|
| σA promoter | | 324 | 352 | $P_{bio}$ |
| Potential Regulatory Site | | 355 | 387 | homology to B. sphaericus bio operator site |
| bioW | | 439 | 1218 | ATG start |
| bioA | | 1208 | 2554 | ATG start |
| bioF | | 2544 | 3713 | TTG start |
| bioD | | 3710 | 4405 | TTG start |
| bioB | | 4408 | 5415 | ATG start |
| bioI | | 5484 | 6671 | GTG start |
| orf2 | | 6748 | 7509 | GTG start |
| orf3 | | 7695 | — | GTG start |
| rho-independent termination sites | upstream from 5' promoter | 249 | 291 | |
| | between bioB and bioI | 5423 | 5462 | |
| | At 3' end of bio operon | 7501 | 7543 | |

Figure 8:
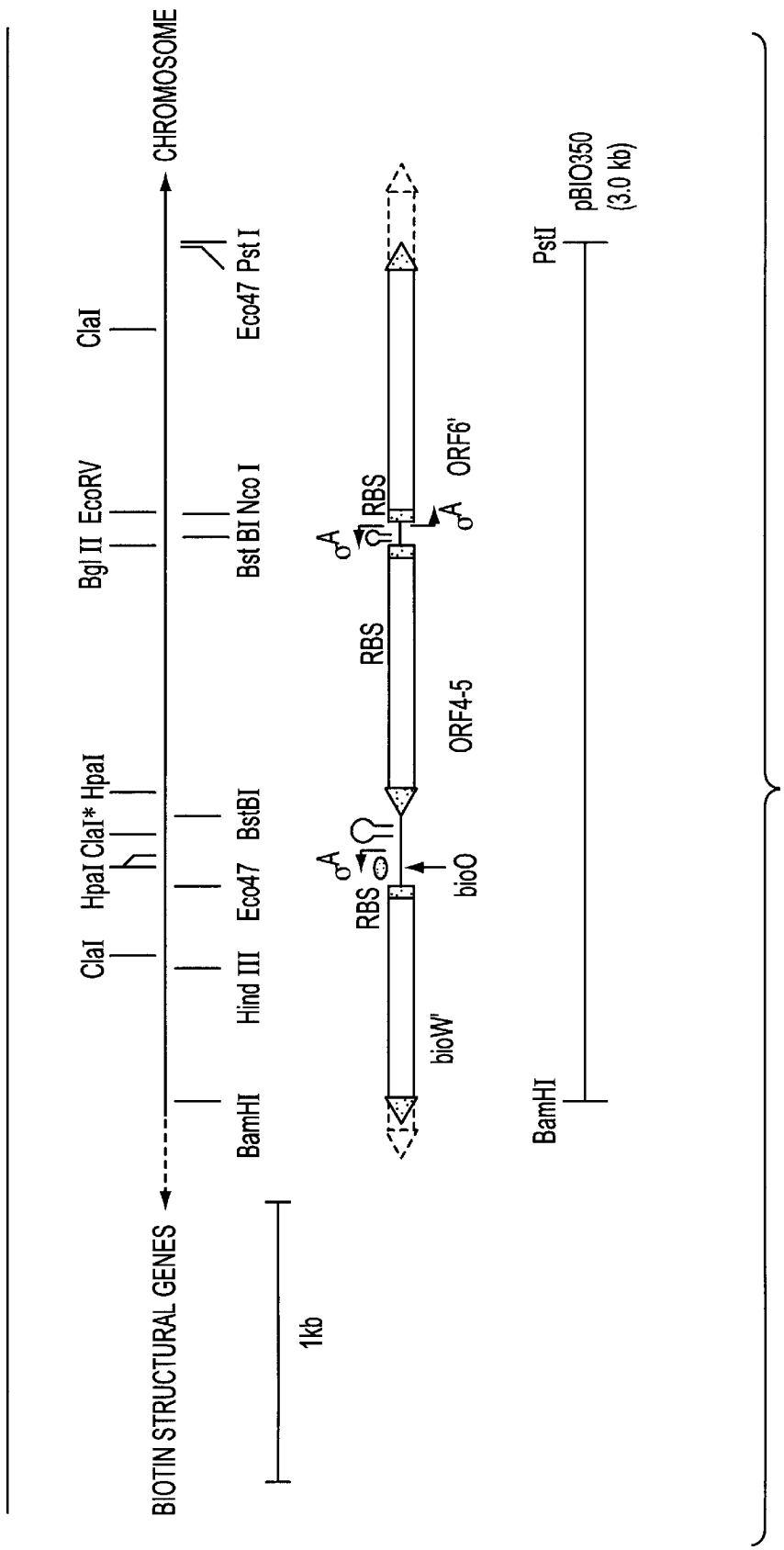
FIG. 8 is a physical map of the *B. subtilis* bio promoter region.

The location and orientation of promoters, transcriptional termination sites, and ribosome binding sites, are indicative of a single operon containing the bio genes. Each gene is preceded by a strong Bacillus ribosome binding site (RBS), with calculated ΔG's ranging from −11.6 to −20.4 kcal/mol. All genes are oriented in the same transcriptional direction (right to left). In addition, the 5' ends of bioA, bioF, bioD, and bioB overlapped the 3' ends of each preceding gene suggesting that expression of these genes is regulated, in part, by translational coupling. bioI and ORF2 are separated from the previous gene by 68 and 67 base pair intercistronic regions, respectively, indicating that they are not translationally coupled. The bioW gene appears to be the first gene in the operon as it is preceded by the potential RNA polymerase ($\sigma^A$) promoter site and putative operator site discussed above. This promoter region represents the beginning of the bio operon, since approximately 50 bp upstream from is a stem-loop structure that resembles a rho-independent transcripton termination site. This putative termination site represents the end of a separate transcription unit since it is in turn preceded by a coding region with a strong Bacillus ribosome binding site (RBS; ΔG=−14.8 kcal/mol) labeled ORF4-5 (299 amino acids), which is oriented in the same direction as the bio operon (FIG. 8). Finally, further upstream from ORF4-5, oriented in the opposite direction, there is a strong Bacillus RBS (ΔG=−17.4 kcal/mol) followed by the first 266 amino acids of another open reading frame, ORF6; the remainder of ORF6 continues beyond the PstI site. The deduced amino acid sequence of ORF6 showed significant similarity to a number of regulatory proteins related to the lacI repressor: E. coli ebgR (a repressor of a cryptic operon of unknown function); E. coli purR (a repressor of the purine nucleotide biosynthetic operon); and E. coli cytR (a pleiotrophic transcriptional repressor of deoCABD, udp, and cdd encoding catabolizing enzymes and nupc, nupG, and tsx encoding transport and pore-forming proteins). Transcription of ORF4-5 and ORF6 may be coordinated since we detect two overlapping $\sigma^A$ promoter sequences within the 175 bp gap between the 5' ends of ORF4-5 and ORF6 (TTGTAA—18 bp—TAATAT (SEQ ID NO:4)→ORF6; TTGATA—17 bp—AAAAGT (SEQ ID NO:5)→ORF4-5) and a series of inverted repeats.

ORF2 is the last gene in the bio operon based on the presence of a stable stem-loop structure resembling a rho-independent transcription termination site immediately at the end of this coding region. A second stem-loop structure with terminator-like features was identified in the intercistronic region between bioB and bioI. Several secondary structures of the mRNA are possible, with the most favored structure having a ΔG of formation of −11 kcal/mol and the least favored structure a ΔG of −5.6 kcal/mol.

Downstream from the end of the biotin operon is a strong RBS (ΔG=−20.0 kcal/mol) and 260 amino acids of another coding region, ORF3. The remainder of ORF3 continues beyond the BstXI site which marks the end of the sequenced region. The deduced amino acid sequence of ORF3 showed significant similarity to a number of *E. coli* membrane-associated transport proteins: glycerol-3-phosphate permease (ugpE and ugpA); maltose permease (malG and malF); and molybdenum permease (chl). In particular, the partial ORF3 peptide contains a 20 amino acid sequence at the COOH-terminal region found common to all membrane-associated transport proteins. ORF3 is transcribed separately from the bio operon using a putative $\sigma^A$ promoter sequence generated fragments were each cloned into three plasmids with different copy number; the low copy number plasmid pCL1921, a medium copy number plasmid, pJGP44 (which is derived from pBR322), and the high copy number plasmid, pUC19. In two of these recombinant plasmids expression of bioI and ORF2 is under the control of the lac promoter (pCR1921 and pUC19).

Plasmids containing bioI complemented both *E. coli* BM7086 (ΔbioH) and *E. coli* R878 (bioC). Plasmids containing ORF2 did not give normal complementation of either *E. coli* BM7086 or R878. It was clear from these experiments that the product of the bioI of *B. subtilis* is able to supply an activity needed for biotin synthesis that can substitute for, or overcome, the activity missing in either bioC or bioH mutants of *E. coli*.

A plasmid (pBIO403) containing only the *B. subtilis* bioW gene and its promoter cloned into pCL1921 (Lerner and Inouye, 1990, supra), complemented both *E. coli* ΔbioH and bioC mutants, if and only if pimelic acid was added to the medium at aboaut 30 mg/l. This experiment confirmed that bioW encodes a pimelyl-CoA synthetase that can bypass bioH and bioC in *E. coli*.

TABLE 2

Enzymes, genes, and ribosome binding sites of biotin biosynthesis in *B. subtilis*.

| | Gene | RBS ΔG (kcal/mol) | Predicted start codon | Enzyme or Function | Estimated no. of amino acids | Estimated $M_r$ | Estimated percent amino acid identity to corr. gene from: | | |
|---|---|---|---|---|---|---|---|---|---|
| | | | | | | | *E. coli* | *B. sph.* | other |
| Biotin biosynthetic operon (map position 262°) | bioW | −11.8 | ATG | Pimelyl-CoA synthetase | 259 | 29,633 | | 44 | |
| | bioA | −15.8 | ATG | DAPA aminotransferase | 448 | 50,118 | 34 | 44 | |
| | bioF | −11.6 | TTG | 7-KAP synthetase | 389 | 42,567 | 35 | 50 | |
| | bioD | −18.6 | TTG | DTB synthetase | 231 | 25,114 | 32 | 28 | |
| | bioB | −12.2 | ATG | Biotin synthetase | 335 | 36,931 | 34 | 71 | 22[a] |
| | bioI | −18.4 | GTG | Cytochrome P-450 | 395 | 44,838 | | | 30[b] 33[c] |
| | ORF2 | −17.6 | GTG | β-ketoreductase | 253 | 28,204 | | | 23[d] |
| Downstream gene | ORF3 | −20.0 | GTG | Unknown membrane-associated transport protein | >258 | >28,600 | 25[e] 23[f] | | |
| Upstream genes | ORF4–5 | −14.8 | ATG | Unknown | 299 | 33,780 | | | |
| | ORF6 | −17.4 | ATG | Unknown regulatory protein | >266 | >29,200 | 29[g] 27[h] 27[i] | | |

[a]identity to *E. coli* lipA.
[b]identity to *Bacillus magaterium* cytochrome P-45$_{BM-1}$.
[c]identity to *Saccharapolyspora erythraea* eryF.
[d]identity to *Saccharapolyspora erythraea* eryAII.
[e]identity to *E. coli* malG.
[f]identity to *E. coli* ugpE.
[g]identity to *E. coli* ebgR
[h]identity to *E. coli* purR
[i]identity to *E. coli* cytR TAGACA-$N_{18}$-TACATT (SEQ ID NO:1; FIG. 14, #7600–7629) 95 bps upstream of ORF3.

The gene-enzyme relationships, the enzyme sizes, and percent homology to the same enzyme from other organisms are summarized in Table 2.

Complementation studies using plasmid subclones that contained either bioI or ORF2 alone under the transcriptional control of the lac promoter indicate that bioI alone is sufficient to complement either a bioC or bioH mutation of *E. coli*. Copies of bioI and ORF2 were generated by PCR. A HindIII site was introduced at the 5' end of each gene, a BamHI site was introduced at the 3' end of bioI and an Asp718I site was introduced at the 3' end of ORF2. The PCR No significant similarity was detected between the deduced amino acid sequence of either *B. subtilis* bioI or ORF2 and the protein sequences of *E. coli* bioC or bioH genes or other bio genes. Subsequent comparison to the protein database of GenBank™, however, indicated significant similarity of bioI to a number of cytochrome P-450 enzymes from *B. megaterium* (BM-1), *S. erythraea* (eryF and eryK), *S. griseolus* (suaC and subC), S. species strain SA-COO (choP), and other organisms. Cytochrome P-450s are a class of enzymes that include monooxygenases that are known to catalyze hydroxylation of many different kinds of substrates, including fatty acids. Since synthesis of pimelic acid, a precursor to biotin, might involve hydroxylation and/or further oxidation of an unidentified fatty acid, bioI may be involved in an early step in biotin synthesis. The bioC and/or bioH genes are functionally equivalent to bioI, based on the ability of bioI to complement bioC and/or bioH mutations. Similar comparative studies revealed weak similarity of ORF2 to the β-ketoreductase domain of polyketide synthase II (ery AII), which is involved in an early enzymatic step in erythromycin formation.

EXAMPLE III
Cat Insertional Mutagenesis of the Bio Operon and Flanking Coding Regions To verify the boundaries of the bio operon predicted from the nucleotide sequence and to confirm the role of previously unidentified bio genes, a cat cassette was used to construct insertions or deletions in: bioW, bioI, ORF2, the bio promoter region, ORF3, ORF4-5, and ORF6 (located outside the predicted boundaries of the bio operon). The cat cassette includes a chloramphenicol resistance gene. To make the above-mentioned constructions, plasmid derivatives containing these mutations were first constructed in E. coli. The cat insertions were then transferred to the bio chromosomal locus of B. subtilis by DNA transformation using standard procedures. To determine whether the insertions or deletions inactivated biotin synthesis, colonies containing these mutations were assessed for growth on biotin-free medium agar plates with or without the presence of biotin (Bio phenotype).

Figure 9:
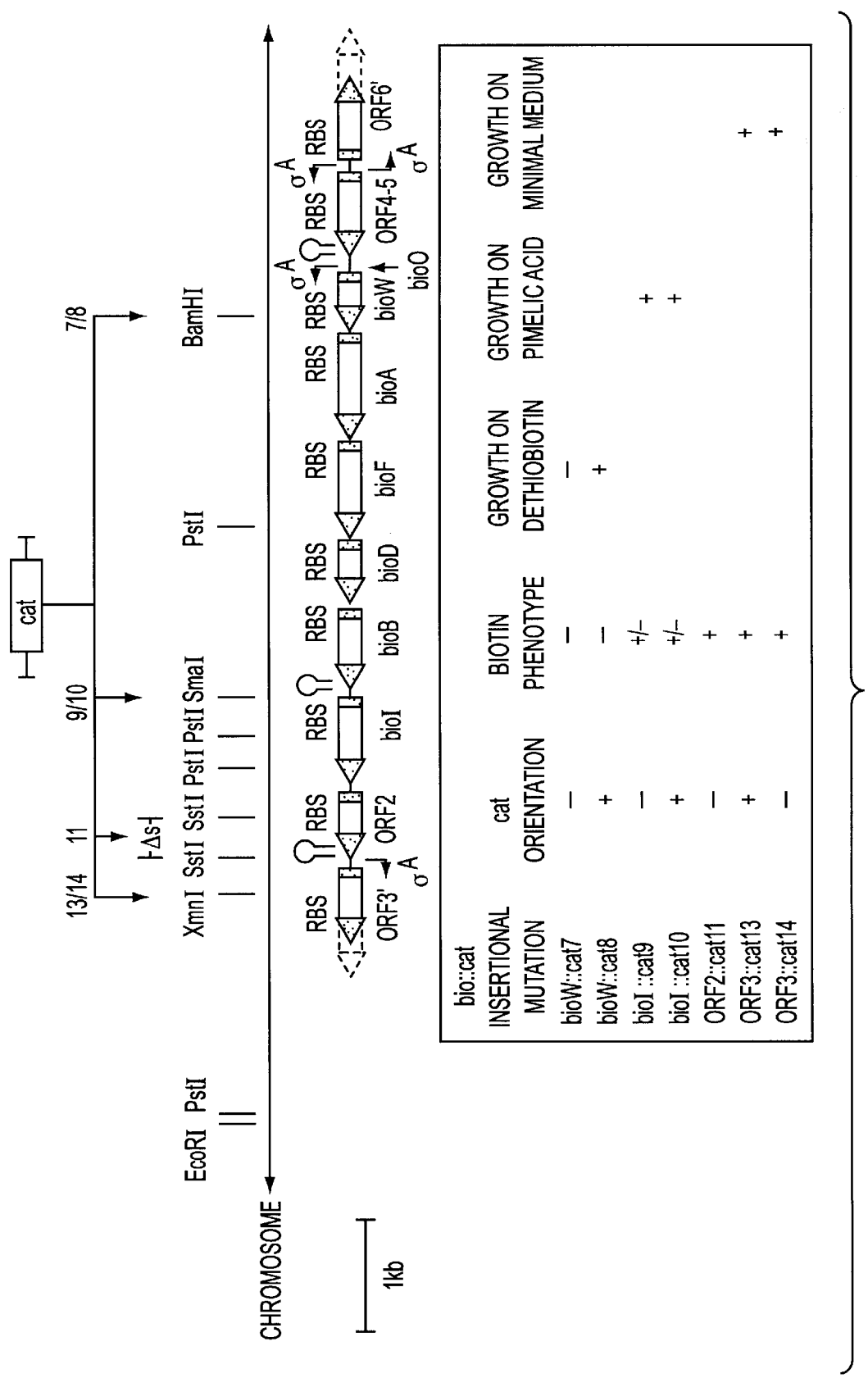
FIG. 9 shows the location and Bio phenotype of cat (chloramphenicol-acetyl transferase) insertional mutations within *B. subtilis* bioW, ORF2, and ORF3.
Figure 10:
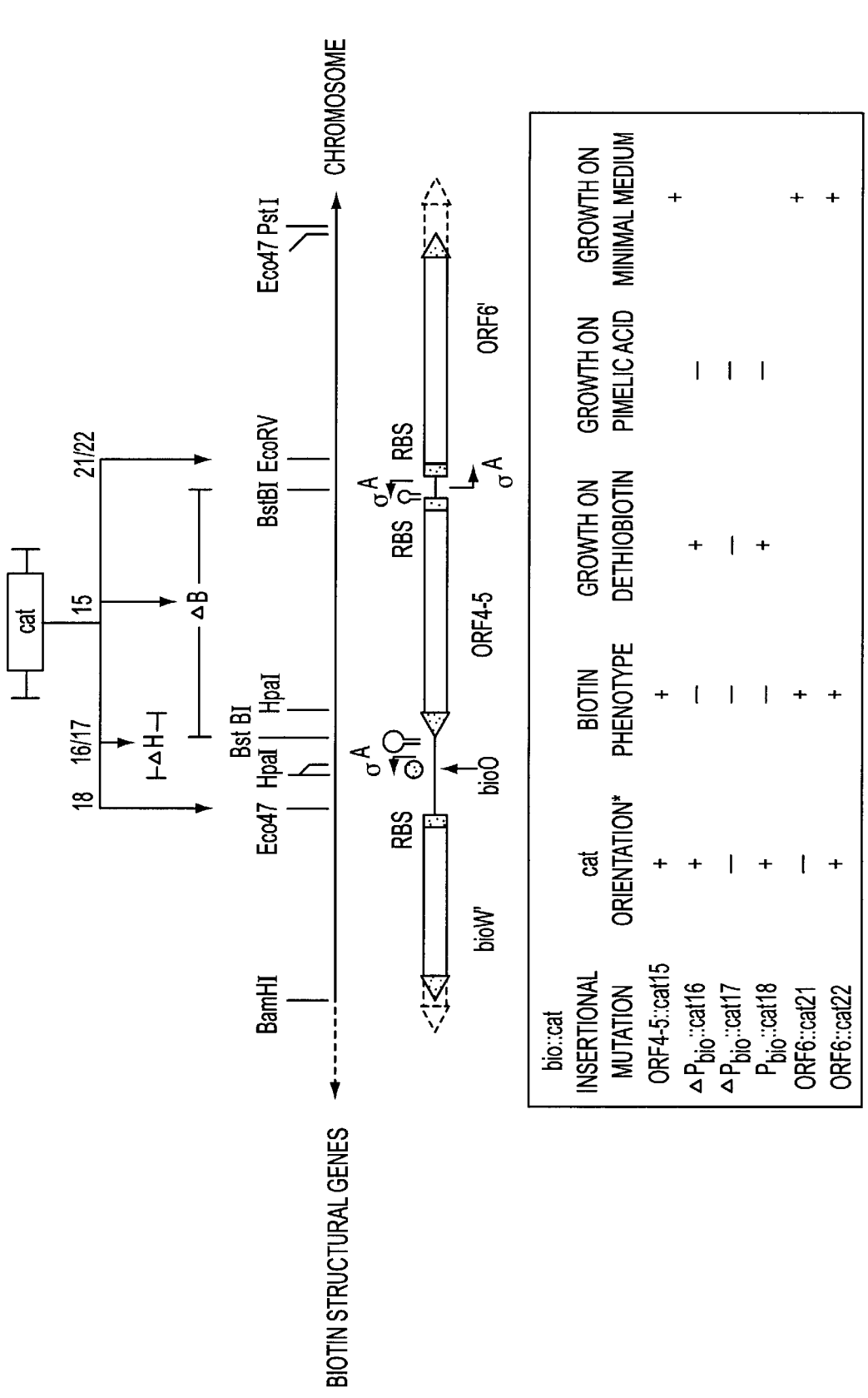
FIG. 10 shows the location and Bio phenotype of cat insertional mutations within *B. subtilis* bio promoter region, ORF4-5, and ORF6.

As diagrammed in the top of FIG. 9 and FIG. 10, the cat cassette was inserted by ligation: into the coding regions of bioW using a BamHI site; into bioI using a SmaI site; into ORF3 using a XmnI site; into ORF6 using an EcoRV site; between the pair of SstI sites deleting the 3' end of ORF2; or between the pair of BstBI sites deleting ORF4-5. The cat cassette was also used to either disrupt the bio promoter region by ligating it into the Eco47III site, or used to entirely replace this promoter region by ligating it between the HpaI sites. In each of the ORF2/SstI, ORF4/BstBI, and /Eco47III constructions, the cat gene was inserted only in the same direction as the disrupted coding region or promoter region. In all other constructions, two different plasmid derivatives were generated where the cat cassette was inserted in either possible orientation. Each of these mutations was then integrated into the bio locus by first linearizing the cat-containing plasmid by a restriction enzyme cut outside of the bio DNA and transforming this cut DNA into a competent prototrophic B. subtilis strain, PY79, and selecting for chloramphenicol-resistance (Cm$^r$). The Bio phenotype of each mutant is summarized at the bottom of FIG. 9 and FIG. 10. Insertions within the coding regions located outside of the predicted bio operon, ORF3, ORF4-5 and ORF6, generated Cm$^r$ prototrophic colonies, indicating that these mutations had no phenotype with respect to biotin production and with respect to auxotrophy. Insertions within the bio operon gave complex results that generally supported the nucleotide sequence data. Interruption of the bio promoter region with the cat gene oriented in the opposite direction relative to the biotin operon, and interruption of bioW with the cat gene oriented in either direction relative to the bio operon, generated an unambiguous Bio$^-$ phenotype, confirming the location of these sequences at the 5' end of the bio operon/promoter region. However, replacement of the $P_{bio}$ promoter region with the cat gene inserted in the same transcriptional direction as the biotin operon generated Bio$^+$ bacteria at a low frequency (0.1%). Bioassay experiments indicated that bacterial biotin vitamer production was increased in the presence of low concentrations of chloramphenacol, suggesting that transcription of the biotin operon was under the control of the cat promoter. The 3' end of the operon could not be definitively identified by this genetic method. Insertions within bioI resulted in Cm$^r$ colonies that were partially deficient in biotin production, i.e., grew poorly on biotin-free medium but grew to wild-type levels in the presence of biotin (33 µg/ml), whereas the ORF2::cat mutation generated Bio$^+$ colonies. These results suggested that bioI is not absolutely required for biotin production, and the ORF2 gene product appeared to be dispensable for wild-type growth in the absence of exogenous biotin. No significant effect on biotin production was detected in a birA strain (e.g., BI421; see Example XB) containing the ORF2::cat$_{11}$ mutation. Nevertheless, it is still possible that ORF2 may be required for overproduction of biotin.

The partial biotin-deficient phenotype generated by the bioI::cat mutation, designated as Bio$^\pm$, appeared to be caused by inactivation of bioI rather than by a polar effect because mutations within the downstream genes ORF2 or ORF3 were Bio$^+$. To determine whether the Bio$^\pm$ phenotype was genuine and to verify that the bioI gene product was involved in formation of pimelic acid, the bioI::cat mutation was by-passed by feeding pimelic acid. As summarized in FIG. 9, strains of PY79 containing this mutation in either orientation of the cat gene grew to wild-type levels on biotin-free medium containing pimelic acid (33 µg/ml). These results confirm that the bioI gene product is involved in early biotin formation and that inactivation of this product only partially disrupts biotin production.

EXAMPLE IV
Analysis of the Regulatory Mechanism of the Biotin Operon

Transcription of the divergent E. coli bio operon bio-ABFCD is regulated by a classical repressor/operator mechanism, involving a repressor encoded by the birA locus (Cronan, Cell 58:427–429, 1989). This repressor is a bifunctional molecule carrying the holoenzyme synthetase activity at its COOH-terminal end, an activity which converts biotin into biotinoyl-AMP, an adenylated form of biotin, before transferring it to the apocarboxylase enzyme. Biotinoyl-AMP also functions as the co-repressor, the repressor/biotinoyl-AMP complex blocking transcription by binding to an operator site that overlaps the -10 regions of two divergent promoters.

Figure 11:
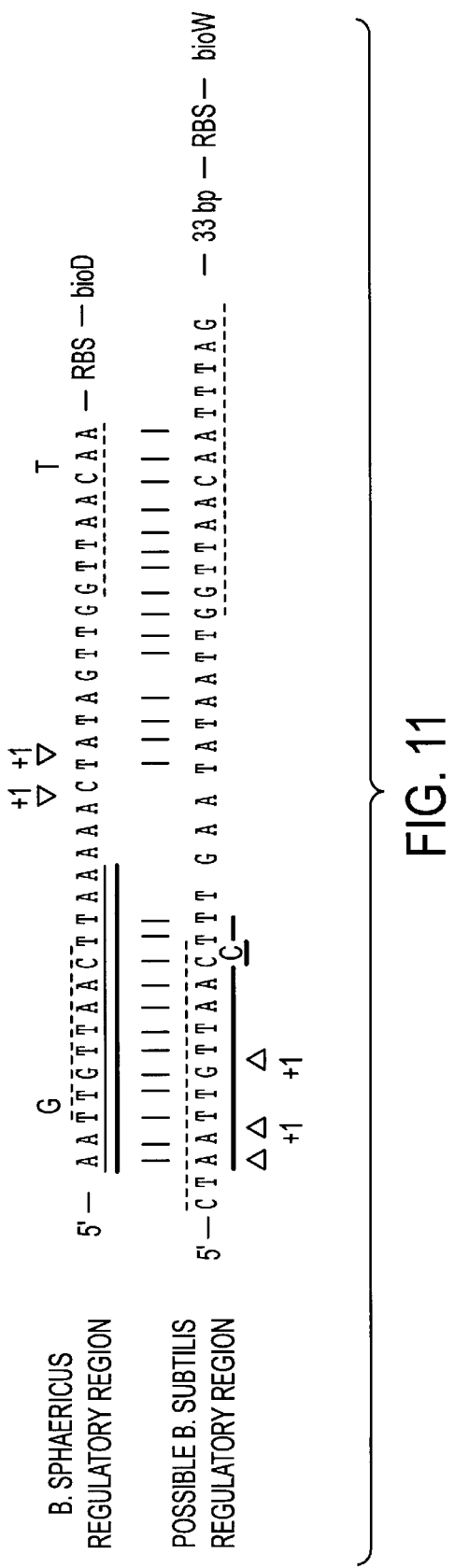
FIG. 11 is a comparison of the nucleotide sequences of the *B. sphaericus* bioDAYB regulatory region (SEQ ID NO:8) and the *B. subtilis* bio promoter region (SEQ ID NO:9).

The 5' promoter and regulatory region of the wildtype bio operon was characterized in order to replace it with one of several strong and constitutive B. subtilis promoters (see Example VII). The most likely site for initiation of transcription of the B. subtilis bio operon is a σ$^A$ promoter, $P_{bio}$, approximately 84 bp upstream from bioW, the first gene in the operon (FIG. 4). The actual mRNA start site is either one of the two adenosine nucleotides, 3–4 bp downstream from the end of the "TATATT" box, or the guanosine 7 bp from the "TATATT" box. The RNA leader sequence contains a 33 bp segment with strong sequence homology to the "operator" sites of the B. sphaericus bio operons. Comparison of the nucleotide sequences of this region to the 5' non-coding region of the B. sphaericus bioDAYB operon is shown in FIG. 11. [FIG. 11 symbols are as follows. Upper sequence (B. sphaericus bioDAYB regulatory region) 15 bp regulatory region: double bold underline; region of dyad symmetry: dashed line; start site of transcription determined by primer extension mapping: arrows; ribosome binding site: RBS; The "G" and "T" nucleotides were displaced to facilitate sequence alignment. Lower sequence (B. subtilis bio promoter region) 13 bp putative regulatory region based on similarity to the B. sphaericus regulatory region in the upper sequence: single bold underline; putative start sites of transcription: arrows; ribosome binding site: RBS; The "C" nucleotide was displaced to facilitate sequence alignment.]

The majority of conserved nucleotides are clustered at two sites (13 and 11 bp) separated by a 9 bp segment. This finding suggests that transcription of the B. subtilis bio genes is regulated by a repressor/operator mechanism, possibly involving a birA-like gene located near the trp operon (see Example IX). The activity and regulation of a promoter upstream of bioW has been verified by showing that a translational lacZ fusion to bioW, which included $P_{bio}$ and the putative regulatory region, displays biotin-regulated expression of β-galactosidase (see Example V).

The 5' RNA leader contains a potential large stable stem-loop structure (ΔG=−14.0 kcal/mol) that overlaps the oeprator region.

Based on the identification of $P_{bio}$ and a regulatory site upstream from bioW, the B. subtilis bio genes are transcribed as a single polycistronic message of approximately 7200 bp. In addition, there also exists possible secondary promoter sites located within the internal regions of the bio operon. For example, a sequence, TTGAAA—17 bp—TCTTAT (SEQ ID NO:6 and FIG. 14, #6258 to 6286), with some similarity to a consensus $\sigma^A$ promoter sequence, is located within bioI (approximately 775 bp downstream from the start codon of bioI). Determination of whether these sequences function as internal promoters can be achieved by using restriction fragments from internal portions of the bio operon to construct translational lacZ fusions (see Example V). Optimization of biotin production can be achieved by modifying one or more of the primary or secondary promoters.

IVA
Construction and Analysis of Bio-lacZ Translational Fusions

A translational lacz fusion was constructed to confirm the activity and regulation of the putative promoter and regulatory region, and to assess the relative level of expression of the B. subtilis biotin operon in a variety of contexts. This was accomplished by inserting a 3.1 kb BamHI-BglII fragment containing a promoter-less lacZ coding region into the BamHI site of pBIO350, to give pBIO397 and pBIO398. These two presumably identical plasmids contain an in frame "translational" fusion between bioW and lacZ on a low copy number plasmid. pBIO397 and pBIO398 turn a lacZ⁻ E. coli pale blue on X-gal indicator plates, suggesting that the fusion is expressed at a relatively low level in E. coli.

To test the bioW-lacZ fusion for biotin-regulated expression in B. subtilis, Bio⁺ partial diploids were constructed. The cat cassette was cloned into pBIO397 using the single SmaI site located within the polylinker region downstream from the lacZ gene. One recombinant plasmid, pBIO397cat, with the cat gene oriented in the same direction as the translational fusion, was used to generate Bio⁺ partial diploids. Competent cells of the prototrophic B. subtilis strain PY79 were transformed with pBIO397cat plasmid DNA selecting for Cm$^r$. Transformants should only arise by recombination into the chromosome. This leaves an intact copy of the bio operon, allowing activity of the lac fusion to be assessed in the absence of added biotin.

The promoter of the BamHI to PstI fragment cloned in pBIO350 is regulated by biotin. Two Cm$^r$ Bio⁺ partial diploids containing the bioW-lacZ fusion were tested for β-galactosidase activity in biotin-free medium in the presence or absence of biotin (100 μg/liter). In liquid ONPG assays, both strains were regulated specifically by biotin. The level of β-galactosidase was repressed in the presence of biotin and induced in its absence to 24 to 85-fold higher specific activity (Table 3). This strain with the bioW::lacZ fusion integrated at the bio operon has also been used to isolate new biotin analog-resistant mutants (see below) on X-gal indicator plates.

TABLE 3

Biotin-regulated expression of bioW-lacZ translational fusion.

| Strain | OD$_{600}$ | β-galactosidase activity (Miller Units)[a] | | Fold Increase |
|---|---|---|---|---|
| | | +Biotin (100 μg/l) | −Biotin | |
| PY79 (bioW-lacZ) 12A | Late Log (0.7–0.8) | 0.47 | 11.30 | 24 |
| | Stationary (1.1–1.4) | 0.17 | 11.00 | 65 |
| | Late Stationary (1.4–1.6) | 0.13 | 6.85 | 53 |
| PY79 (bioW-lacZ) 14A | Late Log (0.7–0.8) | 0.64 | 21.10 | 33 |
| | Stationary (1.1–1.4) | 0.15 | 12.30 | 82 |
| | Late Stationary (1.4–1.6) | 0.10 | 8.45 | 85 |
| PY79 (SPβ::bioW-lacZ)/#1 | (1.04–1.08) | 0.04 | 0.60 | 15 |
| PY79 (SPβ::bioW-lacZ)/#3 | (0.988–0.960) | 0.06 | 0.49 | 9 |
| BI421 (SPβ::bioW-lacZ)/#1 | (1.00–0.936) | 0.67 | 1.00 | 1.5 |
| BI421 (SPβ::bioW-lacZ)/#3 | (1.07–0.92) | 0.96 | 0.86 | 0.9 |
| α-DB9 (SPβ::bioW-lacZ)/#1 | (0.892–0.528) | 0.18 | 1.65 | 9.2 |
| α-DB9 (SPβ::bioW-lacZ)/#3 | (1.344–1.200) | 0.11 | 1.35 | 12.3 |
| HB3 (SPβ::bioW-lacZ)/#1 | (1.068–1.076) | 0.24 | 0.32 | 1.3 |
| HB3 (SPβ::bioW-lacZ)/#3 | (1.213–1.320) | 0.18 | 0.15 | 0.8 |

[a]Average of two measurements, expect for α-DB9 (SPβ::bioW-lacZ)/#1 (one measurement).

IVB
Construction and Analysis of an SPβ-borne BioW-lacZ Translational Fusion Other strains, in addition to the lacZ fusion strain of Example IVA, can be constructed for deciphering biotin regulatory mechanisms. For example, Applicants recognized that insertion of the plasmid-borne bioW-lacZ fusion into the chromosome causes technical problems because the integrated plasmid amplifies in copy number. Thus the expression of the bioW-lacZ fusion at single copy-number and at a site distinct from the bio operon was tested by introducing the fusion into a modified SPβ specialized transducing phage (see, e.g., Zuber et al., J. Bacteriol. 169:2223–2230, 1987, hereby incorporated by reference).

Two isolates of PY79 (SPβ::bioW-lacZ) and BI421 (SPβ::bioW-lacZ) were assayed for β-galactosidase activity as described above. The results are summarized in Table 3.

In the Bio⁺ strain PY79, expression of SPβ::bioW-lacZ was very low, but showed biotin-specific regulation. β-galactosidase was repressed in the presence of biotin and induced approximately 9–15 fold in the absence of biotin. Comparison to earlier assays of PY79 containing two or more copies of the plasmid-borne bioW-lacZ fusion indicated that the single-copy fusion produced three-fold less β-galacactosidase under repressed growth conditions and about 20-fold less under derepressed growth conditions. In a B. subtilis birA strain (BI421; see Example XB) low-level constitutive expression of the fusion was observed. The levels of β-galactosidase in the birA strain were only slightly higher than the level observed in PY79 (SPβ::bioW-lacZ)

grown under derepressed growth conditions. In one of the BI421 (SPβ::bioW-lacZ) isolates biotin was slightly repressed β-galactosidase expression, suggesting that this birA mutation may not completely relieve biotin regulation of the fusion. These results confirmed that expression of bioW from is regulated by biotin.

Biotin regulation was also examined in two independently isolated biotin analog-resistant mutants. HB3 contains a spontaneous birA mutation and α-DB9 contains an α-dehydrobiotin resistant mutation unlinked to either bio or birA. These strains were transduced, grown, and assayed as described above, except that α-DB9 (SPβ::bioW-lacZ) was assayed during mid-exponential growth. As summarized in Table 3, the fusion-bearing HB3 strains displayed low-level constitutive lacZ expression. Unlike the birA mutants, however, α-DB9 (SPβ::bioW-lacZ) displayed biotin-regulated expression of lacZ.

EXAMPLE V
Secretion of Biotin and Biotin Vitamers From *E. coli* Strains Containing *B. subtilis* Bio Genes During complementation experiments, Applicants observed that an *E. coli* bioA mutant containing pBIO201 could cross-feed the same strain containing the control plasmid pBR322, demonstrating that biotin synthesized by the pBIO201 containing strain was secreted into the media and metabolized by the Bio⁻ strain. Applicants therefore tested various newly constructed plasmids for the ability to secrete biotin and biotin vitamers into the media.

*E. coli* strains MM294 and JM109 lacI$^Q$ (both strains are wild-type for bio genes) were transformed with pBR322, pBIO201, pUC19, and pBIO289 (described in Example VI, below). The pBR322 and pBIO201 transformants were grown in minimal medium containing 2% glucose. The pUC19 and pBIO289 transformants were grown in a rich medium containing 2% glycerol since they did not grow well in liquid minimal medium. After 48 hours, cells were removed by centrifugation and any residual live cells were killed with chloroform. Supernatants were diluted serially in ten-fold diluted Difco Biotin Assay Medium supplemented with 0.5% glucose and 5 mg/l thiamine, and tested for support of growth of *E. coli* Δ(mal-bioH) and *E. coli* Δ(bioA-D), described below. Standard curves were prepared from serial dilutions of biotin and desthiobiotin. The assay was sensitive to 1 μg/liter.

The results from these assays are shown in Table 4. Strains containing plasmids encoding *B. subtilis* bio genes secreted biotin, while strains containing control plasmids did not secrete biotin. This demonstrated that the *E. coli* strains containing the *B. subtilis* biotin operon (pBIO289) are capable of secreting enhanced levels of biotin and biotin precursors.

TABLE 4

Production of biotin and biotin vitamers* from *E. coli* strains containing *B. subtilis* bio genes.

| Strain | Plasmid | Biotin (μg/l) | Total Biotin and Biotin Vitamers (μg/l)* |
|---|---|---|---|
| MM294 | pBR322 | 0 | 3 |
|  | pBIO201 | 10 | 10 |
| JM109 | pUC19 | 0 | 0 |
|  | pBIO289 | 10 | 10 |
| MM294 | pUC19 | 0 | 1 |
|  | pBIO289 | 10 | 100 |

*Biotin vitamers are given as desthiobiotin equivalents.

This assay can also be used to test the level of biotin, or biotin precursor, produced by other strains, e.g., *B. subtilus* strains, or other plasmids. Candidate strains are tested after being transformed with a plasmid bearing a functional biotin operon. Alternatively, candidate plasmids are tested in a strain known to secrete biotin.

EXAMPLE VI
Construction of a "Minimal" Bio Subclone

The minimal subclone encodes all of the relevant functions of the original primary clones (e.g., pBIO100 and pBIO201). A "minimal" subclone was constructed to confirm the location of the bio genes derived from deletion mapping and DNA sequence information, and to confirm that the open reading frame downstream from a transcription terminator to the right of an EcoRV site (see FIG. 5A) is not required for biotin biosynthesis.

An EcoRV (partial) to BamHI fragment from pBIO201 (containing all of the open reading frames thought to be bio genes except the bioW gene) was inserted into the SmaI to BamHI backbone of pUC9 (Viera and Messing, Gene 19:259–268, 1982) to construct pBIO289. Since the bio genes of pBIO289 are all downstream from the lac promoter of pUC9, and since pUC9 is maintained at a higher copy-number than pBR322 (the parent of pBIO100 and pBIO201), pBIO289 is expected to express the bio genes at a higher level than pBIO201 and pBIO100 in an *E. coli* host. pBIO100, 201, and 289, as well as pBR322 (as a control), were transformed into a series of isogenic *E. coli* bio mutants. Each transformant was tested for complementation on medium lacking biotin. The results are shown in Table 4. pBIO289 complemented all mutants that were defective in a single bio gene, confirming that all relevant genes lie upstream of the putative terminator. The open reading frame downstream from the terminator (ORF3) is not necessary for complementing any of the individual *E. coli* bio mutants.

TABLE 5

Complementation of various *E. coli* bio mutants by selected plasmids.

| | Plasmid | | | |
|---|---|---|---|---|
| Mutation | pBR322 | pBIO100 | pBIO201 | pBIO289 |
| none | +++ | +++ | +++ | +++ |
| Δ (gal-uvrB) | − | − | − | − |
| ΔbioA | − | + | ++ | +++ |
| bioB | − | +++ | +++ | +++ |
| bioC23 | − | +++ | +++ | +++ |
| ΔbioD | − | − | − | +++ |
| Δ (mal-bioH) | − | +++ | +++ | +++ |

EXAMPLE VII
Construction of Full Length Wild-type and Engineered *B. subtilis* Biotin Operons Experiments to construct engineered, full length bio operons for integration and amplification in the *B. subtilis* chromosome are described below.

VIIA
Re-construction of a Full Length Wild-type Bio Operon

Since it had proved necessary to clone the 5' end of the *B. subtilis* biotin operon at low copy number for work in *E. coli*, a low copy number plasmid was also used for construction of complete and engineered biotin operons for integration into the *B. subtilis* chromosome. As described above, the 5' end of the *B. subtilis* bio operon was cloned as a 3 kb PstI-BamHI fragment in pCL1921 (Lerner and Inouye, 1990, supra) a low copy number plasmid present at about 5–10 copies per cell, to give pBIO350.

A full length biotin operon was then reconstructed by adding the 3' portion of the bio operon from pBIO201 to pBIO350. A 10 kb BamHI to EcoRI fragment from pBIO201, that contains the majority of the biotin operon as well as about 3 kb of downstream DNA, was ligated into pBIO350 that had been gapped with BamHI and EcoRI. Two resulting plasmids that had the correct anticipated structure were called pBIO400 and pBIO401. pBIO401 complements all known E. coli bio mutants, including a ΔbioA-D mutant. When pBIO401 was selected by complementation in a ΔbioA-D strain and then produced in a rich medium, it was stable enough to yield usable quantities of plasmid DNA. Since the spectinomycin-resistance gene carried by pBIO401 is not expressed in B. subtilis, a cat cassette was added at the EcoRI site in pBIO401 to allow for selection, integration, and amplification in B. subtilis wild-type or deregulated strains by methods known to those skilled in the art, resulting in the plasmid pBIO401cat$_s$.

To determine the effect of increased bio copy-number on biotin production, pBIO401cat$_s$, which contained a single copy of the cat cassette (resistant to chloramphenicol at 5 μg/ml) and the entire bio operon, was integrated into the chromosomes of wild-type and biotin-deregulated strains of B. subtilis. The plasmid copy number was amplified by selection on 60 μg/ml chloramphenicol, and biotin production was thereby increased.

VIIB
Construction of Engineered Bio Operons

In constructing engineered, deregulated biotin operons for integration into the B. subtilis chromosome, it was useful to install unique restriction sites between transcriptional signals, regulatory sites and coding regions to allow easy introduction of alternate elements or alleles. Also, unique sites were used to flank the engineered biotin operon in these constructions, so as to remove E. coli-derived vector sequences prior to integration.

Applicants discovered that construction of an engineered B. subtilis bio operons with a strong, constitutive promoter was not a straight-forward task. It was not possible to maintain the entire B. subtilis biotin operon on a single plasmid in E. coli, even a low-copy plasmid, when the operon was transcribed by a strong constitutive promoter, e.g., the SP01-15 or SP01-26 promoter. An alternative and novel strategy had to be developed to introduce an amplifiable DNA fragment containing the entire engineered bio operon into the B. subtilis chromosome. First, for cloning and engineering purposes the operon was manipulated in two separate pieces: 5' and 3' cassettes. Next, when the DNA engineering was completed, the relevant DNA fragments from the appropriate 5' and 3' cassettes were ligated and the ligated cassettes were transformed directly into B. subtilis. The ligations were designed to deliver either circular or concatameric molecules that would recombine with homologous sequences in the chromosome thereby inserting the engineered DNA in a manner that could be amplified, with or without accompanying vector sequences.

Plasmids were constructed for use as backbone vectors for developing contructs that include an engineered bio operon. These plasmids were based on the low copy number vector pCL1920 (Lerner and Inouye, 1990, supra). The polylinker in pCL1920 was replaced with a polylinker flanked by NotI sites. The lac promoter present in pCL1920 was also removed for simplicity. The fragment containing the lac promoter and the polylinker was eliminated with EcoRI. The backbone, containing the pSC101 origin of replication and the omega fragment encoding resistance to spectinomycin, was re-circularized in the presence of a NotI linker to give pBIO121. Plasmid pJGP40 is a pBR322 derivative that contains a kanamycin resistance gene cloned into a polylinker flanked by NotI sites. The NotI fragment encoding kanamycin resistance from pJGP40 was cloned into the NotI site of pBIO121 to give pBIO124, the two orientations being indicated by "a" and "b" (FIG. 12). Digestion of both pBIO124 derivatives with Asp718I and religation eliminated the kanamycin resistance element, leaving a complete polylinker, to give plasmids pBIO126a and pBIO126b.

VII.Bi
Engineering a 5' Cassette

In considering which functional elements at the 5' end of the bio operon should be separated by unique restriction sites, the elements of most interest were 1) the putative stem-loop termination site upstream from the putative biotin promoter, 2) the putative promoter-operator-leader region, and 3) the ribosome binding site, initiation codon, and 5' coding region of bioW. Our strategy, as depicted in FIG. 12, was to introduce by PCR HindIII and SalI sites 70 bp upstream from the terminator, which is upstream from the biotin promoter. To separate the terminator from the promoter-operator region the ClaI site in this region was converted to a XhoI site. Conversion of the Eco47III site, which precedes the ribosome binding site of bioW, to an XbaI site separates the promoter-operator-leader region from the ribosome binding site-start codon fragment. A description of all the PCR primers used and their orientation is indicated in FIG. 13A. Table 6 lists the fragments generated by PCR. A three way ligation with 1) PCR fragment E which introduces a 5' HindIII-SalI site and converts the Eco47III site to a XbaI site, 2) PCR fragment B which converts the Eco47III site to a XbaI site and extends to the BamHI site in bioW and 3) a HindIII-BamHI digest of pBIO126A vector, resulted in plasmid pBIO139. A second three way ligation with PCR fragments C, D, and SalI and XbaI digested pBIO139 converted the ClaI site to a XhoI site and completed the initial construction as plasmid pBIO144. pBIO144 contains a modified wild-type 5' end of the bio operon with a unique XhoI site replacing the ClaI site upstream of the promoter/operator region and a unique XbaI site replacing the Eco47III site immediately downstream of this region (FIG. 13A. The expected DNA sequence of pBIO144 from the SalI site to the BamHI site was confirmed.

VIIBii
Engineered 3' Bio Cassettes

3'cassettes were constructed in pBIO126A, a low copy number plasmid with a NotI-flanked polylinker. To enable pBIO126A to be used as a vector for integration and amplification, a PCR fragment of the cat gene from pHW9 (Horinouchi and Weisblum, J. Bacteriol, 150:815–825 (19822)) was introduced at the BstBI site to give plasmid pBIO146A. The BamHI to EcoRI fragments from pBIO201 (Example IC) and pBIO289 (Example VI) were cloned into the polylinker of pBIO146A to give plasmids pBIO151 and pBIO152 respectively. The two plasmid vary in the amount of 3' flanking sequence accompanying the bio operon.

VIIC
Regulation of Engineered Bio Operons by a Constitutive Promoter

Different constitutive promoters, such as those from the SP01 bacteriophage, e.g., SP01-26 or SP01-15 (Lee and Pero, J. Mol. Biol. 152:247–265, 1981; hereby incorporated by reference), can be added in place of the bio promoter/operator region between the XhoI and XbaI sites. After being integrated and amplified in the B. subtilis chromosome, this results in a vector capable of directing expression of the entire biotin operon from a constitutive promoter. This in turn leads to substantially improved biotin production.

TABLE 6

PCR generated fragments for 5' bio cassette construction

| PCR Fragment | Upstream primer | Downstream primer | bp* | Functional Elements |
| --- | --- | --- | --- | --- |
| B | Leader1 | ANEB1224 | 733 | RBS, start codon, 5' bioW |
| C | ORF4.1 | BIOL3 | 140 | Upstream homology, terminator |
| D | BIOL4 | BIOL5 | 95 | Promoter, operator, leader |
| E | ORF4.1 | BIOL5 | 235 | Upstream homology, terminator promoter, operator, leader |

*fragment size in bp after digestion with restriction endonucleases.

VIICi

Construction of a 5' Cassette With the SP01-26 Promoter

A 5' cassette with the SP01-26 promoter reading into the biotin operon was constructed by replacing the XhoI to XbaI fragment from the engineered "wild-type" promoter with a PCR fragment containing the SP01-26 promoter. The PCR fragment containing the SP01-26 promoter was generated from pNH201, a pUC8 subclone of the cloned SP01-26 promoter (Lee, G., Talkington, C. and Pero, J. (1980) Mol. Gen. Genet. 180:57–65.). The primers used (XHO26A and XBA26B, Table 6A) introduced an XhoI site at the upstream side of the promoter and an XbaI site at the downstream side of the promoter. THe XhoI-XbaI digested PCR fragment was ligated with XhoI-XbaI digested pBIO144, and the ligated DNA was transformed into E. coli YMC9. Plasmid minipreps from Specr transformants were screened for acquisition of an EcoRV site that is located within the SP01-26 promoter region. Plasmids showing the expected EcoRV site were then screened by PCR, using primers XHO26A and BIOW1, to confirm the juxtaposition of the SP01-26 promoter and 5'bioW fragments. Two plasmids with the correct structure, pBIO158 and pBIO159, each had the expected sequence.

VIICii

Construction of a 5' Cassette With the SP01-15 Promoter.

A DNA fragment containing the SP01-15 promoter (Lee et al., supra) with appropriate ends for cloning in pBIO144 was also generated by PCR. The primers (XHO15B and XBA15C, Table 6A) were selected to generate a fragment which flanked the SP01-15 promoter with XhoI (upstream) and XbaI (downstream) sites. There is also a potential stem-loop structure near the beginning of the transcript from SP01-15. The downstream primer was also designed to extend the potential stem-loop at the new 5' end of the bio mRNA to include the expected +1 base of the transcript initiating by the SP01-15 promoter. The XhoI to XbaI fragment containing SP01-15 was ligated into XhoI-XbaI digested pBIO144. This ligated DNA was transformed into E. coli to make pBIO168 and pBIO169. pBIO168 and pBIO169 are identical isolates that contain a 5' bio cassette with the SP01-15 promoter.

TABLE 6A

PCR primers

| Name | DNA Sequence of Primer |
| --- | --- |
| XHO26A | 5'GGCCCTCGAG GCCTACCTAG CTTCCAAGAA3' |
| XBA26B | 5'GGCCTCTAGA GCGTCCTGCT GTTGTTAAGA3' |
| BIOW1 | 5'GCCAATCCAT TCTGGAGA3' |
| XHO15B | 5'GGCCCTCGAG GCTATTGACG ACAGCTATGG TT3' |
| XBA15C | 5'GGCCTCTAGA ACAGGCGGGG TTGCCCCCGC CTGTAATTAA ATTATTACAC A3' |

VIICiii

Construction and Integration of Full Length Engineered "Wild-type" Bio Operons

Full length engineered biotin operons were constructed by introducing SalI to BamHI fragments from various engineered 5' bio cassettes, described above, between the SalI and BamHI sites of pBIO151 and pBIO152, which contain the 3' end of the bio operon and a selectable cat gene (Example VIII (b)(iii), above). Appropriate transformants were selected by complementation of the E. coli strain RY607 (Δbio) to Bio+. For example, introduction of the SalI to BamHI fragment from the "wild-type" engineered 5' biotin operon of pBIO144 into pBIO151 resulted in pBIO155 containing the full length wild-type bio operon with the 3' flanking region, and a cat gene oriented in the same direction as the biotin operon. Ligation of the same 5' fragment from pBIO144 into pBIO152 gave pBIO156 with the same features as pBIO155 but lacking the 3' flanking region downstream of the bio operon.

Plasmids pBIO155 and pBIO156 were integrated into B. subtilis with the entire plasmid or with the E. coli vector sequences deleted (Table 7). B. subtilis strains PY79, BI421 and HB3 (both birA mutants; see Example X) were transformed with plasmids pBIO155 and pBIO156 and chloramphenicol resistant colonies were selected. Amplification of the integrated plasmid was achieved by streaking the strains on plates with increasing levels of chloramphenicol (Table 7, strains BI228, 230, 235, 237, 243 and 245).

To construct strains which contained amplified copies of the wild-type biotin operon but no E. coli sequences, plasmids pBIO155 and pBIO156 were digested with NotI. The larger fragment from each digest was circularized and used to transform B. subtilis strains PY79, BI421, and HB3. The cassette was amplified by streaking on plates with increasing levels of chloramphenicol (Table 7, strains BI232, 234, 239, 241, 247, and 249).

SP01 promoter driven bio operon ligations were transformed directly into B. subtilis. Isolated NotI to BamHI fragments from 5' cassettes (5' flanking sequence, promoter region and 5' bioW) and isolated BamHI to NotI fragments from 3' cassettes (3' bioW, bioA, bioF, bioD, bioB, bioI, ORF2, terminator, 3' flanking sequence, and cat) were ligated under standard conditions and used to transform various B. subtilis strains. The 5' NotI to BanHI cassettes were from pBIO158 containing the SP01-26 promoter or pBIO168 with the SP01-15 promoter. The 3' cassettes were from either pBIO151 with the extended 3' flanking sequence or pBIO152 with the truncated 3' flanking sequence (Table 7, strains BI267, 268, 274, 276, 278, and 282).

Each of these DNA ligations was transformed into a wild-type strain PY79 and in some cases also into a biotin-deregulated strain, BI421 (birA mutant, see Example XB below). Competent cells of the strains were prepared by standard methods and transformed with the different bio-containing DNA ligation mixtures described above, selecting for Cm$^r$. Since these DNA's cannot replicate in *B. subtilis*, Cm$^r$ transformants arise by integration of the ligated DNA into the chromosome at the bio locus via recombination between homologous sequences present on the chromosome and the transforming DNA. In each experiment, 10–50 Cm$^r$ transformants were selected for characterization. Transformants were screened by PCR to confirm that the SP01 promoter was juxtaposed to bioW.

TABLE 7

First generation biotin production strains.

| Strain Sequences | Parent | Integrated DNA | Promoter | 3' Flanking |
|---|---|---|---|---|
| BI222 | PY79 | pBIO401cat$_S$ | biotin | yes |
| BI224 | BI421 | pBIO401cat$_S$ | biotin | yes |
| BI226 | HB3 | pBIO401cat$_S$ | biotin | yes |
| BI228 | PY79 | pBIO155 | biotin | yes |
| BI230 | PY79 | pBIO156 | biotin | no |
| BI232 | PY79 | NotI fragment pBIO155 | biotin | yes |
| BI234 | PY79 | NotI fragment pBIO156 | biotin | no |
| BI235 | BI421 | pBIO155 | biotin | yes |
| BI237 | BI421 | pBIO156 | biotin | no |
| BI239 | BI421 | NotI fragment pBIO155 | biotin | yes |
| BI241 | BI421 | NotI fragment pBIO156 | biotin | no |
| BI243 | HB3 | pBIO155 | biotin | yes |
| BI245 | HB3 | pBIO156 | biotin | no |
| BI247 | HB3 | NotI fragment pBIO155 | biotin | yes |
| BI249 | HB3 | NotI fragment pBIO156 | biotin | no |
| BI267 | PY79 | 5' pBIO158, 3' pBIO151 | SP01-26 | yes |
| BI268 | BI421 | 5' pBIO158, 3' pBIO151 | SP01-26 | yes |
| BI274 | PY79 | 5' pBIO158, 3' pBIO152 | SP01-26 | no |
| BI276 | BI421 | 5' pBIO158, 3' pBIO152 | SP01-26 | no |
| BI278 | PY79 | 5' pBIO168, 3' pBIO151 | SP01-15 | yes |
| BI282 | PY79 | 5' pBIO168, 3' pBIO152 | SP01-15 | no |

EXAMPLE VIII

Characterization of First Generation *B. subtilis* Biotin Production Strains

Southern blot experiments were used to confirm the structure of the integrated cassettes and to assess the degree of amplification of a representative subset of the engineered strains. From these experiments, it was clear that the presence of the SP01 promoters had a significant effect on the degree of amplification. Engineered, full-length bio operons containing a wild-type bio promoter were amplified in strains grown on 60 µg/ml chloramphenicol to levels similar to those seen for other operons under similar conditions (estimated 15 copies/cell). However, bio operons driven from an SP01-15 promoter showed 2-fold less amplification and bio operons driven from the SP01-26 promoter were about four-fold less amplified. Thus, *B. subtilis* cells have a limited tolerance for at least one of the products encoded by the bio operon.

IIA

Assay for Production of Biotin and Biotin Precursors in Test Tube Cultures

To determine the effect of mutiple copies of the wild-type bio operon or SP01-modified bio operons on biotin production, the wild-type and biotin-deregulated *B. subtilis* strains containing these engineered bio operons, integrated and amplified in their chromosomes, were tested for biotin production. The results are shown in Table 8.

All of the strains were grown overnight in 5 ml of VY medium at 37° C., centrifuged, and the supernatant solutions autoclaved for 5 minutes to kill any remaining cells. (Biotin and desthiobiotin are stable to autoclaving.) The supernatant solutions were diluted in biotin-free medium and inoculated with *E.coli* strains RY604 (ΔbioH) and RY607 (ΔbioABFCD). RY604 and RY607 were constructed by transducing the relevant regions from BM7086 and a Δ(gal-uvrB219 strain, respectively, (Cleary and Campbell, supra; Hatfield et al., supra) into MM294. The former grows on both biotin and biotin vitamers, while the latter grows on biotin only. The biotin and biotin vitamers produced by different *B. subtilis* mutant strains were calculated from a standard curve at OD$_{600}$.

The wild-type strain of *B. subtilis*, PY79, typically yielded about 6–10 µg/l of biotin in this assay (Table 8). The VY medium used for these experiments had 20–45 µg/l biotin before cell growth. Thus, most of the biotin contributed by the medium was consumed during growth by wild-type bacteria.

Several biotin analog-resistant mutants produced 50–100 µg/l biotin, 5–10 fold more biotin than found with the wild-type strain. Two biotin analog-resistant strains with birA-like mutations were used. One mutant strain, HB3, contains a spontaneous homobiotin-resistant mutation. The other strain, BI421, contains an ethylmethylsulfate-generated α-dehydrobiotin-resistant mutation which had been crossed into an unmutagenized background (see Example X). Both strains yielded 50–100 µg/l of biotin in these experiments (Tables 8 and 9).

Integration and amplification of a "wild-type" copy of the bio operon in the wild-type strain PY79 generally improved biotin production 10–50 fold over that seen with PY79 alone (Table 8). Such strains (BI230 and BI234) produced 150–600 µg/l compared to the 6–10 µg/l produced by PY79 alone. However, more dramatic results were seen from the assays of the birA mutant strains with integrated and amplified copies of the wild-type bio operon. An additional 5–10 fold improvement in biotin production was observed with yields up to 2,000 µg/l biotin, with this assay (see BI241, BI237, BI249; Table 8).

Analysis of wild-type *B. subtilis* strains containing the engineered bio operons with an SP01 promoter resulted in an improvement in biotin production, with biotin titers generally 1000–2000 µg/l (see BI267 and BI274; Table 9) versus 150–600 µg/l with the wild-type bio promoter. No dramatic difference was seen in biotin production between wild-type and birA mutant strains containing constitutive promoters (Table 9).

A second type of assay employs Lactobacillus plantarum as a biotin indicator (Wright et al., *Proc. Soc. Exp. Biol. Med.* 56:95–98, 1944) and *Saccharomyces cerevisiae* as an indicator of biotin vitamers (Baldet et al., *Eur. J. Biochem.* 217:479–485, 1993). Assays were performed as described except that an antibiotic was added to the assay cultures to reduce interference by contamination. Since *L. plantarum* is sensitive to most antibiotics, a spontaneous streptomycin resistant mutant, *L. plantarum* str3, was selected and used for biotin assays in the presence of 50 µg/ml streptomycin sulfate. *S. cerevisiae* is naturally resistant to most antibacterial compounds and was also used in the presence of 50 µg/ml streptomycin sulfate. The *L. plantarum* growth response to biotin decreases more gradually (over a dilution range of about 50-fold) than the *E. coli* growth response. *S. cerevisiae* is more responsive to DAPA and KAPA than *E. coli*.

When cultures were assayed for biotin production with Lactobacillus as an indicator, more precise levels could be determined. Using these conditions, *B. subtilis* strains with the engineered SP01-bio operons yielded almost twice as much biotin as deregulated *B. subtilis* strains with amplified copies of the wild-type bio operon (Table 10).

TABLE 8

Biotin production by various *B. subtilis* strains containing integrated and amplified wild-type bio operons in test tube cultures.

| Strain name | Relevant features | Biotin (μg/l)* | Biotin & Biotin Vitamers (μg/l)** |
|---|---|---|---|
| PY79A | prototroph | 10 | 10 |
| PY79B | prototroph | 6 | 6 |
| HB3 | birA | 100 | 100 |
| BI230 | PY79::[pBIO156]$_{60}$ | 150 | 250 |
| BI234 | PY79::[Not/156]$_{60}$ | 600 | 1,200 |
| BI245 | HB3::[pBIO156]$_{60}$ | 500 | 2,000 |
| BI249 | HB3::[Not/156]$_{60}$ | 1,500 | 1,500 |
| BI237 | BI421::[pBIO156]$_{60}$ | 1,000 | 3,000 |
| BI241 | BI421::[Not/156]$_{60}$ | 2,000 | 3,000 |

*Assayed using *E. coli* RY607 (ΔbioABCDF)
**Assayed using *E. coli* RY604 (ΔbioH)

TABLE 9

Biotin production by various *B. subtilis* strains containing integrated and amplified SP01-engineered bio operons.

| Strain Name | Relevant Features | Biotin (μg/l)* | Biotin & Vitamers (μg/l)** |
|---|---|---|---|
| PY79A | prototroph | 10 | 10 |
| BI421 | birA | 50 | 120 |
| BI421 | birA | 80 | 150 |
| BI267 | PY79::[Not/158, 151]$_{60}$ | 1,000 | 2,000 |
| BI268 | BI421::[Not/158, 151]$_{60}$ | 1,300 | 5,000 |
| BI274 | PY79::[Not/158, 152]$_{60}$ | 1,500 | 2,500 |
| BI276 | BI421::[Not/158, 152]$_{60}$ | 1,500 | 3,500 |

*Assayed using *E. coli* RY607 (ΔbioABCDF)
**Assayed using *E. coli* RY604 (ΔbioH)

TABLE 10

Biotin production by various *B. subtilis* strains.

| Strain name | Relevant features | Biotin (μg/l)* | Biotin & Vitamers (μg/l)** |
|---|---|---|---|
| PY79 | prototroph | 6 | 10 |
| BI421 | birA | 45 | 200 |
| BI239 | amplified wild-type bio operon/birA | 580 | 2700 |
| BI282 | amplified SP01-15-bio operon/PY79 | 1100 | 3600 |

*Assayed with *L. plantarum* str3
**Assayed with *S. cerevisiae*

VIIIB
Strain Evaluation for Large-scale Biotin and Biotin Precursor Production

Engineered biotin-producing strains can be evaluated for large-scale biotin and biotin precursor production using fermentation technology. A range of fermenters and media conditions can be applied. As an example, all of the following fermentations were performed in computer controlled 14-liter Chemap fermenters utilizing a DO (dissolved oxygen) control, glucose-limited, fed batch fermentation strategy. The amount of biotin or biotin precursor produced was determined by inoculating serial dilutions of autoclaved cell-free broth with the appropriate strains of *Lactobacillus plantarum* or *Saccharomyces cerevisiae* as described above. The medium composition and other fermentation conditions are described in Table 11.

Biotin and biotin precursors produced by various strains are listed in Table 12. In all fermentations, 1 g/l pimelic acid was added to both the initial batch and feed solutions. BI282, BI278 and BI276 were the most optimized for biotin and biotin vitamer production.

TABLE 11

Biotin fermentation conditions and medium (VY) composition.

| | Grams | Volume | Time of Addition |
|---|---|---|---|
| Initial Batch | | | |
| A. Veal Infusion Broth | 150.00 | 4.5 liters | Sterilized for |
| Yeast Extract | 30.00 | | 60 mins. in |
| Sodium Glutamate | 30.00 | | fermenter 12.5 |
| $KH_2PO_4$ | 45.00 | | ml 50% NaOH |
| $MgCl_2.6H_2O$ | 9.00 | | pH 6.8 prior to |
| $MnSO_4.H_2O$ | 0.30 | | sterilization, |
| $FeCl_3.6H_2O2$ | 0.15 | | pH 6.6 post |
| $(NH_4)_2SO_4$ | 12.00 | | sterilization |
| MAZU DF37C | 15.00 | | Approximately 800 ml volume gain |
| B. Glucose | 150.00 | 0.3 liters | Added to |
| $CaCl_2.2H_2O$ | 6.00 | | fermenter immediately prior to inoculation |
| Feed Solution | | | |
| C. $KH_2PO_4$ | 54.70 | 0.2 liters | Added to D |
| $MgSO_4.4H_2O$ | 6.00 | | |
| D. Glucose | 3,000 | 3.3 liters | Combined with C and fed to fermenter |
| Inoculum Medium | | | |
| E. Inoculum Medium Composition = "A" + 0.35 gm $CaCl_2.2H_2O$ | | 300 ml | Autoclaved separately Presterilization pH adjusted to pH 6.8 |
| F. 20% Maltose | | 50 ml | Added to E after cooling |
| G. 20% Glucose | | 25 ml | Added to E after cooling |
| Acid | | | |
| H. 3.5% $H_2SO_4$ | | 200 ml | Usual requirement for pH control |
| Base | | | |
| I. Anhydrous $NH_3$ | | | pH control |

All solutions (A-14 G) sterilized separately and combined when cool.
Conditions Air: 1.5–2.0 vvm; RPM: 1000; pH 6.8; Temp. 37.8° C.; Pressure 0.6 bar.

TABLE 12

Biotin and vitamer production by first generation *B. subtilis* strains in bench scale fermenters.

| Fermentation Run[a] | Strain | Promoter/strain background | Biotin (mg/liter)[b] | Vitamers (mg/liter)[c] |
|---|---|---|---|---|
| B22[d] | BI239 | $P_{bio}$/BI421 (birA) | 1 | 30 |
| B19 | BI268 | SP01-26/BI421 (birA) | 5 | 40 |
| B23 | BI276 | SP01-26/BI421 (birA) | 8 | 120 |

TABLE 12-continued

Biotin and vitamer production by first generatian B. subtilis strains in bench scale fermenters.

| Fermentation Run[a] | Strain | Promoter/strain background | Biotin (mg/liter)[b] | Vitamers (mg/liter)[c] |
|---|---|---|---|---|
| B20 | BI278 | SP01-15/PY79 | 10 | 60 |
| B24 | BI282 | SP01-15/PY79 | 8 | 100 |

[a]All fermentations used VY salts medium (described in Table 11) with 1 g/liter pimelic acid in both batch and feed.
[b]Assayed at 34 hours with L. plantarum str3.
[c]Assayed at 34 hours with S. cerevisiae.
[d]The $OD_{600}$ of the culture was decreasing after 24 hours.

TABLE 13

Effect of complex nitrogen/nutrient source concentration on biotin and vitamer production by strain BI282 in bench scale fermenters.

| Fermentation Run | Medium[a] | Biotin (mg/liter)[b] | Vitamers (mg/liter)[c] |
|---|---|---|---|
| B30 | 1 × BY | 10 | 150 |
| B29 | 2 × BY | 16 | 200 |
| B31 | 3 × BY | 8 | 130 |

[a]Fermentation conditions as deacribed in Table 5, except with 1 g/liter pimelic acid in batch and feed, and with beef extract and proteose peptone substituted for veal infusion broth.
[b]Assayed at 30 hours with l. plantarum str3.
[c]Assayed at 30 hours with S. cerevisiae.

VIIIC
Analysis of Fermentation Broths by Bioautography

The spectrum of vitamers secreted by biotin-producing strains can be assayed by bioautography techniques. In the present case, fermentation broths were clarified by centrifugation and sterilized by autoclaving. One microliter aliquots of supernatant culture fluids were spotted on Baker-flex microcrystalline cellulose thin-layer chromatography (TLC) plates and the compounds were separated with a solvent of n-butanol and 1N HCl (6:1 v/v). After drying, the chromatograph was incubated for 1 hour, face down, on a biotin-free agar plate containing 2,3,5-triphenyltetrazolium chloride and kanamycin, and impregnated with E. coli strain RY604 (ΔbioH)/pOK12 (Kan[R]). The KanR plasmid pOK12 (Viera and Messing (1991) Gene 100:189–194) was added to RY604 merely to provide antibiotic resistance so that contamination could be reduced in the assay. The TLC plate was then removed and the agar plate incubated at 37° C. After 20 hours, spots of growth corresponding to the location of biotin and vitamers on the TLC plates appeared. FIG. 15 shows biotin and vitamer standards with representative fermentation samples. The $R_f$ values observed with this chromatography system are indicated in Table 14. The technique can also be employed using paper chromatography instead of cellulose TLC (Table 14). Comparison to bioautography utilizing RY634 (ΔbioA-D::Kan[R], Bis[+]), which detects only biotin and biotin sulfoxide, indicated that substantial quantities of both desthiobiotin and biotin were present in the fermentation broth.

Addition of pimelate to the fermentation medium results in an increased level of a biotin vitamer which is probably KAPA (FIG. 15, lane D). This was shown by an increase in the KAPA/BSO spot compared to similar fermentations without pimelate (FIG. 15, lane B). Part of this material was demonstrated to be biotin sulfoxide, since it was also detected on bioautography utilizing RY634 (ΔbioA-D::Kan[R], Bis[+]) which detects only biotin and biotin sulfoxide. However, the intensity of the spot generated with RY634 at the KAPA/BSO location was significantly less than that detected with RY604/pOK12.

The accumulation of desthiobiotin and KAPA indicate limitations at the biosynthetic steps encoded by bioB and bioA. Such limitations may be overcome by elevated expression of these individual genes or by increases in the pools of substrates, cofactors or cooperating proteins for these steps. The expression of bioB or bioA can be separately elevated by either inserting subclones of the individual genes or PCR copies of the genes in an expression vector with a strong promoter (SP01, veg, etc.) and introducing the DNA into the cell on a plasmid such as pUB110, in a phage such as SPβ, or integrated directly into a nonessential gene in the chromosome such as bpr.

TABLE 14

Observed and reported $R_f$ values for biotin vitamers on cellulose chromatography.

| | Rf | |
|---|---|---|
| Biotin vitamer | Observed, TLC | Literature[a], Paper |
| DAPA | 0.09 | 0.09 |
| KAPA | | 0.35 |
| Biotin sulfoxide | 0.52 | |
| Biotin | 0.86 | 0.70 |
| Dethiobiotin | 0.94 | 0.82 |

[a]Agric. Biol. Chem. 39:779–784 (1975)

VIIID
Analysis of Bio-specific mRNA Synthesis in the Engineered Strains

Northern blot experiments were performed on selected strains to examine the transcription pattern of the bio operon and the amount of bio-specific mRNA present in the various engineered strains. As expected a 7 kb RNA transcript covering the entire bio operon could be seen in all engineered strains. Lesser amounts of this transcript were also present in wild-type and birA mutant B. subtilis strains. In addition, all strains contained larger amounts (~8-fold) of a 5 kb transcript covering the first five genes in the bio operon, suggesting that a significant amount of transcript ended at a potential termination site after bioB (FIG. 5A). Significant amounts of a small transcript of 0.8 kb that covered most of the bioW gene were also seen. This transcript ended near a sequence with similarity to the consensus sequence of a site implicated in catabolite repression (Chambliss, G. H., "Bacillus subtilis and Other Gram-Positive Bacteria" ed. Sonenshein et al., Am. Soc. Microbiology, pp.213–219, 1993, hereby incorporated by reference). The relative ratio of the three transcripts to each other was the same in wild-type strains grown in the absence of biotin, birA mutant strains, or engineered strains driven by either the wild-type bio promoter or an SP01 promoter. Only the absolute amount of total bio-specific RNA varied dramatically in these strains. The engineered first generation production strains with a wild-type or an SP01-15 promoter produced about 30-fold or 60-fold, respectively, more bio-specific RNA than a derepressed wild-type cell. The bio-specific RNA levels in the birA mutant were only slightly (2–3 fold) higher than RNA levels in the derepressed wild-type cell, and were not affected by growth on biotin.

It appeared from these experiments that the SP01-promoters were directing the synthesis of at least 4-fold more RNA per operon than the wild-type bio promoter.

However, with the reduced copy number of the SP01-bio operons, the total amount of bio specific RNA was at most only two-fold more than seen with a fully amplified, wild-type operon. The RNA levels correlated with biotin production levels, strains with the engineered, amplified SP01-bio operons produced about two-fold more biotin than birA mutant strains with the amplified wild-type operons, thus confirming that increasing the expression of one or more of the bio genes would lead to increases in biotin titer.

EXAMPLE IX
Genetic Mapping of a BirA-like Gene of B. subtilis

In addition to cloned DNA that contains the B. subtilis bio operon, two recombinant plasmids, pBIO113 and pBIO114, were recovered which contained B. subtilis chromosomal DNA that complemented a temperature-sensitive mutation in the birA regulatory gene of E. coli. The birA gene product functions in E. coli both as an enzyme that catalyzes the addition of biotin to apoenzymes and as a repressor protein that negatively regulates expression of the bio biosynthetic genes.

The location of the birA-complementing gene on the B. subtilis chromosome was mapped by PBS1 generalized transduction. To do this, a B. subtilis bacterial strain was generated that contained a selectable antibiotic-resistance marker, cat, near the birA locus. Then, by determining the position of cat in the chromosome, the birA-complementing DNA was mapped. A derivative of pBIO113 was constructed that contained a cat cassette (obtained from pMI1101 (Youngman et al. *Plasmid* 12:1–9, 1984), and this integration vector was introduced into the B. subtilis chromosome. Since the 7.0 kb cloned insert of pBIO113 is homologous to its corresponding segment in the B. subtilis chromosome, integration of the cat-containing pBIO113 into the chromosome by Campbell recombination (Campbell, *Adv. Genet.* 11:101–145, 1962) introduced the cat gene near birA. Using standard PBS1-transduction mapping, the birA-complementing DNA was mapped to the 202° region of the chromosome, very near the trp locus (>90% linkage).

EXAMPLE X
Construction of a B. subtilis Host Strain Deregulated for Biotin Production XA
Construction of Biotin Analog-resistant Strains Biotin analogs were used to select for strains that were deregulated for biotin production. Among the mutations sought were those in a potential homolog of the E. coli birA gene. However, it is expected that selection for resistance to biotin analogs can also yield strains with mutations in the operator site(s) of birA, or in genes encoding functions responsible for the transport of the analogs into the cell. Analog-resistant mutants can also contain a gene or genes that encode enzymes resistant to inhibitors including, but not limited to, feedback inhibitors. Several biotin analogs (homobiotin, α-dehydrobiotin, and 5(2-thienyl)pentanoic acid) were obtained from Nippon Roche KK (Kanagsua, Japan). Mutagenized cells of B. subtilis were plated on TBAB (Difco Tryptose Blood Agar Base, cat. no. 0232-01-9) plates containing a crystal of each biotin analog.

B. subtilis PY79 (an SPβ-cured prototroph derived from S. A. Zahler strain CU1769 (metB5,glnAr100; Youngman et al. 1984 supra) was mutagenized with ethyl methane sulfonate (EMS) to give 90% killing. Surviving cells were grown overnight and 0.1 ml of culture was plated on TBAB plates. A crystal of two of the biotin analogs was placed on the plate and incubated overnight at 37° C. The α-dehydrobiotin and 5(2-thienyl)pentanoic acid crystals inhibited the growth of B. subtilis and gave zones of clearing around the crystals. Within the clear zones individual colonies appeared, providing likely candidates for biotin-analog resistant strains.

Several colonies were picked from the zones of clearing around the analogs α-dehydrobiotin and 5(2-thienyl) pentanoic acid) and named DB-1 to DB-4 inclusive if selected from an α-dehydrobiotin zone, and TP-1 to TP-3 inclusive if selected from a 5(2-thienyl) pentanoic acid zone. The isolated colonies were streaked onto minimal-casamino acid plates with various amounts of each analog. All of these strains grew better (i.e., produced a larger colony) than wild-type cells on their respective analogs.

An additional 27 mutants were selected subsequently in similar plate screenings for their resistance to the analogs homobiotin (HB) and α-dehydrobiotin (α-DB). For this latter selection, B. subtilis PY79 cultures were subjected to mutagenesis with EMS in two independent experiments. The first mutagenesis, EMS1, resulted in 96% killing whereas the second, EMS2, resulted in 82% killing of the bacteria. Overnight cultures of PY79, EMS1, and EMS2 grown in rich medium were plated on TBAB (rich), BIOS (biotin free) or MIN (glucose-minimal) plates and a crystal of homobiotin or α-dehydrobiotin was placed on each of the plates. After 24 h, zones of killing were observed with a few resistant colonies growing within these zones. Individual colonies were picked from homobiotin plates or α-dehydrobiotin plates and restreaked on BIOS plates containing α-dehydrobiotin or homobiotin.

Potential repressor or operator deficient mutants were screened for their ability to secrete a measurable level of biotin. Each mutant strain was assayed for biotin and biotin vitamer production. Each strain was grown in VY medium (5 ml; 20 g/l Difco veal infusion broth and 5 g/l Difco yeast extract) for 18–24 hours at 37° C., and the supernatant was sterile-filtered. The filtered supernatants were then serially diluted in a biotin-free medium, and the serial dilutions were inoculated with E. coli strains RY604 (ΔbioH) and RY607 (ΔbioABFCD); the former grows on both biotin and biotin vitamers while the latter grows on biotin only. The biotin and biotin vitamers produced by different B. subtilis mutant strains were calculated from standard curves generated with biotin and desthiobiotin. Six mutants from the collection produced about 100 µg/L of secreted biotin: homobiotin resistant mutants HB3, HB9, and HB15; and α-dehydrobiotin resistant mutants α-DB9, α-DB16, α-DB17. Other mutants produced either no biotin or 10 µg/L. Other mutants selected by the above method can be expected to provide 75 µg/L, 150 µg/L, or even 200 µg/L, 250 µg/L, or 300 µg/L.

XB
Mapping Biotin Analog Resistance Mutations

Example IX described mapping of the B. subtilis birA gene to a position just downstream of trpC2. The six biotin-secreting, analog-resistant mutants were examined for linkage to trpC2 by phage transduction to determine if they are located in a birA-like repressor. Each candidate was crossed with B. subtilis 168 (trpC2), and Trp$^+$ transductants were patched to minimal plates with or without homobiotin. Results indicated that five of the six analog resistant mutations (HB3, HB9, HB15, α-DB16, and α-DB17) are closely linked to the birA locus (90%–95% co-transduction of Trp$^+$ and analog-resistance). BI421 is a homobiotin resistant (HB$^r$) Trp$^+$ transductant of strain 168 containing the birA mutation of α-DB16.

The sixth analog resistant mutation, that contained in αDB9, was not linked to trpC, and therefore is not a single mutation at birA. By transducing from α-DB9 into a bioW::cat7 strain in a similar tranduction mapping experiment (see FIG. 9), the mutation in α-DB9 was shown to be unlinked to the biotin operon. Therefore the mutant phenotype of α-DB9 is either due to a mutation at a third locus distinct from birA and from bioWAFDBI, or it is due to mutations at more than one locus, all of which are required to express the analog-resistant phenotype. The α-DB9 mutation can affect a biotin permease, a biotin export pump, or an enzyme related to biotin biosynthesis. Analog-resistant mutations that are at different loci (such as those of HB3 and α-DB9) can be combined in a single strain by standard strain construction techniques to give a strain with even greater capacity for biotin secretion. These analog-resistant mutants, or other mutants isolated and screened by the above procedures, may be used as host strains for biotin overproduction.

Two additional biotin analog-resistant mutations carried by α-DB12, isolated for resistance to dehydrobiotin as described above, and HB43, a spontaneous homobiotin-resistant mutant of PY79 (pBIO397cat), were also mapped to the birA locus.

XC
DNA Sequence of B. subtilis BirA Mutants

Mutations resulting in amino acid changes can be found in the birA genes of homobiotin resistant strains such as HB3 and α-dehydrobiotin resistant strains such as α-DB16. To find such mutations, the DNA sequence of a wild-type B. subtilis birA gene can be compared with the DNA sequence of B. subtilis birA genes containing biotin analog-resistant mutations. The wild-type B. subtilis birA gene sequence can be obtained by sequencing the cloned birA+ gene on pBIO113 or pBIO114. The mutant birA gene sequences can most easily be obtained from PCR copies of the gene. Several independent PCRs can be performed using genomic DNA from each birA mutant as template, and a pair of primers known to flank the birA coding region. DNA fragments can then be isolated from each independent PCR and cloned in E. coli pUC21 (Viera and Messing (1991) Gene 100:189–194). Isolates from each of two independent PCRs can be sequenced on both strands using a series of internal primers. Any artifactual mutations introduced by PCR should appear in only one of the two independent PCR clones, while the "true" mutation should appear in both independent isolates.

By comparison to the E. coli birA protein, for which the three dimensional structure is known (Wilson et al. (1992) Proc. Nat'l. Acad. Sci. USA 89:9257–9261), the mutations can be characterized. For example, the mutation may be located in one of the DNA-contacting helices. This information can be used to construct improved birA mutant strains of B. subtilis with reduced capacity to regulate expression of the bio operon. For example, two of the sequenced mutations could be combined in one gene using well known methods of site directed mutagenesis. Alternatively, small deletions that remove the DNA binding portion of birA, but not the biotin ligase activity can be constructed.

EXAMPLE XI
Second Generation of Engineered B. subtilis Biotin Production Strains While constructing and characterizing the first generation of engineered B. subtilis biotin production strains, applicants observed several limiting steps in the biotin regulatory system, modification of which can increase biotin production. For example, SP01 promoter-driven biotin operons were not amplified to as high a copy number as wild-type biotin operons, as shown by Southern blot data. First, identification of the gene product that is deleterious to the cell when overproduced, and deletion of this gene from the amplified cassette, can circumvent this problem. Second, there are two points of partial pre-mature termination of mRNA synthesis in the biotin operon. The following Examples illustrate how this understanding of the biotin wild-type regulatory scheme can be used to optimize biotin production.

XIA
Constructions to Improve the Copy Number of SP01 Promoter-driven Bio Cassettes As shown above, biotin operons driven by SP01 promoters are less amplified than a biotin operon controlled by the wild-type operon. Applicants reasoned that the product of one or more of the bio genes is not tolerated at high levels. High level amplification can be achieved with a biotin operon lacking that specific bio gene. To determine which of these genes was not tolerated at high levels, Applicants designed the following experiment.

First, to assure some constitutive level of expression of all the bio genes, the biotin promoter was replaced in the chromosome with an SP01-15 promoter. To do this, an upstream homologous sequence was added to a 5' cassette containing the SP01-15 promoter (pBIO168). This construction was made by introduction of a 1.8 kb PCR fragment, generated from the sequence just upstream from the 5' biotin cassettes, into the SalI to NruI gap of pBIO168. The 1.8 kb PCR fragment was generated using primers designed to introduce a NruI site at the upstream, and a SalI site downstream, end. The resulting plasmid, pBIO180, has the SP01-15 promoter flanked by 1.8 kb of homologous sequence upstream of the bio operon and 0.7 kb downstream of the promoter. This plasmid was used to transform $\Delta$::cat$_{17}$ (see Example III), which has the promoter region of the biotin operon replaced by a cat cassette and is auxotrophic for biotin. A double recombination event allowed the replacement of the cat cassette with the SP01-15 promoter yielding the desired prototrophic strain, BI294 Cm$^s$.

A deletion in each of the bio genes can be generated by standard techniques. Below is one example of how a non-polar deletion mutation was constructed in bioW.

A deletion of bioW was generated by altering the 5' cassette pBIO168. A PCR fragment was generated which has the SP01-15 promoter and first three codons of bioW followed by a BamHI site (FIG. 14). This PCR fragment was engineered so that after replacing the XhoI to BamHI fragment of pBIO168, the resulting 5' cassette, pBIO178, forms an in-frame bioW deletion upon ligation with the 3' bio cassettes (see FIG. 14). Transformation of this ligation mixture into B. subtilis BI294 (see above) and selection of Cm$^r$ integrants (BI296) allowed amplification of the biotin operon without amplifying bioW. The chromosomal copy of bioW still transcribed from the SP01-15 promoter. A control with a complete SP01-15 driven biotin operon integrated into BI294 was also constructed and called BI295. Copy number of the operon was reduced in both cases, compared to amplified BI247 (Example VIICiii). Comparison of the amplification of these two strains suggested that bioW is not the gene whose product is deleterious when overproduced.

This procedure can be repeated with each bio gene in turn to identify the gene that is deleterious when overproduced.

Analysis of biotin production by BI296, lacking the amplified bioW gene, compared to the isogenic strains BI295, containing an amplified bioW gene, indicated that the product of bioW is not the rate-limiting enzyme for biotin biosynthesis (Table 15A). BI296 produced about 10 times more biotin than the parent strains BI294 without the amplified bio cassette. Furthermore, BI296 produced similar amounts of biotin as BI295, the isogenic control strain with the complete SP01-bio operon. Repeating such experiments with internal, nonpolar deletions in each bio gene will identify the rate-limiting gene for biotin biosynthesis in *B. subtilis*.

TABLE 15A

Biotin production by various *B. subtilis* strains.

| Strain name | Relevant features | Biotin (μg/l)* | Biotin & Vitamers (μg/l)** |
|---|---|---|---|
| PY79 | prototroph | 4 | 10 |
| PY79 | prototroph | 6 | 10 |
| DB16 | birA | 46 | 140 |
| BI294 | SP01-bio/PY79 | 165 | 360 |
| BI294 | SP01-bio/PY79 | 125 | 450 |
| BI295A | amplified SP01-bio operon/BI294 | 1116 | 3150 |
| BI295B | amplified SP01-bio operon/BI294 | 1405 | 5000 |
| BI296A | ΔbioW amplified SP01-bio operon/BI294 | 1402 | 4000 |
| BI296B | ΔbIoW amplified SP01-bio operon/BI294 | 1574 | 3950 |

*Assayed with *L. plantarum* str3.
**Assayed with *S. cerevisiae*.

XIB
Removal of Possible Transcription Termination Sites

There are two internal sites of termination within the biotin operon. An MRNA fragment of about 0.8 kb is observed which corresponds to the distance from the promoter to a region in bioW which shares homology with the consensus sequence for a *B. subtilis* catabolite repression sequence (CRS). The major biotin transcript seen in Northerns is 5.2 kb. This corresponds to the distance between the promoter and the bioB-bioI junction where a stem-loop structure is followed by a string of T residues. Constructions were made to eliminate the CRS and to increase the level of transcription past the bioB-bioI junction to the end of the operon.

XIBi
Removal of the Catabolite Repression Sequence

In *B. subtilis*, sporulation and the synthesis of certain enzymes are subjected to catabolite repression. (Chambliss, G. H., in "*Bacillus subtilis* and Other Gram-Positive Bacteria" Sonenshein et al., eds. Amer. Soc. Microciology, Washington, D.C. pp. 213–219, 1993; hereby incorporated by reference).

Two potential catabolite repression sites (CRS) are located in or around the bio operon. One is located within the putative 5' leader region of ORF3. The second catabolite repression-like sequence was located within the 3' end of bioW. The location of this sequence coincides with the 3' end of a 0.8 kb -specific transcript detected in Northern blots, suggesting that catabolite repression might control, in part, expression of the bio operon. There is also a short AbrB regulatory sequence within this catabolite repression-like sequence (Stauch, M. A., in "*Bacillus subtilis* and Other Gram-Positive Bacteria", Sonenshein et al. eds. Amer. Soc. Microbiology, Washington, D.C. pp. 757–764, 1993).

The portion of bioW encoding the BamHI site and the CRS is illustrated in FIG. 17A. The CRS starts 11 bp downstream from the BamHI site. Four codons in the sequence comprising the CRS can be converted to alternative codons by changes in the third position without altering the amino acid sequence. The third position changes alter three of the four most highly conserved residues (underlined) of the CRS (FIG. 17A).

As shown in FIG. 17A, the CRS site in bioW also has significant homology to an AbrB consensus binding site. A concern when altering the sequence of a CRS is that the binding site for AbrB is similar in sequence and care must be taken not to generate a strong AbrB binding site when destroying the CRS. However, the alterations introduced to destroy the CRS also reduce homology to the AbrB site. To introduce the changes indicated in FIG. 17A, a PCR primer was designed to include the BamHI site, the CRS region with the desired mutations, and twenty residues for priming. An appropriate downstream primer allowed generation of a 660 bp fragment which could be digested with BamHI and Bst1107I. Both BamHI and Bst1107I restriction enzymes have unique sites in the plasmid pBIO289. The BamHI and Bst1107I cut PCR product was cloned into BamHI and Bst1107I cut pBIO289 to yield plasmid pBIO179. The BamHI to EcoRI fragment from pBIO179 was then cloned into pBIO146A to generate a new 3' cassette plasmid, pBIO183. To change the sequence of the chromosomal copy of bioW, a two step protocol was utilized. First a cat gene was introduced at the BamHI site in bioW (see Example III) of BI294 (Example XIA). This generated an auxotroph BI294::cat7. Transformation of the auxotroph with linearized pBIO179 and selection for Bio$^+$ yielded strain BI297 which has a single chromosomal copy of the biotin operon driven by the SP01-15 promoter with the sequence of bioW altered to destroy the catabolite repression sequence. The use of the new 3' cassette, pBIO183 with a 5' cassette i.e., pBIO168 to integrate and amplify in BI297 will assure amplification of a modified bioW and may relieve premature termination due to catabolite repression. This strain is BI306. With this procedure, second generation production strains are generated which might be less sensitive to catabolite repression.

XIBii
Removal or Bypass of the Termination Site After BioB

Two strategies were adopted to increase expression of biotin genes that lie downstream from internal sites of transcript termination. The first strategy involves deletion of the terminator. The second strategy is to insert an SP01-15 promoter in front of bioI, in order to provide strong transcription of bioI and ORF2.

To delete the terminator (FIG. 17B), which is in an intercistronic region, appropriate PCR primers were designed. One primer hybridized to bioB, upstream from a unique BspEI site. The second primer complemented the PmlI site, the ribosome binding site of bioI, skipped 51 bp and then complemented the stop codon and 23 bp at the 3' end of bioB (FIG. 17B). Digestion with BspEI and PmlI generated a 209 bp fragment which was used to replace the BspEI to PmlI fragment of pBIO289 to give pBIO181. This plasmid was used to generate a new 3' cassette by cloning the BamHI to EcoRI fragment into pBIO146A to yield pBIO185. Alteration of the chromosomal biotin operon in BI294 to delete the terminator between bioB and bioI was accomplished in two steps. First, using a strategy similar to those described in Example III, a cat gene was introduced into the end of bioB. This yielded the Bio$^-$, Cm$^r$ strain BI300. When BI300 was transformed by linearized plasmid pBIO181, Bio$^+$ isolates contained the desired terminator deletion and are represented by BI303. Integrated and amplified biotin operons containing the terminator deletion were constructed by transforming BI303 with ligated BamHI to NotI fragments from pBIO168 and pBIO185 and are represented by BI307.

To assure maximum expression of bioI and ORF2, an SP01-15 promoter was introduced in front of bioI. The SP01-15 promoter from pBIO168 was amplified by the PCR, introducing the ribosome binding site and start codon/PmlI site of bioI on the downstream side, and a StuI site on the upstream side. Primers used were: 1) 5'-GGC CAT TCT ACA CGT GAT TTT CTC CTT TCT GTC TAG AAC AGG CGG GGT TGC; and 2) 5'-GGC CAG GCC TGG CTA TTG ACG ACA GCT ATG GTT. Since digestion-of DNA by StuI and PmlI creates blunt ends, digestion of pBIO289 with PmlI allowed introduction of the StuI/PmlI digested PCR fragment. In one orientation the PmlI site is regenerated at the bioI start codon and the SP01-15 promoter directs transcription of bioI and ORF2. The plasmid with this orientation was called pBIO182. A new 3' cassette (pBIO184) was constructed by cloning the BamHI to EcoRI fragment of pBIO182 into pBIO146A. This construction is expected to generate even more transcription of bioI and ORF2 than would be generated by elimination of termination between bioB and bioI.

The SP01-15 driven bioI construction was introduced into the chromosomal copy of BI294 by transduction of BI300 (see above) with linearized pBIO182 and selection for Bio$^+$ yielding BI304. Integration and amplification gave BI308.

XIBiii
Biotin Production by Single Copy Terminator Modified Strains

Biotin and vitamers were assayed from test tube cultures as described in Example VIIIA utilizing Lactobacillus and Saccaromyces. BI294 was used as a control for BI303 which deleted the terminator between bioB and bioD and for BI304 which introduced a SP01-15 promoter before bioI. As demonstrated in Table 15B, deletion of the terminator or introduction of the SP01-15 promoter before bioI have little effect on biotin titers but dramatically increase the production of biotin vitamers.

TABLE 15B

Biotin and Vitamer Assays of Terminator Modified Strains.

| Strain | biotin locus | Biotin µg/l | Vitamer µg/l |
|---|---|---|---|
| BI294C | SP01-15bio | 126 | 481 |
| BI294D | | 315 | 528 |
| BI303A | SP01-15bioΔT | 313 | 838 |
| BI303B | | 200 | 790 |
| BI304A | SP01-15bio | 182 | 2800 |
| BI304B | SP01-15bioI | 179 | 3138 |

EXAMPLE XIC
Altering Bio Gene Ribosome Binding Sites

Translation of genes in the bio operon can be improved by altering the ribosome-binding sites to conform more closely to a canonical *B. subtilis* ribosome binding site with the sequence 5'AGAAAGGAGGTGA3'. Such changes can be introduced by synthesis of a DNA primer encoding an appropriate restriction site, the modified ribosome-binding site, and sufficient downstream DNA to ensure priming of a PCR reaction. By selection of an appropriate second primer, one skilled in the art can synthesize a PCR product containing the modified ribosome-binding site. This PCR fragment containing the altered ribosome-binding site can then be introduced into an engineered bio operon by the same methodology used to introduce the modified CRS sequence described in Example XIBi.

EXAMPLE XII
Azelaic Acid-resistant (AZI$^r$) Mutants of *B. subtilis*

Azelaic acid, a straight chain $C_9$ dicarboxylic acid, is a homolog of pimelic acid and is thought to be an intermediate in the conversion of oleic acid to pimelic acid (see Ohsugi and Inoue (1981) *Agric. Biol. Chem.* 45: 2355–2356, hereby incorporated by reference). Pimelic acid at 1 g/l can stimulate biotin vitamer production in *B. subtilis* and pimelic acid at 30 mg/l can restore wild-type growth to a PY79 bioI::cat$_9$ bradytroph (see Example III). Azelaic acid at 30 mg/l does not substitute for pimelic acid in supporting growth of PY79 bioX::cat$_9$. In fact, azelaic acid at 30 mg/l severely inhibited the growth of PY79 bioI::cat$_9$. Azelaic acid at higher concentrations inhibits the growth of wild-type *B. subtilis*, this inhibition being reversed by addition of 1 µg/l biotin. From these results, Applicants reasoned that azelaic acid is a specific inhibitor of biotin biosynthesis in *B. subtilis*.

A wild-type *E. coli* strain, MM294, is relatively resistant to azelaic acid. The *E. coli* strain RY604(ΔbioH), containing pBIO403 which includes only the bioW gene from *B. subtilis*, is auxotrophic for biotin, although 30 mg/l pimelic acid can satisfy the biotin requirement. However, RY604/pBIO403 grown in the presence of excess pimelic acid (80 mg/l) is sensitive to inhibition by azelaic acid. Therefore, Applicants concluded that azelaic acid acts at the level of pimelyl CoA synthetase (bioW), either as a competitive inhibitor of pimelic acid, or by incorporation into a biotin homolog or other toxic intermediate.

XIIA
Isolation of Azelaic Acid Resistant Mutants of *B. subtilis*

On minimal agar, azelaic acid at 2 g/l (about $10^{-2}$ M) severely inhibited growth of PY79, although it did not kill or completely prevent growth. Seven spontaneous mutants that outgrew the background of PY79 on 2 g/l Azelaic acid were isolated. The resistance to azelaic acid appeared to be a stable trait in all but one case (see below). The seven mutants were provisionally named PA1-PA7 (PY79 Azelaic acid resistant). PA1 through PA7 were grown in test tubes in VY medium, and biotin production was assayed using *E. coli* indicator strains (Table 15). The mutants fell into two classes, those that yielded more biotin than PY79 (PA5, PA6) and those that were similar to PY79 (PA1, 2, 3, and 7). PA4 appeared to be either unstable or not a true mutant and was dropped from further study. Applicants also noticed that the mutants fell into two classes with respect to colony size on minimal agar with 2 g/l azelaic acid, and that these two classes corresponded to the two classes of biotin producers (Table 11). The mutants with the most biotin in the supernatant (PA5 and PA6) gave small colonies, while the biotin non-secreters, PA1, 2, 3, and 7, gave large colonies. PA1 and PA3 secreted a compound that cross-fed PY79 (i.e., reversed the azelaic acid inhibition of PY79) on minimal plates containing 2 g/l azelaic acid.

Representatives of the two classes of azelaic acid resistant mutants, PA3 and PA6, were chosen for further characterization. In liquid minimal cultures containing serially diluted azelaic acid, PA3 and PA6 showed clear resistance to azelaic acid compared to the parent, PY79 (FIG. 18). However, the dose response curves of PA3 and PA6 were distinct from each other. PA3 showed greater resistance than PA6, and at lower concentrations of azelaic acid PA6 did not grow to the same cell density as PA3 or PY79.

XIIB
Mapping of Azelaic Acid Resistant Mutants

To map the azelaic acid resistant mutations in PA3 and PA6, Applicants determined whether either mutation maps at birA or at the biotin operon. In the first case, PBS1 transducing lysates from PA3 and PA6 were applied to strain RL1 (trpC2), and Trp+ transductants were selected. The trpC2 and birA loci are about 90% linked by transduction. The Trp+ transductants were then screened for azelaic acid resistance by patching to minimal agar containing 2 g/l azelaic acid. No Trp+ transductants were azelaic acid resistant, demonstrating that neither mutation is linked to trpC2, and therefore neither is a birA mutation. The PA3 mutation showed strong linkage to bio in two transductions (one into PY79 $P_{bio}$::cat17 and one into PY79 bioW::cat7), while the PA6 mutation did not.

XIIC
Effect of Azelaic Acid Resistance Mutations on Biotin Production

Another approach to altering biotin regulation is to combine either of the azaleic acid resistant mutations with a birA mutation.

The birA mutation from either HB3 or α-DB16 was introduced into either PA3 or PA6 by a two step transduction process. First, PA3 and PA6 were made Trp− by transduction with trpE::Tn917lac (Perkins and Youngman, (*Proc. Nat'l Acad. Sci USA* 83:140–144 (1986)) selecting for erythromycin resistance. The birA mutations were transduced from HB3 or α-DB16, selecting for Trp+. Parents and Trp+ transductants were screened for homobiotin resistance and azelaic acid resistance. PA6 was homobiotin sensitive, so double mutants could be identified among Trp+ transductants by screening for homobiotin resistant colonies. Only about 60% of Trp+ transductants were also homobiotin resistant (this may be due to Tn917 distortion of the map distance between birA and trpE normally 90% linkage by transduction). PA3 was resistant to homobiotin, so direct identification of double mutants was not possible. However, 60% of the transductants were double mutants as judged by increased biotin secretion, see below.

The parent strains, putative PA3 birA double mutants, and actual PA6 birA mutants, were tested for biotin and vitamer production in VY test tube cultures. As shown in Table 18, the double mutants derived from PA3 produced about four to six fold more vitamer and twice as much biotin as the birA parent. Double mutants derived from PA6 produced similar or only slightly more biotin and vitamer than the birA parent. Clearly, the PA3 mutation aids biotin production in a deregulated strain.

XIID
Additional Azelaic Acid Resistant Mutants

In addition to the azelaic acid resistant mutants of the types represented by PA3 and PA6, several other azelaic acid resistant mutants that represent at least two new classes have been isolated as spontaneous mutants from the PY79 strain background.

Eleven additional mutants were partially mapped by transduction as described above to determine if the azelaic acid resistant mutation was linked to birA or to the bio operon. None were linked to trpC2, so by inference, none were at the birA locus. On the other hand, eight of the eleven tested were linked to the bio operon. Of those eight, two were tightly linked to the bio promoter, as was PA3, while six were substantially less than 100% linked to the bio promoter, suggesting that the mutations were in the bio operon well downstream from the promoter. Thus this latter group of six mutants represents another class of azelaic acid resistant mutants distinct from PA3 and PA6. This group includes BI514, BI521, BI532, BI535, BI537 and BI545. This group of mutants is likely to include mutants that have increased capacity to produce or utilize pimelic acid, for example bioI or bioW mutants.

Three of the new mutants did not map at birA nor at the bio operon. This group includes BI523, BI544, and BI549, and is likely to contain mutants that produce increased levels of pimelic acid precursors or that are more efficient at converting various biotin precursors into biotin. None of this group were equivalent to PA6, since unlike PA6, they all grew to the same density as PY79 (wild type) in a minimal medium lacking azelaic acid.

The new mutants are summarized in Table 19. Although none lead to significantly increased biotin production by themselves, these mutations are likely to increase biotin production when combined with other biotin deregulating mutations as was the case for PA3.

Applicants have deposited strains BI282, BI304, BI274, HB3, BI421, HB43, PA3, BI535 and BI544 described above with the American Type Culture Collection in Rockville, Md., and they have received accession numbers ATCC and, respectively. They or their assignees agree that these ieposits will be made publically available without restriction upon issuance of a United States patent.

Other embodiments are within the following claims.

TABLE 17

Biotin and vitamer production by azelaic acid resistant mutants in test tube cultures.

| Strain | Colony size on 2 g/l azelaic acid | Biotin (µg/l) | Vitamers (µg/l) |
| --- | --- | --- | --- |
| PY79 | tiny | 10 | 11 |
| PA1 | large | 10 | 13 |
| PA2 | large | 10 | 12 |
| PA3 | large | 10 | 12 |
| PA4 | tiny | 10 | 11 |
| PA7 | large | 10 | 12 |
| PA5 | small | 30 | 60 |
| PA6 | small | 30 | 60 |
| VY Medium (no cells) | — | 30 | 100 |

TABLE 18

Biotin and vitamer production by birA/azl$^r$ double mutants

| Parent strain | Donor for birA gene | Isolate number | Homobiotin resistant/ sensitive | Biotin[a] (µg/l) | Vitamers[b] (µg/l) |
| --- | --- | --- | --- | --- | --- |
| VY medium | — | | — | 22 | 25 |
| PY79 | — | | S | 6 | 10 |
| PA3 | — | | R | 5 | 9 |
| PA3 | HB3 | 1 | R | 120 | 690 |
| PA3 | HB3 | 2 | R | 100 | 440 |
| PA3 | α-DB16 | 1 | R | 100 | 690 |
| PA6 | — | | S | 11 | 16 |
| PA6 | HB3 | 2 | R | 46 | 200 |
| PA6 | HB3 | 6 | R | 50 | 120 |
| PA6 | α-DB16 | 8 | R | 53 | 220 |
| PA6 | α-DB16 | 14 | R | 56 | 200 |
| HB3 | — | | R | 44 | 110 |
| α-DB16 | — | | R | 46 | 140 |

[a]Assayed using *L. plantarum* str3
[b]Assayed using *S. cerevisiae*

TABLE 19

Additional Azelaic Acid Resistant Mutants

| Strain Name | Linkage to $P_{bio}$[a] |
|---|---|
| BI530 | 100 |
| BI533 | 100 |
| BI514 | 70 |
| BI521 | 90 |
| BI532 | 80 |
| BI535 | 40 |
| BI537 | 40 |
| BI545 | 90 |
| BI523 | 0 |
| BI544 | 0 |
| BI549 | 0 |
| PA3 | 100 |
| PA6 | 0 |
| PY79 (wild type) | — |

[a]Approximate linkage in percent BIO+, azelaic acid resistant upon PBS1 transduction into PY79 $P_{bio}$::cat17

What is claimed is:

1. A method of selecting a mutant *Bacillus subtilis* cell characterized in being deregulated for biotin production, said method comprising:
   (a) providing a population of *Bacillus subtilis* cell;
   (b) allowing said population to reproduce in the presence of azelaic acid;
   (c) selecting a cell that is resistant to said azelaic acid; and
   (d) screening said cell, or a daughter cell further mutated to deregulate biotin production, for the ability to overproduce biotin.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 8478
      (B) TYPE: nucleic acid
      (C) STRANDEDNESS: double
      (D) TOPOLOGY: linear (xi) SEQUENCE DESCRIPTION: SEQ ID NO: 1:

```
CGCATCGGAG ATCCAAAGCC TGATCGCGCC GCGCCCGCAC CTTAGTCTTG TTGGTGTACA      60

CGATCGGTTA ACGCCGGCTG AGGGCGTGGA CAAAATCGAA AAAGAATTGA CAGCTGTCTA     120

TGCTGGACAG GGAGCTGCTG ATTGCTACCG AGTGGTCCGT TCTGCTTCGG GACATTTCGA     180

AACAGCAGTT ATAAGGCATG AAGCTGTCCG GTTTTTGCAA AAGTGGCTGT GACTGTAAAA     240

AGAAATCGAA AAAGACCGTT TTGTGTGAAA ACGGTCTTTT TGTTTCCTTT TAACCAACTG     300

CCATAAATCG ATCCTTTCTT CTATTGACAG AAACAGGAGA GAATAATATA TTCTAATTGT     360

TAACCTTTGA ATATAATTGG TTAACAATTT AGGTGAGAAG CGCTACACGT TCTTCAGTTA     420

TCAGTGAAAG GGCGAGAAAT GATGCAAGAA GAAACTTTTT ATAGTGTCAG AATGAGGGCT     480

TCAATGAATG GATCTCATGA AGACGGCGGA AAGCATATAT CCGGCGGAGA ACGGCTTATT     540

CCTTTCCATG AGATGAAGCA TACAGTCAAT GCTTATTAG AAAAAGGGTT ATCCCATTCA     600

AGAGGAAAAC CTGATTTTAT GCAAATTCAA TTTGAAGAGG TACATGAATC GATAAAAACC     660

ATTCAGCCAT TGCCTGTGCA TACGAATGAA GTGAGCTGCC CGGAAGAAGG ACAAAAGCTT     720

GCCCGATTGT TATTGGAAAA AGAAGGCGTT TCACGAGACG TGATTGAAAA AGCATATGAA     780

CAAATCCCTG AATGGTCAGA TGTCAGGGGT GCGGTGTTGT TTGATATTCA TACAGGCAAG     840

CGAATGGATC AAACAAAGA AAAAGGGGTG CGGGTCTCCA GAATGGATTG GCCGGACGCT     900

AATTTTGAAA AATGGGCGCT TCACAGTCAC GTGCCAGCTC ATTCAAGAAT AAAAGAGGCC     960

CTTGCGCTCG CTTCAAAGGT AAGCCGGCAC CCGGCAGTCG TTGCAGAATT ATGCTGGTCG    1020

GACGATCCGG ATTACATAAC AGGCTATGTT GCGGGTAAGA AATGGGCTA TCAGCGTATT    1080
```

```
ACAGCAATGA AAGAATACGG GACTGAAGAG GGCTGCCGAG TCTTTTTTAT TGATGGATCC    1140

AATGATGTAA ACACGTACAT ACATGACCTG GAGAAGCAGC CTATTTTAAT AGAGTGGGAG    1200

GAAGATCATG ACTCATGATT TGATAGAAAA AAGTAAAAAG CACCTCTGGC TGCCATTTAC    1260

CCAAATGAAA GATTATGATG AAAACCCCTT AATCATCGAA AGCGGGACTG GAATCAAAGT    1320

CAAAGACATA AACGGCAAGG AATACTATGA CGGTTTTTCA TCGGTTTGGC TTAATGTCCA    1380

CGGACACCGC AAAAAGAAC TAGATGACGC CATAAAAAAA CAGCTCGGAA AAATTGCGCA     1440

CTCCACGTTA TTGGGCATGA CCAATGTTCC AGCAACCCAG CTTGCCGAAA CATTAATCGA    1500

CATCAGCCCA AAAAAGCTCA CGCGGGTCTT TTATTCAGAC AGCGGCGCAG AGGCGATGGA    1560

AATAGCCCTA AAAATGGCGT TCAGTATTG GAAGAACATC GGGAAGCCCG AGAAACAAAA     1620

ATTCATCGCA ATGAAAAACG GGTATCACGG TGATACGATT GGCGCCGTCA GTGTCGGTTC    1680

AATTGAGCTT TTTCACCACG TATACGGCCC GTTGATGTTC GAGAGTTACA AGGCCCCGAT    1740

TCCTTATGTG TATCGTTCTG AAAGCGGTGA TCCTGATGAG TGCCGTGATC AGTGCCTCCG    1800

AGAGCTTGCA CAGCTGCTTG AGGAACATCA TGAGGAAATT GCCGCGCTTT CCATTGAATC    1860

AATGGTACAA GGCGCGTCCG GTATGATCGT GATGCCGGAA GGATATTTGG CAGGCGTGCG    1920

CGAGCTATGT ACAACATACG ATGTCTTAAT GATCGTTGAT GAAGTCGCTA CAGGCTTTGG    1980

CCGTACAGGA AAAATGTTTG CGTGCGAGCA CGAGAATGTC CAGCCTGATC TGATGGCTGC    2040

CGGTAAAGGC ATTACAGGAG GCTATTTGCC AATTGCCGTT ACGTTGCCA CTGAAGACAT     2100

CTATAAGGCA TTCTATGATG ATTATGAAAA CCTAAAAACC TTTTTCCATG GCCATTCCTA    2160

TACAGGCAAT CAGCTTGGCT GTGCGGTTGC GCTTGAAAAT CTGGCATTAT TTGAATCTGA    2220

AAACATTGTG GAACAAGTAG CGGAAAAAAG TAAAAAGCTC CATTTCTTC TTCAAGATCT     2280

GCACGCTCTT CCTCATGTTG GGGATATTCG GCAGCTTGGC TTTATGTGCG GTGCAGAGCT    2340

TGTACGATCA AAGGAAACTA AAGAACCTTA CCCGGCTGAT CGGCGGATTG GATACAAAGT    2400

TTCCTTAAAA ATGAGAGAGT TAGGAATGCT GACAAGACCG CTTGGGGACG TGATTGCATT    2460

TCTTCCTCCT CTTGCCAGCA CAGCTGAAGA GCTCTCGGAA ATGGTTGCCA TTATGAAACA    2520

AGCGATCCAC GAGGTTACGA GCCTTGAAGA TTGATTCCTG GTTAAACGAG CGGTTAGACA    2580

GAATGAAAGA AGCCGGCGTA CATCGTAACC TGCGGTCAAT GGATGGAGCG CCGGTTCCAG    2640

AGAGGAATAT TGATGGCGAA ATCAAACGG TCTGGTCCTC AAACAATTAT TTAGGGCTCG     2700

CAAGCGATAG ACGTTTGATC GATGCAGCCC AAACAGCATT GCAGCAATTT GGGACAGGAA    2760

GCAGCGGTTC ACGTTTAACG ACAGGCAATT CGGTCTGGCA TGAAAAGCTA GAAAAGAAGA    2820

TTGCCAGCTT TAAACTGACA GAAGCGGCCC TGCTGTTTTC GAGCGGTTAC TTGGCCAATG    2880

TCGGTGTCCT TTCATCCTTG CCAGAAAAGG AAGATGTCAT TTTAAGTGAC CAGCTCAATC    2940

ATGCAAGTAT GATCGACGGC TGCCGACTTT CTAAGGCTGA TACAGTTGTT TATCGGCATA    3000

TTGATATGAA TGATCTTGAA AACAAGCTGA ATGAAACACA GCGTTATCAG CGCCGTTTTA    3060

TCGTAACAGA CGGAGTATTC AGCATGGATG GCACAATCGC CCCTCTTGAT CAGATCATCT    3120

CACTTGCGAA ACGCTATCAT GCCTTCGTGG TCGTTGATGA TGCCCACGCA ACAGGAGTTT    3180

TGGGCGATTC GGGACAAGGA ACGAGTGAAT ACTTTGGTGT TTGTCCCGAC ATTGTTATCG    3240

GCACCTTAAG CAAAGCTGTT GGCGCGGAAG GAGGTTTTGC GGCAGGATCA GCGGTCTTCA    3300

TCGACTTTTT GCTGAACCAT GCCAGAACAT TTATCTTTCA AACCGCTATT CCGCCAGCCA    3360

GCTGTGCGGC TGCTCACGAG GCTTTCAACA TCATTGAAGC CAGCAGGGAA AAACGACAGC    3420

TTTTATTTTC TTATATCAGC ATGATCAGAA CCAGTCTGAA GAATATGGGT TATGTGGTGA    3480
```

```
AAGGAGATCA CACACCGATT ATTCCTGTAG TCATTGGCGA TGCCCATAAA ACGGTCCTAT    3540

TTGCTGAAAA ACTGCAGGGC AAGGGAATTT ATGCTCCTGC CATTCGGCCG CCAACCGTTG    3600

CGCCGGGTGA AAGCCGGATT CGAATTACAA TCACGTCTGA CCACAGTATG GGTGATATTG    3660

ATCATTTGCT GCAAACATTT CATTCAATCG GAAAGGAGCT GCACATCATT TGAGGGGTTT    3720

TTTTGTGACG GGAACTGATA CAGAAGTAGG GAAAACGGTT ATATCCAGCG GTCTTGCTGC    3780

CTTATTGAAA GACAATAATA GACATGTCGG GGTGTATAAA CCATTTTTAA GCGGGATATC    3840

GCGCCATCAT CCAGATAGTG ATACAAGTTT GCTGAAAGAT ATGTCGCAGA CCAGTCTTTC    3900

TCATGAAGAC ATTACGCCTT TTGCCTTCAA GGCGCCGCTT GCACCATACG TTGCAGGGAA    3960

ACTTGAGGGA AAGACTGTCA CCATGGAAGA GGTTTTAAGC CATTGGGGGC GGATTAGAGA    4020

AAAACATGAA TGCTTCATCG TAGAAGGTGC AGGCGGTATT TCTGTGCCAT GGGAGAGGA    4080

CTATTTGGTC AGTCATGTCA TAAAAGCGTT GCAGCTTCCC ATGATTATTG TGGCGCGTCC    4140

TCGCCTTGGA ACCATTAATC ATACCTTTTT AACTGTCAAA TATGCAGAAA GCATGGGGCT    4200

TCCAATCGCC GGAATTATCA TCAATGGAAT CAGTGACTCT CCTGATGAAG ATGAAAAAAC    4260

CAATCCTGAG ATGATTGAGC GCTTATGCGG TGTGCCGATT TTAGGGGTTA CGCCAAAGCT    4320

TGCCAACGTG ACGAAAGAAA CGGTTCTACA TATGGTAAAA GACCATATCA ATCTATCATT    4380

ACTGATGAAT CAAGTGGGGG TATGAGAATG AATCAATGGA TGGAACTCGC AGACCGGGTG    4440

CTGGCTGGAG CAGAAGTGAC TGACGAAGAG GCGCTTTCAA TATTACATTG TCCTGATGAA    4500

GATATTTTGC TATTAATGCA CGGGGCTTTT CACATCAGAA AACACTTTTA CGGAAAAAAA    4560

GTAAAGCTCA ATATGATTAT GAATGCGAAA TCCGGGCTCT GCCCGGAAAA CTGCGGCTAT    4620

TGTTCACAGT CTGCGATTTC GAAAGCGCCG ATTGAGTCTT ACCGGATGGT GAATAAGGAA    4680

ACGCTGCTTG AAGGCGCGAA GCGGGCGCAC GATCTGAATA TCGGCACATA TTGTATCGTG    4740

GCAAGCGGCA GAGGTCCGTC TAACAGAGAA GTGGATCAGG TCGTAGATGC GGTTCAGGAA    4800

ATTAAAGAGA CGTATGGACT GAAGATTTGT GCATGTCTTG GACTGTTGAA GCCAGAGCAG    4860

GCGAAGCGGC TCAAAGATGC AGGAGTAGAC CGCTATAATC ATAATTTGAA TACGTCACAG    4920

AGAAACCATT CAAACATCAC AACCTCACAT ACATACGATG ACAGAGTCAA TACGGTTGAA    4980

ATCGCAAAAG AATCGGGGCT GTCTCCGTGT TCAGGCGCCA TTATCGGGAT GAAGGAGACG    5040

AAACAGGATG TCATTGACAT CGCCAAAAGC TTGAAGGCTC TTGACGCGGA TTCCATTCCT    5100

GTGAATTTTT TGCATGCAAT TGATGGCACG CCGTTAGAAG GCGTCAACGA ATTAAACCCG    5160

CTGTATTGTT TAAAAGTGCT GGCGCTGTTC CGTTTTATCA ATCCATCAAA AGAAATTCGC    5220

ATTTCCGGAG GAAGAGAGGT CAATCTCCGC ACATTGCAGC CATTAGGGCT TTACGCCGCA    5280

AACTCCATTT TTGTCGGAGA CTACTTAACA ACTGCCGGGC AAGAGGAGAC GGAGGATCAT    5340

AAAATGCTGA GTGATTTAGG CTTTGAAGTT GAATCAGTCG AAGAAATGAA GGCTAGTTTA    5400

AGTGCGAAAA GCTGAAAGAA TCAATAAAAG CAATCGGTAT GATGTCGATT GTTTTTATTT    5460

TTGAACAGAA AGGAGAAAAT CACGTGACAA TTGCATCGTC AACTGCATCT TCTGAGTTTT    5520

TGAAAAACCC ATATTCTTTT TACGACACAT TGCGAGCTGT TCATCCTATC TATAAAGGGA    5580

GTTTCTTAAA ATACCCGGGC TGGTATGTCA CAGGATATGA AGAAACGGCT GCTATTTTGA    5640

AAGATGCGAG ATTCAAAGTC CGCACCCCGC TGCCTGAGAG CTCAACCAAA TATCAGGACC    5700

TTTCACATGT GCAAAATCAA ATGATGCTGT TTCAGAACCA GCCTGATCAT AGACGATTGC    5760

GGACGCTTGC CAGCGGAGCG TTTACGCCGA GAACGACAGA GAGTTATCAG CCGTATATCA    5820
```

```
TTGAAACTGT CCATCATTTG CTTGATCAAG TGCAAGGTAA AAAAAAGATG GAGGTCATTT    5880

CGGACTTTGC TTTTCCTTTA GCAAGTTTTG TCATAGCTAA CATTATAGGT GTACCGGAGG    5940

AAGATAGGGA GCAATTAAAG GAGTGGGCTG CGAGTCTCAT TCAAACGATT GATTTTACCC    6000

GCTCAAGAAA GGCATTAACA GAGGGCAATA TTATGGCTGT GCAGGCTATG CATATTTCA    6060

AAGAGCTGAT TCAAAAGAGA AAACGCCACC CTCAACAGGA TATGATCAGC ATGCTCTTGA    6120

AGGGGAGAGA AAAGGATAAG CTGACGGAAG AGGAGGCGGC ATCTACGTGC ATATTGCTGG    6180

CGATCGCCGG ACATGAGACA ACGGTCAATC TCATCAGCAA TTCAGTCCTT TGTCTGCTGC    6240

AGCATCCAGA ACAGCTTTTG AAACTGAGAG AAAATCCAGA TCTTATTGGT ACCGCAGTCG    6300

AGGAATGTTT ACGCTATGAA AGCCCCACGC AAATGACAGC CAGAGTTGCG TCAGAGGATA    6360

TTGACATCTG CGGGGTGACG ATCCGTCAAG GAGAACAAGT CTATCTTTTG TTAGGAGCGG    6420

CTAATCGAGA CCCTAGCATA TTCACGAACC CCGATGTCTT CGATATTACG AGAAGTCCTA    6480

ATCCGCATCT TTCATTCGGG CATGGCCATC ATGTTTGCTT AGGGTCCTCG CTGGCACGAT    6540

TAGAAGCGCA AATTGCGATT AACACTCTTC TGCAGCGAAT GCCCAGCCTT AATCTTGCGG    6600

ATTTTGAATG GCGGTATCGG CCGCTTTTTG GATTTCGGGC GCTTGAGGAG CTGCCGGTGA    6660

CTTTTGAATA AGCCTAAGAA TGTGAGTGCC AAAAAAGTGT CAGCCCCGCC GAAAATGGGC    6720

AATCTATAAA AAGGGGAGT GAACATCGTG AAAAAGTGC TGATCGCCGG CGGAAATGGT    6780

GTGATTGGGA GACTGCTTGC TGAAGGGCTT ATTTCAGACT ATGAAGTGAC TGTGCTTGAT    6840

AAAGATCATT TCGATGGCAA AGCCTCTTCC ATTCAGGCTG ACGCGGCAAA TTATGAGGAG    6900

CTGTTGAAGA AGATTCCAAA AGATACCGAT GCCATCTTGA ATTTACTCGC TGTGAAAATC    6960

AAATACGATA TTATGGACAT CGCTGAGTTT GAAAAAATGA CGGATGTTTT CTATAGGGCA    7020

AGCTATTATC TGTGCCGTGC GGCAGCGGAG CTCGGCATTC AAAAGCTCGT GTTCGCCAGC    7080

AGCAATCATG TCACAGATGT ATATGAAAAA GACGGGCGCT CGCTCTTAGG ACGGGAAATC    7140

ACAACAAGCG ATTATCCGCT GTCAAAAAAC TTGTACGGTG TATTAAAGCT GACCTCTGAA    7200

CAGATCGGCC ATTTGTTTTA TTTGGAAAAT AAGCTATCAG TAATCAACCT TCGAATCGGA    7260

ACAGTCGTGA CAGATGAAAT GGATACGCTG CATGAAAAAG AACGGACGAA AAAGACACTG    7320

CTTTCTCACC CCGATCTGCT GTCGATTTTC AAAGCCGCCA TTGAGACCAA CATCCGGTAT    7380

GGCACTTATT ACGCCGTCTC TGATAATCCG GGCCGGCCAT GGTCCATTGA ATCTGCCGTG    7440

AATGAACTTG GGTTTTCGCC ACAAATCAAT ACGGCTGAAC TTCTGAACGA GGAGGAGAAC    7500

GGAGCATAAT CATTTTCTAA GATTATGCTC TTTTTCTTTT GTTATCGGTC TCAATTCGCG    7560

GCAGCCCCCG CCCGGCCGGG GACACTGTTC AAATGATTAT AGACATGGCA ATCACAGATT    7620

TGCTACATTT TAGACACGAT ATCGTCACAT GCTGAGCTCG GTTTCCAAAA ATATGATAAC    7680

GCTTACAAAG GGAGGTGGGA GCTATCGCAC ATTCACTGAA AAACCGTCTG TTTGATATGT    7740

TGATTTATGG TTTCTTGCTG ATGTTCGCTT TAATATGCGT ACTTCCGTTC ATTCATGTTA    7800

TCGCAGCATC CTTTGCCACA GTAGAAGAAG TCGTGTCGAA AAAATTTATT TTAATACCGA    7860

CCACTTTTTC GCTAGATGCT TATCGCTACA TTTTTTCAAC AGATATTATT TATAAGAGTT    7920

TGCTTGTTTC TGTGTTTGTG ACAGTGATAG GCACTGCGGT CAGCATGTTT CTTTCGTCAC    7980

TGATGGCTTA CGGGTTATCC CGCCGTGATT TAATCGGCCG GCAGCCGCTC ATGTTTCTCG    8040

TCGTATTTAC GATGCTGTTT AGCGGCGGCA TGATTCCGAC TTTCCTTGTG GTCAAATCGC    8100

TTGGATTGCT CGATTCTTAC TGGGCGCTTA TTTTGCCGAC AGCCATTAAT GCCTTTAACC    8160

TGATCATTCT GAAAAACTTC TTTCAAAATA TCCCGTCAAG CCTGGAAGAG TCCGCGAAAA    8220
```

```
TTGACGGGTG CAATGATCTG GGCATATTCT TTAAAATTGT GCTGCCGCTG TCTCTTCCTG    8280

CGATCGCAAC GATTTCACTA TTTTATGCGG TCACGTATTG GAACACGTAT ATGACAGCGA    8340

TCTTGTACTT AAATGATTCA GCAAAATGGC CAATTCAGGT GCTTCTGCGC CAAATCGTCA    8400

TTGTATCAAG CGGTATGCAG GGGGATATGT CTGAAATGGG GTCGGGCAGC CCGCCGCCTG    8460

AGCAAACCAT NNNNNTGG                                                  8478

(2) INFORMATION FOR SEQ ID NO:   2:

(i) SEQUENCE CHARACTERISTICS:
        (A) LENGTH:            29
        (B) TYPE:              nucleic acid
        (C) STRANDEDNESS:      double
        (D) TOPOLOGY:          linear (xi) SEQUENCE DESCRIPTION: SEQ ID NO: 2:

TTGACANNNN NNNNNNNNNN NNNTATATT                                         29

(2) INFORMATION FOR SEQ ID NO:   3:

(i) SEQUENCE CHARACTERISTICS:
        (A) LENGTH:            29
        (B) TYPE:              nucleic acid
        (C) STRANDEDNESS:      double
        (D) TOPOLOGY:          linear (xi) SEQUENCE DESCRIPTION: SEQ ID NO: 3:

TTGACANNNN NNNNNNNNNN NNNTATAAT                                         29

(2) INFORMATION FOR SEQ ID NO:   4:

(i) SEQUENCE CHARACTERISTICS:
        (A) LENGTH:            30
        (B) TYPE:              nucleic acid
        (C) STRANDEDNESS:      double
        (D) TOPOLOGY:          linear (xi) SEQUENCE DESCRIPTION: SEQ ID NO: 4:

TTGTAANNNN NNNNNNNNNN NNNNTAATAT                                        30

(2) INFORMATION FOR SEQ ID NO:   5:

(i) SEQUENCE CHARACTERISTICS:
        (A) LENGTH:            29
        (B) TYPE:              nucleic acid
        (C) STRANDEDNESS:      double
        (D) TOPOLOGY:          linear (xi) SEQUENCE DESCRIPTION: SEQ ID NO: 5:

TTGATANNNN NNNNNNNNNN NNNAAAAGT                                         29

(2) INFORMATION FOR SEQ ID NO:   6:

(i) SEQUENCE CHARACTERISTICS:
        (A) LENGTH:            29
        (B) TYPE:              nucleic acid
        (C) STRANDEDNESS:      double
        (D) TOPOLOGY:          linear (xi) SEQUENCE DESCRIPTION: SEQ ID NO: 6:

TTGAAANNNN NNNNNNNNNN NNNTCTTAT                                         29

(2) INFORMATION FOR SEQ ID NO:   7:
```

(i) SEQUENCE CHARACTERISTICS:
           (A) LENGTH:           300
           (B) TYPE:             nucleic acid
           (C) STRANDEDNESS:     double
           (D) TOPOLOGY:         linear (xi) SEQUENCE DESCRIPTION: SEQ ID NO: 7:

AAGCTGTCCG GTTTTTGCAA AAGTGGCTGT GACTGTAAAA AGAAATCGAA AAAGACCGTT      60

TTGTGTGAAA ACGGTCTTTT TGTTTCCTTT TAACCAACTG CCATAAATCG ATCCTTTCTT     120

CTATTGACAG AAACAGGAGA GAATAATATA TTCTAATTGT TAACCTTTGA ATATAATTGG     180

TTAACAATTT AGGTGAGAAG CGCTACACGT TCTTCAGTTA TCAGTGAAAG GGCGAGAAAT     240

GATGCAAGAA GAAACTTTTT ATAGTGTCAG AATGAGGGCT TCAATGAATG GATCTCATGA     300

(2) INFORMATION FOR SEQ ID NO:   8:

(i) SEQUENCE CHARACTERISTICS:
           (A) LENGTH:           36
           (B) TYPE:             nucleic acid
           (C) STRANDEDNESS:     double
           (D) TOPOLOGY:         linear (xi) SEQUENCE DESCRIPTION: SEQ ID NO: 8:

AATGTGTTAA CTTAAAAACT ATAGTTGGTT AACTAA                                36

(2) INFORMATION FOR SEQ ID NO:   9:

(i) SEQUENCE CHARACTERISTICS:
           (A) LENGTH:           40
           (B) TYPE:             nucleic acid
           (C) STRANDEDNESS:     double
           (D) TOPOLOGY:         linear (xi) SEQUENCE DESCRIPTION: SEQ ID NO: 9:

CTAATTGTTA ACCTTTGAAT ATAATTGGTT AACAATTTAG                            40

(2) INFORMATION FOR SEQ ID NO:   10:

(i) SEQUENCE CHARACTERISTICS:
           (A) LENGTH:           38
           (B) TYPE:             nucleic acid
           (C) STRANDEDNESS:     double
           (D) TOPOLOGY:         linear (xi) SEQUENCE DESCRIPTION: SEQ ID NO: 10:

GGCCAAGCTT GTCGACCGAA ACAGCAGTTA TAAGGCAT                              38

(2) INFORMATION FOR SEQ ID NO:   11:

(i) SEQUENCE CHARACTERISTICS:
           (A) LENGTH:           24
           (B) TYPE:             nucleic acid
           (C) STRANDEDNESS:     double
           (D) TOPOLOGY:         linear (xi) SEQUENCE DESCRIPTION: SEQ ID NO: 11:

GGCCCGTCTA GAGCTTCTCA CCTA                                             24

(2) INFORMATION FOR SEQ ID NO:   12:

(i) SEQUENCE CHARACTERISTICS:
           (A) LENGTH:           35
           (B) TYPE:             nucleic acid
           (C) STRANDEDNESS:     double
           (D) TOPOLOGY:         linear (xi) SEQUENCE DESCRIPTION: SEQ ID NO: 12:

GGCCGAGAAG CTCTAGACGT TCTTCAGTTA TCAGT                                    35

(2) INFORMATION FOR SEQ ID NO:    13:

(i) SEQUENCE CHARACTERISTICS:
        (A) LENGTH:              24
        (B) TYPE:                nucleic acid
        (C) STRANDEDNESS:        double
        (D) TOPOLOGY:            linear (xi) SEQUENCE DESCRIPTION: SEQ ID NO: 13:

CGCCAGGGTT TTCCCAGTCA CGAC                                                24

(2) INFORMATION FOR SEQ ID NO:    14:

(i) SEQUENCE CHARACTERISTICS:
        (A) LENGTH:              28
        (B) TYPE:                nucleic acid
        (C) STRANDEDNESS:        double
        (D) TOPOLOGY:            linear (xi) SEQUENCE DESCRIPTION: SEQ ID NO: 14:

TAGAAGAAAG GCTCGAGTTA TGGCAGTT                                            28

(2) INFORMATION FOR SEQ ID NO:    15:

(i) SEQUENCE CHARACTERISTICS:
        (A) LENGTH:              28
        (B) TYPE:                nucleic acid
        (C) STRANDEDNESS:        double
        (D) TOPOLOGY:            linear (xi) SEQUENCE DESCRIPTION: SEQ ID NO: 15:

AACTGCCATA ACTCGAGCCT TTCTTCTA                                            28

(2) INFORMATION FOR SEQ ID NO:    16:

(i) SEQUENCE CHARACTERISTICS:
        (A) LENGTH:              9
        (B) TYPE:                amino acid
        (C) STRANDEDNESS:
        (D) TOPOLOGY:            linear (xi) SEQUENCE DESCRIPTION: SEQ ID NO: 16:

Ala Val Arg Phe Leu Gln Lys Trp Leu
 1          5

(2) INFORMATION FOR SEQ ID NO:    17:

(i) SEQUENCE CHARACTERISTICS:
        (A) LENGTH:              21
        (B) TYPE:                amino acid
        (C) STRANDEDNESS:
        (D) TOPOLOGY:            linear (xi) SEQUENCE DESCRIPTION: SEQ ID NO: 17:

Met Met Gln Glu Glu Thr Phe Tyr Ser Val Arg Met Arg Ala Ser Met
 1          5               10              15

Asn Gly Ser His Glu
        20

(2) INFORMATION FOR SEQ ID NO:18:

(i) SEQUENCE CHARACTERISTICS:
        (A) LENGTH: 30 base pairs

-continued (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

GGCCCTCGAG GCCTACCTAG CTTCCAAGAA                          30

(2) INFORMATION FOR SEQ ID NO:19:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

GGCCTCTAGA GCGTCCTGCT GTTGTTAAGA                          30

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

GCCAATCCAT TCTGGAGA                                       18

(2) INFORMATION FOR SEQ ID NO:21:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

GGCCCTCGAG GCTATTGACG ACAGCTATGG TT                       32

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:22:

CCCTATATAT TTTTTCTTTA ATTAT                               25

(2) INFORMATION FOR SEQ ID NO:23:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
        (ii) MOLECULE TYPE: DNA (xi) SEQUENCE DESCRIPTION: SEQ ID NO:23:

CCCTATATAT TTTTTCTTTA ATTAT                                          25

(2) INFORMATION FOR SEQ ID NO:24:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

GGCCATTCTA CACGTGATTT TCTCCTTTCT GTCTAGAACA GGCGGGGTTG C              51

(2) INFORMATION FOR SEQ ID NO:25:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

AGAAAGGAGG TGA                                                       13
```